United States Patent
Zabel et al.

(10) Patent No.: US 11,384,146 B2
(45) Date of Patent: Jul. 12, 2022

(54) BTLA-BINDING ANTIBODIES FOR MODULATING IMMUNE RESPONSE AND TREATING DISEASE

(71) Applicants: LakePharma, Inc., Belmont, CA (US); TRIANNI, Inc., San Francisco, CA (US)

(72) Inventors: Brian A. Zabel, Redwood City, CA (US); John A. Lippincott, San Diego, CA (US); Yayue Zheng, Sunnyvale, CA (US); Megha Vaman Rao, Belmont, CA (US); Miao Tan, Fremont, CA (US); David P. Meininger, Seattle, WA (US)

(73) Assignees: Curia IP Holdings, LLC, Albany, NY (US); TRIANNI, Inc., San Francisco, CA (US)

( * ) Notice: Subject to any disclaimer, the term of this patent is extended or adjusted under 35 U.S.C. 154(b) by 0 days.

(21) Appl. No.: 16/836,006

(22) Filed: Mar. 31, 2020

(65) Prior Publication Data
US 2020/0325230 A1 Oct. 15, 2020

Related U.S. Application Data

(60) Provisional application No. 62/827,744, filed on Apr. 1, 2019.

(51) Int. Cl.
*C07K 16/28* (2006.01)
*A61K 45/06* (2006.01)
*A61P 25/28* (2006.01)
*C12N 15/63* (2006.01)

(52) U.S. Cl.
CPC .......... *C07K 16/2818* (2013.01); *A61P 25/28* (2018.01); *C12N 15/63* (2013.01); *A61K 45/06* (2013.01); *C07K 2317/565* (2013.01)

(58) Field of Classification Search
CPC .......... C07K 16/2818; C07K 2317/565; C07K 2317/515; C07K 2317/70; C07K 2317/76; A61P 25/28; A61P 35/00; C12N 15/63; A61K 45/06; A61K 2039/505
See application file for complete search history.

(56) References Cited

U.S. PATENT DOCUMENTS

| | | |
|---|---|---|
| 7,479,544 B2 | 1/2009 | Clark et al. |
| 8,563,694 B2 | 10/2013 | Mataraza et al. |

FOREIGN PATENT DOCUMENTS

| | | |
|---|---|---|
| WO | WO 2011/014438 A1 | 2/2011 |
| WO | WO 2016/176583 A1 | 11/2016 |
| WO | WO 2017/096017 A1 | 6/2017 |
| WO | WO 2017/144668 A1 | 8/2017 |

OTHER PUBLICATIONS

International Search Report ad Written Opinion for International Application No. PCT/US2020/025936, dated Jul. 29, 2020, 15 pages.
Assal et al., "Emerging targets in cancer immunotherapy: beyond CTLA-4 and PD-1", Immunotherapy (2015) 7(11), pp. 1169-1186.
Baeuerle and Baltimore, "NF-κB: Ten Years After", Cell, Oct. 4, 1996, vol. 87, pp. 13-20.
Baldwin et al., "The NF-κB and IκB Proteins: New Discoveries and Insights", Annu. Rev. Immunol., vol. 14, 1996, pp. 649-681.
Crawford and Wherry, "Editorial: Therapeutic potential of targeting BTLA", Journal of Leukocyte Biology, vol. 86, Jul. 2009, pp. 5-8.
Jefferis et al., "Interaction sites on human IgG-Fc for FcγR: current models", Immunol Lett, vol. 82, Issues 1-2, Jun. 3, 2002, pp. 57-65.

*Primary Examiner* — Hong Sang
*Assistant Examiner* — Sung Min Yoon
(74) *Attorney, Agent, or Firm* — Troutman Pepper Hamilton Sanders LLP (Rochester)

(57) ABSTRACT

The invention provides novel anti-BTLA antibodies, pharmaceutical compositions comprising such antibodies, and therapeutic methods of using such antibodies and pharmaceutical compositions for the treatment of diseases such as cancer or autoimmune disease.

7 Claims, 6 Drawing Sheets

Specification includes a Sequence Listing.

SEQUENCE LISTING

```
<160> NUMBER OF SEQ ID NOS: 214

<210> SEQ ID NO 1
<211> LENGTH: 124
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (124)..(124)
<223> OTHER INFORMATION: Xaa can be any naturally occurring amino acid

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ser Gly Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Gly Asp Tyr Tyr Gly Ser Gly Ser Tyr Pro Leu Phe Asp Tyr
            100                 105                 110
```

Trp Gly Gln Gly Thr Leu Val Ile Val Ser Ser Xaa
            115                 120

<210> SEQ ID NO 2
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 2

Ala Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Ser Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Phe Tyr Cys Gln Gln Phe Asn Asn Tyr Pro Pro
                85                  90                  95

Thr Phe Gly Pro Gly Thr Lys Val Asp Ile Lys
            100                 105

<210> SEQ ID NO 3
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Thr Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Val Leu Tyr Ser Thr Gly Trp Ser Phe Asp Tyr Trp Gly Gln
            100                 105                 110

Gly Thr Leu Val Thr Val Ser Ser Xaa
            115                 120

<210> SEQ ID NO 4
<211> LENGTH: 108
<212> TYPE: PRT
<213> ORGANISM: Artificial Sequence
<220> FEATURE:

<223> OTHER INFORMATION: synthetic amino acid sequence

<400> SEQUENCE: 4

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Arg Pro Gly Gln Ala Pro Arg Leu Leu
        35                  40                  45

Ile Tyr Gly Thr Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105
```

<210> SEQ ID NO 5
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 5

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Val Leu Tyr Ser Ser Gly Trp Ser Phe Asp Tyr Trp Gly Gln
            100                 105                 110

Gly Thr Leu Val Thr Val Ser Ser Xaa
        115                 120
```

<210> SEQ ID NO 6
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 6

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Phe Ser Ser Ser
            20                  25                  30
```

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105

<210> SEQ ID NO 7
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 7

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser His Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Val Val Leu Tyr Ser Ser Gly Trp Ser Phe Asp Tyr Trp Gly Gln
            100                 105                 110

Gly Thr Leu Val Thr Val Ser Ser Xaa
            115                 120

<210> SEQ ID NO 8
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 8

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Gln Gln Asp Tyr Asn Leu Pro

```
                    85                  90                  95

Leu Thr Phe Gly Gly Gly Thr Lys Val Glu Ile Lys
                100                 105

<210> SEQ ID NO 9
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Met Val Phe Ser Ser Gly Trp Tyr Phe Asp Tyr Trp Gly Gln
            100                 105                 110

Gly Thr Leu Val Thr Val Ser Ser Xaa
        115                 120

<210> SEQ ID NO 10
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 10

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asn Ile Thr Ser Ser
            20                  25                  30

Tyr Leu Ser Trp Tyr Gln Gln Lys Pro Gly Gln Ser Pro Arg Leu Leu
        35                  40                  45

Ile Tyr Asp Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
                100                 105

<210> SEQ ID NO 11
<211> LENGTH: 124
<212> TYPE: PRT
<213> ORGANISM: Artificial Sequence
```

```
<220> FEATURE:
<223> OTHER INFORMATION: synthetic amino acid sequence
<220> FEATURE:
<221> NAME/KEY: misc_feature
<222> LOCATION: (124)..(124)
<223> OTHER INFORMATION: Xaa can be any naturally occurring amino acid

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Val Gly Pro Gly Ser His Tyr Asn Pro His Asn Trp Phe Asp Pro
            100                 105                 110

Trp Gly Gln Gly Thr Leu Val Thr Val Ser Ser Xaa
        115                 120

<210> SEQ ID NO 12
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 12

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Thr Val Thr Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Phe Pro Ala Arg Phe Ser
    50                  55                  60

Val Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Trp Thr Phe Gly Gln Gly Thr Lys Val Glu Ile Lys
            100                 105

<210> SEQ ID NO 13
<211> LENGTH: 124
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (124)..(124)
<223> OTHER INFORMATION: Xaa can be any naturally occurring amino acid

<400> SEQUENCE: 13

Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Thr Phe Thr Asn Tyr
                20                  25                  30

Gly Ile Ile Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Thr Leu Arg Ser Asp Asp Thr Ala Val Tyr Tyr Cys
                85                  90                  95

Ala Arg Asp Tyr Tyr Ser Ser Gly Ser Tyr Gly Gly Trp Phe Asp Pro
                100                 105                 110

Trp Gly Gln Gly Thr Leu Val Thr Val Ser Ser Xaa
            115                 120
```

<210> SEQ ID NO 14
<211> LENGTH: 111
<212> TYPE: PRT
<213> ORGANISM: Artificial Sequence
<220> FEATURE:
<223> OTHER INFORMATION: synthetic amino acid sequence

<400> SEQUENCE: 14

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
                20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Val Asp Glu Ala Asp Tyr Tyr Cys Gln Thr Trp Gly
                85                  90                  95

Thr Gly Ile Arg Val Phe Gly Gly Gly Thr Lys Leu Thr Val Leu
                100                 105                 110
```

<210> SEQ ID NO 15
<211> LENGTH: 123
<212> TYPE: PRT
<213> ORGANISM: Artificial Sequence
<220> FEATURE:
<223> OTHER INFORMATION: synthetic amino acid sequence

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Ile Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
             85                  90                  95

Ala Arg Asp Tyr Tyr Ser Ser Gly Ser Tyr Gly Gly Trp Phe Asp Pro
            100                 105                 110

Trp Gly Gln Gly Thr Leu Val Thr Val Ser Ser
        115                 120

<210> SEQ ID NO 16
<211> LENGTH: 111
<212> TYPE: PRT
<213> ORGANISM: Artificial Sequence
<220> FEATURE:
<223> OTHER INFORMATION: synthetic amino acid sequence

<400> SEQUENCE: 16

Gln Leu Val Leu Thr Gln Ser Pro Ser Ala Ser Ala Ser Leu Gly Ala
1               5                  10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Val Asp Glu Ala Asp Tyr Tyr Cys Gln Thr Trp Gly
                85                  90                  95

Thr Gly Ile Arg Val Phe Gly Gly Gly Thr Lys Leu Thr Val Leu
            100                 105                 110

<210> SEQ ID NO 17
<211> LENGTH: 124
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (124)..(124)
<223> OTHER INFORMATION: Xaa can be any naturally occurring amino acid

<400> SEQUENCE: 17

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Ser Ser Ser Tyr
            20                  25                  30

Ala Met Ser Trp Val Arg Gln Ala Pro Gly Lys Gly Leu Glu Trp Val
            35                  40                  45

Ser Gly Ile Ser Gly Ser Gly Asp Ser Thr Tyr Tyr Ala Asp Ser Val
50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Asp Tyr Tyr Gly Ser Gly Ser Tyr Pro Leu Phe Asp Tyr
            100                 105                 110

Trp Gly Gln Gly Thr Arg Val Thr Val Ser Ser Xaa
        115                 120
```

-continued

```
<210> SEQ ID NO 18
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Ser Asp Ala Ser Ser Leu Glu Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Asn Tyr Pro Pro
                85                  90                  95

Thr Phe Gly Pro Gly Thr Lys Val Asp Ile Ile
            100                 105

<210> SEQ ID NO 19
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Tyr Tyr
            20                  25                  30

Tyr Trp Ser Trp Ile Arg Gln Pro Pro Gly Thr Gly Leu Glu Trp Ile
        35                  40                  45

Gly Tyr Ile Tyr Tyr Ser Gly Ser Thr Lys Tyr Asn Pro Ser Leu Lys
    50                  55                  60

Arg Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ile Arg Gly Asp Ser Tyr Gly Trp Asp Phe Asp Tyr Trp Gly Gln
            100                 105                 110

Gly Thr Leu Val Thr Val Ser Ser Xaa
        115                 120

<210> SEQ ID NO 20
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 20

Glu Ile Val Met Thr Gln Ser Pro Ala Thr Leu Ser Leu Ser Pro Gly
```

```
                1               5                  10                 15
            Glu Arg Ala Thr Leu Ser Cys Arg Ala Ser Gln Ser Ile Ser Asn Asn
                            20                  25                  30

Tyr Leu Phe Trp Tyr Gln Gln Lys Pro Gly Gln Ala Pro Arg Leu Leu
                        35                  40                  45

Ile Tyr Gly Ala Ser Thr Arg Ala Thr Gly Ile Pro Ala Arg Phe Ser
                    50                  55                  60

Gly Ser Gly Ser Gly Thr Asp Phe Thr Leu Thr Ile Ser Ser Leu Gln
             65                 70                  75                  80

Pro Glu Asp Phe Ala Val Tyr Tyr Cys Gln Gln Asp Tyr Asn Phe Pro
                            85                  90                  95

Leu Thr Phe Gly Gly Gly Thr Lys Val Glu Ile Lys
                        100                 105
```

<210> SEQ ID NO 21
<211> LENGTH: 116
<212> TYPE: PRT
<213> ORGANISM: Artificial Sequence
<220> FEATURE:
<223> OTHER INFORMATION: synthetic amino acid sequence

<400> SEQUENCE: 21

```
            Gln Val Gln Leu Gln Glu Ser Gly Pro Gly Leu Val Lys Pro Ser Glu
             1               5                  10                  15

Thr Leu Ser Leu Thr Cys Thr Val Ser Gly Gly Ser Ile Ser Ser Tyr
                            20                  25                  30

Tyr Trp Ser Trp Ile Arg Gln Pro Pro Gly Lys Gly Leu Glu Trp Ile
                        35                  40                  45

Gly Tyr Ile Ser Tyr Ser Gly Ser Thr Asn Tyr Asn Pro Ser Leu Lys
                    50                  55                  60

Ser Arg Val Thr Ile Ser Ala Asp Thr Ser Lys Asn Gln Phe Ser Leu
             65                 70                  75                  80

Lys Leu Ser Ser Val Thr Ala Ala Asp Thr Ala Val Tyr Tyr Cys Ala
                            85                  90                  95

Arg Asp Phe Tyr Tyr Gly Met Asp Val Trp Gly Gln Gly Thr Thr Val
                        100                 105                 110

Thr Val Ser Ser
                    115
```

<210> SEQ ID NO 22
<211> LENGTH: 106
<212> TYPE: PRT
<213> ORGANISM: Artificial Sequence
<220> FEATURE:
<223> OTHER INFORMATION: synthetic amino acid sequence

<400> SEQUENCE: 22

```
            Ala Ile Gln Leu Thr Gln Ser Pro Ser Ser Leu Ser Ala Ser Val Gly
             1               5                  10                  15

Asp Arg Val Thr Ile Thr Cys Arg Ala Ser Gln Gly Ile Ser Ser Ala
                            20                  25                  30

Leu Ala Trp Tyr Gln Gln Lys Pro Gly Lys Ala Pro Lys Leu Leu Ile
                        35                  40                  45

Tyr Asp Ala Ser Ser Leu Glu Ser Gly Val Pro Ser Arg Phe Ser Gly
                    50                  55                  60

Ser Gly Ser Gly Thr Asp Phe Thr Leu Thr Ile Ser Ser Leu Gln Pro
             65                 70                  75                  80
```

Glu Asp Phe Ala Thr Tyr Tyr Cys His Gln Phe Asp Tyr Tyr Pro Thr
                    85                  90                  95

Phe Gly Gly Gly Thr Lys Val Glu Ile Lys
            100                 105

<210> SEQ ID NO 23
<211> LENGTH: 124
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (124)..(124)
<223> OTHER INFORMATION: Xaa can be any naturally occurring amino acid

<400> SEQUENCE: 23

Glu Val Gln Leu Leu Glu Ser Gly Gly Ser Glu Gln Pro Gly Gly
1               5                   10                  15

Ser Leu Arg Leu Ser Cys Ala Ala Ser Gly Phe Thr Ser Ser Tyr
                20                  25                  30

Ala Met Ser Trp Val Arg Leu Ala Pro Gly Lys Gly Leu Glu Trp Val
            35                  40                  45

Ser Gly Ile Ser Gly Ser Gly Gly Thr Tyr Tyr Ala Asp Ser Val
        50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Gly Asp Tyr Tyr Gly Ser Gly Ser Tyr Pro Leu Phe Asp Tyr
            100                 105                 110

Trp Gly Gln Gly Thr Leu Val Thr Val Ser Ser Xaa
        115                 120

<210> SEQ ID NO 24
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Ser Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Pro
                85                  90                  95

Thr Phe Gly Pro Gly Thr Lys Val Asp Ile Lys
            100                 105

<210> SEQ ID NO 25
<211> LENGTH: 123
<212> TYPE: PRT

<210> SEQ ID NO 25
<211> LENGTH: 123
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (123)..(123)
<223> OTHER INFORMATION: Xaa can be any naturally occurring amino acid

<400> SEQUENCE: 25

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Ser
            20                  25                  30

Gly Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr His Tyr Asn Pro Ser
    50                  55                  60

Leu Lys Ser Arg Val Thr Ile Ser Val Asp Ser Ser Lys Ser Gln Phe
65                  70                  75                  80

Ser Leu Lys Leu Ser Ser Val Thr Ala Ala Asp Thr Ala Val Tyr Cys
                85                  90                  95

Cys Ala Arg His Lys Val Asp Ser Ser Gly Trp Pro Leu Asp Tyr Trp
            100                 105                 110

Gly Gln Gly Thr Leu Val Thr Val Ser Ser Xaa
        115                 120

<210> SEQ ID NO 26
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 26

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Cys Leu Ser Trp Tyr Gln Gln Lys Pro Gly Gln Ala Pro Arg Leu Leu
        35                  40                  45

Ile Tyr Asp Thr Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105

<210> SEQ ID NO 27
<211> LENGTH: 123
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (123)..(123)
<223> OTHER INFORMATION: Xaa can be any naturally occurring amino acid

<400> SEQUENCE: 27

-continued

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asn Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Asp Val Val Arg Tyr Phe Asp Trp Pro Leu Asp Tyr Trp
        100                 105                 110

Gly Gln Gly Thr Leu Val Thr Val Ser Ser Xaa
    115                 120

<210> SEQ ID NO 28
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 28

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
            85                  90                  95

Thr Phe Gly Gln Gly Thr Lys Val Glu Ile Lys
            100                 105

<210> SEQ ID NO 29
<211> LENGTH: 123
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (123)..(123)
<223> OTHER INFORMATION: Xaa can be any naturally occurring amino acid

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asn Gly Ser Asn Lys Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asp Asp Val Val Arg Tyr Phe Asp Trp Pro Leu Asp Tyr Trp
                   100                 105                 110

Gly Gln Gly Thr Leu Val Thr Val Ser Ser Xaa
            115                 120

<210> SEQ ID NO 30
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 30

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Val Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 31
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 31

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
 50                  55                  60

Ser Arg Ile Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Val Ile Leu Tyr Ser Ser Gly Trp Ser Phe Asp Tyr Trp Gly Gln
            100                 105                 110
```

```
Gly Thr Leu Val Thr Val Ser Ser Xaa
        115                 120

<210> SEQ ID NO 32
<211> LENGTH: 108
<212> TYPE: PRT
<213> ORGANISM: Artificial Sequence
<220> FEATURE:
<223> OTHER INFORMATION: synthetic amino acid sequence

<400> SEQUENCE: 32

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105

<210> SEQ ID NO 33
<211> LENGTH: 121
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (121)..(121)
<223> OTHER INFORMATION: Xaa can be any naturally occurring amino acid

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Ile Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Ile Leu Tyr Ser Ser Gly Trp Ser Phe Asp Tyr Trp Gly Gln
            100                 105                 110

Gly Thr Leu Val Thr Val Ser Ser Xaa
        115                 120

<210> SEQ ID NO 34
<211> LENGTH: 108
<212> TYPE: PRT
<213> ORGANISM: Artificial Sequence
<220> FEATURE:
```

<223> OTHER INFORMATION: synthetic amino acid sequence

<400> SEQUENCE: 34

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Asp Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105
```

<210> SEQ ID NO 35
<211> LENGTH: 124
<212> TYPE: PRT
<213> ORGANISM: Artificial Sequence
<220> FEATURE:
<223> OTHER INFORMATION: synthetic amino acid sequence
<220> FEATURE:
<221> NAME/KEY: misc_feature
<222> LOCATION: (124)..(124)
<223> OTHER INFORMATION: Xaa can be any naturally occurring amino acid

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Tyr Gly Ser Gly Ser Tyr Pro Leu Phe Asp Tyr
            100                 105                 110

Trp Gly Gln Gly Thr Leu Val Thr Val Ser Ser Xaa
        115                 120
```

<210> SEQ ID NO 36
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 36

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30
```

```
Leu Ala Trp Tyr Gln Gln Lys Pro Gly Lys Ala Pro Lys Leu Leu Ile
            35                  40                  45

Ser Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Phe Tyr Cys Gln Gln Phe Asn Asn Tyr Pro Pro
                 85                  90                  95

Thr Phe Gly Pro Gly Thr Lys Val Asp Ile Lys
            100                 105
```

<210> SEQ ID NO 37
<211> LENGTH: 123
<212> TYPE: PRT
<213> ORGANISM: Artificial Sequence
<220> FEATURE:
<223> OTHER INFORMATION: synthetic amino acid sequence

<400> SEQUENCE: 37

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Lys Trp Val
        35                  40                  45

Ser Gly Ile Ser Gly Ser Gly Gly Thr Tyr Tyr Ala Asp Ser Val
 50                  55                  60

Lys Gly Arg Phe Thr Leu Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Gly Asp Tyr Tyr Gly Ser Gly Ser Tyr Pro Leu Phe Asp Phe
            100                 105                 110

Trp Gly Gln Gly Thr Leu Val Thr Val Ser Ser
        115                 120
```

<210> SEQ ID NO 38
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 38

```
Ala Ile Gln Leu Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Phe Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Asp Tyr Pro Pro
                 85                  90                  95

Thr Phe Gly Pro Gly Thr Lys Leu Asp Ile Lys
            100                 105
```

<210> SEQ ID NO 39
<211> LENGTH: 116
<212> TYPE: PRT
<213> ORGANISM: Artificial Sequence
<220> FEATURE:
<223> OTHER INFORMATION: synthetic amino acid sequence

<400> SEQUENCE: 39

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Pro Gly Lys Gly Leu Glu Trp Ile
        35                  40                  45

Gly His Ile Ser Tyr Ser Gly Ser Thr His Tyr Asn Pro Ser Leu Lys
    50                  55                  60

Ser Arg Phe Thr Ile Ser Ala Asp Thr Ser Lys Asn Arg Phe Ser Leu
65                  70                  75                  80

Lys Leu Ser Ser Val Thr Ala Ala Asp Thr Ala Val Tyr Tyr Cys Ala
                85                  90                  95

Arg Asp Gly Tyr Tyr Ala Leu Asp Val Trp Gly Gln Gly Thr Thr Val
            100                 105                 110

Thr Val Ser Ser
            115
```

<210> SEQ ID NO 40
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 40

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Thr
            20                  25                  30

Val Ala Trp Tyr Gln Gln Asn Pro Gly Lys Ala Pro Lys Leu Leu Ile
        35                  40                  45

Tyr Asp Ala Ser Ser Leu Glu Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Tyr
                85                  90                  95

Thr Phe Gly Gln Gly Thr Lys Leu Glu Ile Lys
            100                 105
```

<210> SEQ ID NO 41
<211> LENGTH: 123
<212> TYPE: PRT
<213> ORGANISM: Artificial Sequence
<220> FEATURE:
<223> OTHER INFORMATION: synthetic amino acid sequence

<400> SEQUENCE: 41

```
Glu Val Gln Leu Leu Glu Ser Gly Gly Gly Leu Glu Gln Pro Gly Gly
1               5                   10                  15
```

```
Ser Leu Arg Leu Ser Cys Ala Ala Ser Gly Phe Thr Ser Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Thr Tyr Tyr Ala Asp Ser Val
50                  55                  60

Lys Gly Arg Phe Ser Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Tyr Gly Ser Gly Ser Tyr Pro Leu Phe Asp Tyr
            100                 105                 110

Trp Gly Gln Gly Thr Leu Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: synthetic amino acid sequence

<400> SEQUENCE: 42

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Pro Lys Leu Leu Ile
        35                  40                  45

Ser Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Pro
                85                  90                  95

Thr Phe Gly Pro Gly Thr Lys Val Asp Ile Lys
            100                 105

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000
```

```
<210> SEQ ID NO 47
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 47

Gly Phe Thr Ser Ser Gly Tyr Ala
1               5

<210> SEQ ID NO 48
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 48

Ile Ser Gly Ser Gly Gly Gly Thr
1               5

<210> SEQ ID NO 49
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 49

Ala Lys Gly Asp Tyr Tyr Gly Ser Gly Ser Tyr Pro Leu Phe Asp Tyr
1               5                   10                  15

<210> SEQ ID NO 50
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 50

Gln Gly Ile Ser Ser Ala
1               5

<210> SEQ ID NO 51

<400> SEQUENCE: 51

000

<210> SEQ ID NO 52
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 52

Gln Gln Phe Asn Asn Tyr Pro Pro Thr
1               5

<210> SEQ ID NO 53
<211> LENGTH: 8
<212> TYPE: PRT
<213> ORGANISM: Artificial Sequence
<220> FEATURE:
```

<223> OTHER INFORMATION: synthetic amino acid sequence

<400> SEQUENCE: 53

Gly Gly Ser Ile Ser Ser Tyr Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 54

Ile Tyr Tyr Ser Gly Thr Thr
1               5

<210> SEQ ID NO 55
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 55

Ala Arg Val Val Leu Tyr Ser Thr Gly Trp Ser Phe Asp Tyr
1               5                   10

<210> SEQ ID NO 56
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 56

Gln Ser Val Ser Ser Ser Tyr
1               5

<210> SEQ ID NO 57

<400> SEQUENCE: 57

000

<210> SEQ ID NO 58
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 58

Gln Gln Asp Tyr Asn Leu Pro Leu Thr
1               5

<210> SEQ ID NO 59
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 59

Gly Gly Ser Ile Ser Ser Tyr Tyr
1               5

```
<210> SEQ ID NO 60
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 60

Ile Tyr Tyr Ser Gly Ser Thr
1               5

<210> SEQ ID NO 61
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 61

Ala Arg Val Val Leu Tyr Ser Ser Gly Trp Ser Phe Asp Tyr
1               5                   10

<210> SEQ ID NO 62
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 62

Gln Ser Phe Ser Ser Ser Tyr
1               5

<210> SEQ ID NO 63

<400> SEQUENCE: 63

000

<210> SEQ ID NO 64
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 64

Gln Gln Asp Tyr Asn Leu Pro Leu Thr
1               5

<210> SEQ ID NO 65
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 65

Gly Gly Ser Ile Ser His Tyr Tyr
1               5

<210> SEQ ID NO 66
<211> LENGTH: 7
<212> TYPE: PRT
<213> ORGANISM: Artificial Sequence
<220> FEATURE:
<223> OTHER INFORMATION: synthetic amino acid sequence
```

```
<400> SEQUENCE: 66

Ile Tyr Tyr Ser Gly Ser Thr
1               5

<210> SEQ ID NO 67
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 67

Ala Arg Val Val Leu Tyr Ser Ser Gly Trp Ser Phe Asp Tyr
1               5                   10

<210> SEQ ID NO 68
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 68

Gln Ser Val Ser Ser Ser Tyr
1               5

<210> SEQ ID NO 69

<400> SEQUENCE: 69

000

<210> SEQ ID NO 70
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 70

Gln Gln Asp Tyr Asn Leu Pro Leu Thr
1               5

<210> SEQ ID NO 71
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 71

Gly Gly Ser Ile Ser Ser Tyr Tyr
1               5

<210> SEQ ID NO 72
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 72

Ile Tyr Tyr Ser Gly Ser Thr
1               5
```

```
<210> SEQ ID NO 73
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 73

Ala Arg Val Met Val Phe Ser Ser Gly Trp Tyr Phe Asp Tyr
1               5                   10

<210> SEQ ID NO 74
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 74

Gln Asn Ile Thr Ser Ser Tyr
1               5

<210> SEQ ID NO 75

<400> SEQUENCE: 75

000

<210> SEQ ID NO 76
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 76

Gln Gln Asp Tyr Asn Leu Pro Leu Thr
1               5

<210> SEQ ID NO 77
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 77

Gly Gly Ser Ile Ser Ser His Tyr
1               5

<210> SEQ ID NO 78
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 78

Ile Tyr Tyr Ser Gly Asn Thr
1               5

<210> SEQ ID NO 79
<211> LENGTH: 17
<212> TYPE: PRT
<213> ORGANISM: Artificial Sequence
<220> FEATURE:
<223> OTHER INFORMATION: synthetic amino acid sequence
```

```
<400> SEQUENCE: 79

Ala Arg Val Gly Pro Gly Ser His Tyr Asn Pro His Asn Trp Phe Asp
1               5                   10                  15

Pro

<210> SEQ ID NO 80
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 80

Gln Thr Val Thr Ser Ser Tyr
1               5

<210> SEQ ID NO 81

<400> SEQUENCE: 81

000

<210> SEQ ID NO 82
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 82

Gln Gln Asp Tyr Asn Leu Pro Trp Thr
1               5

<210> SEQ ID NO 83
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 83

Gly Tyr Thr Phe Thr Asn Tyr Gly
1               5

<210> SEQ ID NO 84
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 84

Ile Ser Ala Tyr Asn Gly Asn Thr
1               5

<210> SEQ ID NO 85
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 85

Ala Arg Asp Tyr Tyr Ser Ser Gly Ser Tyr Gly Gly Trp Phe Asp Pro
1               5                   10                  15
```

```
<210> SEQ ID NO 86
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 86

Ser Gly His Ser Ser Tyr Ala
1               5

<210> SEQ ID NO 87
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 87

Leu Asn Ser Asp Gly Ser His
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 88

Gln Thr Trp Gly Thr Gly Ile Arg Val
1               5

<210> SEQ ID NO 89
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 89

Gly Tyr Thr Phe Thr Asn Tyr Gly
1               5

<210> SEQ ID NO 90
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 90

Ile Ser Ala Tyr Asn Gly Asn Thr
1               5

<210> SEQ ID NO 91
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 91

Ala Arg Asp Tyr Tyr Ser Ser Gly Ser Tyr Gly Gly Trp Phe Asp Pro
1               5                   10                  15
```

-continued

```
<210> SEQ ID NO 92
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 92

Ser Gly His Ser Ser Tyr Ala
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 93

Leu Asn Ser Asp Gly Ser His
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 94

Gln Thr Trp Gly Thr Gly Ile Arg Val
1               5

<210> SEQ ID NO 95
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 95

Gly Phe Thr Ser Ser Ser Tyr Ala
1               5

<210> SEQ ID NO 96
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 96

Ile Ser Gly Ser Gly Asp Ser Thr
1               5

<210> SEQ ID NO 97
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 97

Ala Lys Gly Asp Tyr Tyr Gly Ser Gly Ser Tyr Pro Leu Phe Asp Tyr
1               5                   10                  15

<210> SEQ ID NO 98
```

```
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 98

Gln Gly Ile Ser Ser Ala
1               5

<210> SEQ ID NO 99

<400> SEQUENCE: 99

000

<210> SEQ ID NO 100
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 100

Gln Gln Phe Tyr Asn Tyr Pro Pro Thr
1               5

<210> SEQ ID NO 101
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 101

Gly Gly Ser Ile Ser Tyr Tyr Tyr
1               5

<210> SEQ ID NO 102
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 102

Ile Tyr Tyr Ser Gly Ser Thr
1               5

<210> SEQ ID NO 103
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 103

Ala Arg Ile Arg Gly Asp Ser Tyr Gly Trp Asp Phe Asp Tyr
1               5                   10

<210> SEQ ID NO 104
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 104
```

```
Gln Ser Ile Ser Asn Asn Tyr
1               5

<210> SEQ ID NO 105

<400> SEQUENCE: 105

000

<210> SEQ ID NO 106
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 106

Gln Gln Asp Tyr Asn Phe Pro Leu Thr
1               5

<210> SEQ ID NO 107
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 107

Gly Gly Ser Ile Ser Ser Tyr Tyr
1               5

<210> SEQ ID NO 108
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 108

Ile Ser Tyr Ser Gly Ser Thr
1               5

<210> SEQ ID NO 109
<211> LENGTH: 10
<212> TYPE: PRT
<213> ORGANISM: Artificial Sequence
<220> FEATURE:
<223> OTHER INFORMATION: synthetic amino acid sequence

<400> SEQUENCE: 109

Ala Arg Asp Phe Tyr Tyr Gly Met Asp Val
1               5                   10

<210> SEQ ID NO 110
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 110

Gln Gly Ile Ser Ser Ala
1               5

<210> SEQ ID NO 111
```

```
<400> SEQUENCE: 111

000

<210> SEQ ID NO 112
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 112

His Gln Phe Asp Tyr Tyr Pro Thr
1               5

<210> SEQ ID NO 113
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 113

Gly Phe Thr Ser Ser Ser Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 114

Ile Ser Gly Ser Gly Gly Gly Thr
1               5

<210> SEQ ID NO 115
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 115

Thr Lys Gly Asp Tyr Tyr Gly Ser Gly Ser Tyr Pro Leu Phe Asp Tyr
1               5                   10                  15

<210> SEQ ID NO 116
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 116

Gln Gly Ile Ser Ser Ala
1               5

<210> SEQ ID NO 117

<400> SEQUENCE: 117

000

<210> SEQ ID NO 118
<211> LENGTH: 9
```

```
<212> TYPE: PRT
<213> ORGANISM: Artificial Sequence
<220> FEATURE:
<223> OTHER INFORMATION: synthetic amino acid sequence

<400> SEQUENCE: 118

Gln Gln Phe Asn Asn Tyr Pro Pro Thr
1               5

<210> SEQ ID NO 119
<211> LENGTH: 10
<212> TYPE: PRT
<213> ORGANISM: Artificial Sequence
<220> FEATURE:
<223> OTHER INFORMATION: synthetic amino acid sequence

<400> SEQUENCE: 119

Gly Asp Ser Ile Ser Ser Ser Gly Tyr Tyr
1               5                   10

<210> SEQ ID NO 120
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 120

Ile Tyr Tyr Ser Gly Ser Thr
1               5

<210> SEQ ID NO 121
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 121

Ala Arg His Lys Val Asp Ser Ser Gly Trp Pro Leu Asp Tyr
1               5                   10

<210> SEQ ID NO 122
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 122

Gln Ser Ile Ser Ser Ser Cys
1               5

<210> SEQ ID NO 123

<400> SEQUENCE: 123

000

<210> SEQ ID NO 124
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 124
```

```
Gln Gln Asp Tyr Asn Leu Pro Leu Thr
1               5

<210> SEQ ID NO 125
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 125

Gly Phe Thr Phe Ser Ser Tyr Gly
1               5

<210> SEQ ID NO 126
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 126

Ile Trp Tyr Asn Gly Ser Asn Arg
1               5

<210> SEQ ID NO 127
<211> LENGTH: 15
<212> TYPE: PRT
<213> ORGANISM: Artificial Sequence
<220> FEATURE:
<223> OTHER INFORMATION: synthetic amino acid sequence

<400> SEQUENCE: 127

Ala Arg Asp Asp Val Val Arg Tyr Phe Asp Trp Pro Leu Asp Tyr
1               5                   10                  15

<210> SEQ ID NO 128
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 128

Gln Gly Ile Arg Asn Asp
1               5

<210> SEQ ID NO 129

<400> SEQUENCE: 129

000

<210> SEQ ID NO 130
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 130

Leu Gln Asp Tyr Asn Tyr Pro Trp Thr
1               5

<210> SEQ ID NO 131
<211> LENGTH: 8
<212> TYPE: PRT
```

```
<213> ORGANISM: Artificial Sequence
<220> FEATURE:
<223> OTHER INFORMATION: synthetic amino acid sequence

<400> SEQUENCE: 131

Gly Phe Thr Phe Ser Asn Tyr Gly
1               5

<210> SEQ ID NO 132
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 132

Ile Trp Tyr Asn Gly Ser Asn Lys
1               5

<210> SEQ ID NO 133
<211> LENGTH: 15
<212> TYPE: PRT
<213> ORGANISM: Artificial Sequence
<220> FEATURE:
<223> OTHER INFORMATION: synthetic amino acid sequence

<400> SEQUENCE: 133

Ala Arg Asp Asp Val Val Arg Tyr Phe Asp Trp Pro Leu Asp Tyr
1               5                   10                  15

<210> SEQ ID NO 134
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 134

Gln Gly Ile Arg Asn Asp
1               5

<210> SEQ ID NO 135

<400> SEQUENCE: 135

000

<210> SEQ ID NO 136
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 136

Leu Gln Asp Tyr Asn Tyr Pro Trp Thr
1               5

<210> SEQ ID NO 137
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 137

Gly Gly Ser Ile Ser Ser Tyr Tyr
```

```
<210> SEQ ID NO 138
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 138

Ile Tyr Tyr Ser Gly Ser Thr
1               5

<210> SEQ ID NO 139
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 139

Ala Arg Val Ile Leu Tyr Ser Ser Gly Trp Ser Phe Asp Tyr
1               5                   10

<210> SEQ ID NO 140
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 140

Gln Ser Val Ser Ser Ser Tyr
1               5

<210> SEQ ID NO 141

<400> SEQUENCE: 141

000

<210> SEQ ID NO 142
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 142

Gln Gln Asp Tyr Asn Leu Pro Leu Thr
1               5

<210> SEQ ID NO 143
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 143

Gly Gly Ser Ile Ser Ser Tyr Tyr
1               5

<210> SEQ ID NO 144
<211> LENGTH: 7
<212> TYPE: PRT
<213> ORGANISM: Artificial Sequence
```

```
<220> FEATURE:
<223> OTHER INFORMATION: synthetic amino acid sequence

<400> SEQUENCE: 144

Ile Tyr Tyr Ser Gly Ser Thr
1               5

<210> SEQ ID NO 145
<211> LENGTH: 14
<212> TYPE: PRT
<213> ORGANISM: Artificial Sequence
<220> FEATURE:
<223> OTHER INFORMATION: synthetic amino acid sequence

<400> SEQUENCE: 145

Ala Arg Val Ile Leu Tyr Ser Ser Gly Trp Ser Phe Asp Tyr
1               5                   10

<210> SEQ ID NO 146
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 146

Gln Ser Val Ser Ser Ser Tyr
1               5

<210> SEQ ID NO 147

<400> SEQUENCE: 147

000

<210> SEQ ID NO 148
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 148

Gln Gln Asp Tyr Asn Leu Pro Leu Thr
1               5

<210> SEQ ID NO 149
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 149

Gly Phe Thr Ser Ser Ser Tyr Gly
1               5

<210> SEQ ID NO 150
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 150

Ile Ser Gly Ser Gly Gly Gly Thr
1               5
```

```
<210> SEQ ID NO 151
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 151

Ala Lys Gly Asp Tyr Tyr Gly Ser Gly Ser Tyr Pro Leu Phe Asp Tyr
1               5                   10                  15

<210> SEQ ID NO 152
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 152

Gln Asp Ile Ser Ser Ala
1               5

<210> SEQ ID NO 153

<400> SEQUENCE: 153

000

<210> SEQ ID NO 154
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 154

Gln Gln Phe Asn Asn Tyr Pro Pro Thr
1               5

<210> SEQ ID NO 155
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 155

Gly Phe Thr Phe Ser Ser Tyr Ala
1               5

<210> SEQ ID NO 156
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 156

Ile Ser Gly Ser Gly Gly Gly Thr
1               5

<210> SEQ ID NO 157
<211> LENGTH: 16
<212> TYPE: PRT
<213> ORGANISM: Artificial Sequence
<220> FEATURE:
```

<223> OTHER INFORMATION: synthetic amino acid sequence

<400> SEQUENCE: 157

Ala Lys Gly Asp Tyr Tyr Gly Ser Gly Ser Tyr Pro Leu Phe Asp Phe
1               5                   10                  15

<210> SEQ ID NO 158
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 158

Gln Gly Ile Ser Ser Ala
1               5

<210> SEQ ID NO 159

<400> SEQUENCE: 159

000

<210> SEQ ID NO 160
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 160

Gln Gln Phe Asn Asp Tyr Pro Pro Thr
1               5

<210> SEQ ID NO 161
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 161

Gly Gly Ser Ile Ser Ser Tyr Tyr
1               5

<210> SEQ ID NO 162
<211> LENGTH: 7
<212> TYPE: PRT
<213> ORGANISM: Artificial Sequence
<220> FEATURE:
<223> OTHER INFORMATION: synthetic amino acid sequence

<400> SEQUENCE: 162

Ile Ser Tyr Ser Gly Ser Thr
1               5

<210> SEQ ID NO 163
<211> LENGTH: 10
<212> TYPE: PRT
<213> ORGANISM: Artificial Sequence
<220> FEATURE:
<223> OTHER INFORMATION: synthetic amino acid sequence

<400> SEQUENCE: 163

Ala Arg Asp Gly Tyr Tyr Ala Leu Asp Val
1               5                   10

```
<210> SEQ ID NO 164
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 164

Gln Asp Ile Ser Asn Thr
1               5

<210> SEQ ID NO 165

<400> SEQUENCE: 165

000

<210> SEQ ID NO 166
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 166

Gln Gln Phe Asn Asn Tyr Pro Tyr Thr
1               5

<210> SEQ ID NO 167
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 167

Gly Phe Thr Ser Ser Ser Tyr Ala
1               5

<210> SEQ ID NO 168
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 168

Ile Ser Gly Ser Gly Gly Gly Thr
1               5

<210> SEQ ID NO 169
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 169

Ala Lys Gly Asp Tyr Tyr Gly Ser Gly Ser Tyr Pro Leu Phe Asp Tyr
1               5                   10                  15

<210> SEQ ID NO 170
<211> LENGTH: 6
<212> TYPE: PRT
<213> ORGANISM: Artificial Sequence
<220> FEATURE:
<223> OTHER INFORMATION: synthetic amino acid sequence
```

<400> SEQUENCE: 170

Gln Gly Ile Ser Ser Ala
1               5

<210> SEQ ID NO 171

<400> SEQUENCE: 171

000

<210> SEQ ID NO 172
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 172

Gln Gln Phe Asn Asn Tyr Pro Pro Thr
1               5

<210> SEQ ID NO 173
<211> LENGTH: 370
<212> TYPE: DNA
<213> ORGANISM: Artificial Sequence
<220> FEATURE:
<223> OTHER INFORMATION: synthetic nucleic acid sequence

<400> SEQUENCE: 173
gaggtgcagt tgttggagtc tgggggaggc ttggtacagc ctggggggtc cctgagactc      60
tcctgtgcag cctctggatt cacctctagc ggctatgcca tgagctgggt ccgccaggct     120
ccagggaagg gctggagtg gtctcaggt attagtggta gtggtggtgg cacatactac      180
gcagactccg tgaagggccg gttcaccatc tccagagaca attccaagaa cacactgtat     240
ctgcaaatga acaacctgag agccgaggac acggccgtat attactgtgc gaaaggggat     300
tactatggtt cggggagtta ccgcttttt gactactggg gccagggaac cctggtcatc      360
gtctcctcag                                                            370

<210> SEQ ID NO 174
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 174
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctctgat gcctccagtt tggaaagtgg ggtcccatca     180
aggttcagcg gcagtggatc tgggacagat ttcactctca ccatcagcag cctgcaacct     240
gaagattttg caacttttta ctgtcaacag tttaataatt accctcccac tttcggccct     300
gggaccaaag tggatatcaa a                                               321

<210> SEQ ID NO 175
<211> LENGTH: 361
<212> TYPE: DNA
<213> ORGANISM: Artificial Sequence
<220> FEATURE:
<223> OTHER INFORMATION: synthetic nucleic acid sequence

<400> SEQUENCE: 175

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggaccac caactacaac     180
ccctccctca agagtcgagt caccatatca gtagacacgt ccaagaacca gttctccctg     240
aagctgagct ctgtgaccgc tgcggacacg gccgtgtatt actgtgcgag agtagtcctg     300
tatagcactg ctggtccttc gactactggg gccagggaa ccctggtcac cgtctcctca     360
g                                                                   361
```

<210> SEQ ID NO 176
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 176

```
gaaattgtaa tgacacagtc tccagccacc ctgtctttgt ctccagggga aagagccacc      60
ctctcctgca gggccagtca gagtgttagc agcagctact tatcctggta ccagcagaga     120
cctgggcagg ctcccaggct cctcatctat ggtacgtcca ccaggccac tggcatccca     180
gccaggttca gtggcagtgg gtctgggaca gacttcactc tcaccatcag cagcctgcag     240
cctgaagatt ttgcagttta ttactgtcag caggattata acttaccgct cactttcggc     300
ggagggacca aggtggagat caaa                                           324
```

<210> SEQ ID NO 177
<211> LENGTH: 361
<212> TYPE: DNA
<213> ORGANISM: Artificial Sequence
<220> FEATURE:
<223> OTHER INFORMATION: synthetic nucleic acid sequence

<400> SEQUENCE: 177

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agtagtcctg     300
tatagcagtg ctggtccttc gactactggg gccagggaa ccctggtcac cgtctcctca     360
g                                                                   361
```

<210> SEQ ID NO 178
<211> LENGTH: 324
<212> TYPE: PRT
<213> ORGANISM: Artificial Sequence
<220> FEATURE:
<223> OTHER INFORMATION: synthetic nucleic acid sequence

<400> SEQUENCE: 178

```
Gly Ala Ala Ala Thr Thr Gly Thr Ala Ala Thr Gly Ala Cys Ala Cys
1               5                   10                  15
Ala Gly Thr Cys Thr Cys Cys Ala Gly Cys Cys Ala Cys Cys Cys Thr
            20                  25                  30
```

Gly Thr Cys Thr Thr Thr Gly Thr Cys Thr Cys Cys Ala Gly Gly Gly
                 35                  40                  45

Gly Ala Ala Ala Gly Ala Gly Cys Cys Ala Cys Cys Thr Cys Thr
     50                  55                  60

Cys Cys Thr Gly Cys Ala Gly Gly Cys Cys Ala Gly Thr Cys Ala
 65              70                  75                      80

Gly Ala Gly Thr Thr Thr Ala Gly Cys Ala Gly Cys Ala Gly Cys
                 85                  90                  95

Thr Ala Cys Thr Thr Ala Thr Cys Cys Thr Gly Gly Thr Ala Cys Cys
                 100                 105                 110

Ala Gly Cys Ala Gly Ala Ala Ala Cys Cys Thr Gly Gly Cys Ala
                 115                 120                 125

Gly Gly Cys Thr Cys Cys Cys Ala Gly Gly Cys Thr Cys Thr Cys
         130                 135                 140

Ala Thr Cys Thr Ala Thr Gly Gly Thr Gly Cys Ala Thr Cys Cys Ala
 145                 150                 155                     160

Cys Cys Ala Gly Gly Gly Cys Cys Ala Cys Thr Gly Gly Cys Ala Thr
                 165                 170                 175

Cys Cys Cys Ala Gly Cys Ala Gly Gly Thr Thr Cys Ala Gly Thr
             180                 185                 190

Gly Gly Cys Ala Gly Thr Gly Gly Gly Thr Cys Thr Gly Gly Gly Ala
             195                 200                 205

Cys Ala Gly Ala Cys Thr Thr Cys Ala Cys Thr Cys Thr Ala Cys
     210                 215                 220

Cys Ala Thr Cys Ala Gly Cys Ala Gly Cys Cys Thr Gly Cys Ala Gly
225                  230                 235                     240

Cys Cys Thr Gly Ala Ala Gly Ala Thr Thr Thr Thr Gly Cys Ala Gly
                 245                 250                 255

Thr Thr Thr Ala Thr Thr Ala Cys Thr Gly Thr Cys Ala Gly Cys Ala
                 260                 265                 270

Gly Gly Ala Thr Thr Ala Thr Ala Ala Cys Thr Ala Cys Cys Gly
             275                 280                 285

Cys Thr Cys Ala Cys Thr Thr Thr Cys Gly Gly Cys Gly Gly Ala Gly
                 290                 295                 300

Gly Gly Ala Cys Cys Ala Ala Gly Gly Thr Gly Gly Ala Gly Ala Thr
305                  310                 315                     320

Cys

<210> SEQ ID NO 180
<211> LENGTH: 324
<212> TYPE: PRT
<213> ORGANISM: Artificial Sequence
<220> FEATURE:
<223> OTHER INFORMATION: synthetic nucleic acid sequence

<400> SEQUENCE: 180

Gly Ala Ala Ala Thr Gly Thr Ala Ala Thr Gly Ala Cys Ala Cys
1               5                   10                  15

Ala Gly Thr Cys Thr Cys Cys Ala Gly Cys Cys Ala Cys Cys Thr
                20                  25                  30

Gly Thr Cys Thr Thr Thr Gly Thr Cys Cys Ala Gly Gly Gly
            35                  40                  45

Gly Ala Ala Ala Gly Ala Gly Cys Cys Ala Cys Cys Thr Cys Thr
    50                  55                  60

Cys Cys Thr Gly Cys Ala Gly Gly Cys Cys Ala Gly Thr Cys Ala
65                  70                  75                  80

Gly Ala Gly Thr Gly Thr Thr Ala Gly Cys Ala Gly Cys Ala Gly
                85                  90                  95

Thr Ala Cys Thr Thr Ala Thr Cys Cys Thr Gly Gly Thr Ala Cys Cys
                100                 105                 110

Ala Gly Cys Ala Gly Ala Ala Cys Cys Thr Gly Gly Cys Ala
            115                 120                 125

Gly Gly Cys Thr Cys Cys Cys Ala Gly Gly Cys Thr Cys Cys Thr Cys
        130                 135                 140

Ala Thr Cys Thr Ala Thr Gly Gly Thr Gly Cys Ala Thr Cys Cys Ala
145                 150                 155                 160

Cys Cys Ala Gly Gly Gly Cys Cys Ala Cys Thr Gly Gly Cys Ala Thr
                165                 170                 175

Cys Cys Cys Ala Gly Cys Cys Ala Gly Gly Thr Thr Cys Ala Gly Thr
            180                 185                 190

Gly Gly Cys Ala Gly Thr Gly Gly Gly Thr Cys Thr Gly Gly Gly Ala
        195                 200                 205

Cys Ala Gly Ala Cys Thr Thr Cys Ala Cys Thr Cys Thr Cys Ala Cys
    210                 215                 220

Cys Ala Thr Cys Ala Gly Cys Ala Gly Cys Cys Thr Gly Cys Ala Gly
225                 230                 235                 240

Cys Cys Thr Gly Ala Ala Gly Ala Thr Thr Thr Thr Gly Cys Ala Gly
                245                 250                 255

Thr Thr Thr Ala Thr Thr Ala Cys Thr Gly Thr Cys Ala Gly Cys Ala
            260                 265                 270

Gly Gly Ala Thr Thr Ala Thr Ala Cys Thr Thr Ala Cys Cys Gly
        275                 280                 285

Cys Thr Cys Ala Cys Thr Thr Thr Cys Gly Gly Cys Gly Gly Ala Gly
    290                 295                 300

Gly Gly Ala Cys Cys Ala Ala Gly Gly Thr Gly Gly Ala Gly Ala Thr
305                 310                 315                 320

Cys Ala Ala Ala

<210> SEQ ID NO 181
<211> LENGTH: 361
<212> TYPE: DNA
<213> ORGANISM: Artificial Sequence
<220> FEATURE:

<223> OTHER INFORMATION: synthetic nucleic acid sequence

<400> SEQUENCE: 181

| caggtgcagc tgcaggagtc gggcccagga ctggtgaagc cttcggagac cctgtccctc | 60 |
| acctgcactg tctctggtgg ctccatcagt agttactact ggagctggat ccggcagccc | 120 |
| ccagggaagg gactggagtg gattgggtat atctattaca gtgggagcac caactacaac | 180 |
| ccctccctca gagtcgagt caccatatca gttgacacgt ccaagaacca gttctccctg | 240 |
| aagctgagct ctgtgaccgc tgcggacacg gccgtgtatt actgtgcgag agtaatggtg | 300 |
| tttagcagtg gctggtactt tgactactgg ggccagggaa ccctggtcac cgtctcctca | 360 |
| g | 361 |

<210> SEQ ID NO 182
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 182

| gaaattgtaa tgacacagtc tccagccacc ctgtctttgt ctccagggga aagagccacc | 60 |
| ctctcctgca gggccagtca aatattacc agcagctact tatcctggta ccagcagaaa | 120 |
| cctgggcagt ctcccaggct cctcatttat gatgcatcca ccagggccac tggcatccca | 180 |
| gccaggttca gtggcagtgg gtctgggaca gacttcactc tcaccatcag cagcctgcag | 240 |
| cctgaagatt ttgcagttta ttactgtcag caggattata acttaccgct cactttcggc | 300 |
| ggagggacca aggtggagat caaa | 324 |

<210> SEQ ID NO 183
<211> LENGTH: 370
<212> TYPE: DNA
<213> ORGANISM: Artificial Sequence
<220> FEATURE:
<223> OTHER INFORMATION: synthetic nucleic acid sequence

<400> SEQUENCE: 183

| caggtgcagc tgcaggagtc gggcccagga ctggtgaagc cttcggagac cctgtccctc | 60 |
| acctgcactg tctctggtgg ctccatcagt agtcactact ggagctggat ccggcagccc | 120 |
| ccagggaagg gactggagtg gattgggtat atctattaca gtgggaatac caagtacaac | 180 |
| ccctccctca gagtcgagt caccatttca gtcgacacgt ccaagaacca gttctccctg | 240 |
| aagctgacct ctgtgaccgc tgcggacacg gccgtgtatt actgtgcgag agtgggcccg | 300 |
| gggagtcatt ataaccctca caactggttc gaccctggg gccagggaac cctggtcacc | 360 |
| gtctcctcag | 370 |

<210> SEQ ID NO 184
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 184

| gaaattgtaa tgacacagtc tccagccacc ctgtctttgt ctccagggga aagagccacc | 60 |
| ctctcctgca gggccagtca gactgttacc agcagctact tatcctggta ccagcagaaa | 120 |
| cctgggcagg ctcccaggct cctcatctat ggtgcatcca ccagggccac tggcttccca | 180 |

```
gccaggttca gtgtcagtgg gtctgggaca gacttcactc tcaccatcag cagcctgcag    240
cctgaagatt ttgcagttta ttactgtcag caggattata acttaccgtg acgttcggc    300 caagggacca aggtggaaat caaa                                           324
```

```
<210> SEQ ID NO 185
<211> LENGTH: 370
<212> TYPE: DNA
<213> ORGANISM: Artificial Sequence
<220> FEATURE:
<223> OTHER INFORMATION: synthetic nucleic acid sequence

<400> SEQUENCE: 185
caggttcagc tggtgcagtc tggagctgag gtgaagaagc ctggggcctc agtgaaggtc    60
tcctgcaagg cttctggtta cacctttacc aactatggta tcatctgggt gcgacaggcc   120
cctggacaag gcttgagtg atgggatgg atcagcgctt acaatggtaa cacaaactat    180
gcacagaagc tccagggcag agtcaccatg accacagaca catccacgag cacagcctac   240
atggagctga ggaccctgag atctgacgac acggccgtgt attactgtgc gagagattac   300
tatagttcgg ggagttatgg gggctggttc gaccccctggg ccagggaac cctggtcacc   360 gtctcctcag                                                           370
```

```
<210> SEQ ID NO 186
<211> LENGTH: 333
<212> TYPE: DNA
<213> ORGANISM: Artificial Sequence
<220> FEATURE:
<223> OTHER INFORMATION: synthetic nucleic acid sequence

<400> SEQUENCE: 186
cagcttgtgc tgactcaatc gccctctgcc tctgcctccc tgggagcctc ggtcaagctc    60
acctgcactc tgagcagtgg gcacagcagc tacgccatcg catggcatca gcagcagcca   120
gagaagggcc ctcggtactt gatgaagctt aacagtgatg gcagccacag caaggggac    180 gggatccctg atcgcttctc aggctccagc tctggggctg agcgctacct caccatctcc   240
agcctccagt ctgtggatga ggctgactat tactgtcaga cctggggcac tggcattcgg   300
gtgttcggtg gaggaaccaa actgactgtc cta                                 333
```

```
<210> SEQ ID NO 187
<211> LENGTH: 368
<212> TYPE: DNA
<213> ORGANISM: Artificial Sequence
<220> FEATURE:
<223> OTHER INFORMATION: synthetic nucleic acid sequence

<400> SEQUENCE: 187
caggttcagc tggtgcagtc tggagctgag gtgaagaagc ctggggcctc agtgaaggtc    60
tcctgcaagg cttctggtta cacctttacc aactatggta tcatctgggt gcgacaggcc   120
cctggacaag gcttgagtg atgggatgg atcagcgctt acaatggtaa cacaaactat    180
gcacagaagc tccagggcag agtcaccatg accacagaca catccacgag cacagcctac   240
atggagctga ggagcctgag atctgacgac acggccgtgt attactgtgc gagagattac   300
tatagttcgg ggagttatgg gggctggttc gaccccctggg ccagggaac cctggtcacc   360 gtctcctc                                                             368
```

```
<210> SEQ ID NO 188
```

<211> LENGTH: 333
<212> TYPE: DNA
<213> ORGANISM: Artificial Sequence
<220> FEATURE:
<223> OTHER INFORMATION: synthetic nucleic acid sequence

<400> SEQUENCE: 188

| | | | | | |
|---|---|---|---|---|---|
| cagcttgtgc | tgactcaatc | gccctctgcc | tctgcctccc | tgggagcctc | ggtcaagctc | 60 |
| acctgcactc | tgagcagtgg | gcacagcagc | tacgccatcg | catggcatca | gcagcagcca | 120 |
| gagaagggcc | ctcggtactt | gatgaagctt | aacagtgatg | gcagccacag | caaggggac | 180 |
| gggatccctg | atcgcttctc | aggctccagc | tctggggctg | agcgctacct | caccatctcc | 240 |
| agcctccagt | ctgtggatga | ggctgactat | tactgtcaga | cctggggcac | tggcattcgg | 300 |
| gtgttcggtg | aggaaccaa | actgactgtc | cta | | | 333 |

<210> SEQ ID NO 189
<211> LENGTH: 370
<212> TYPE: DNA
<213> ORGANISM: Artificial Sequence
<220> FEATURE:
<223> OTHER INFORMATION: synthetic nucleic acid sequence

<400> SEQUENCE: 189

| | | | | | |
|---|---|---|---|---|---|
| gaggtgcagc | tgttggagtc | tgggggaggc | ttggtacagc | cggggggtc | cctgagactc | 60 |
| tcctgtgcag | cctctggatt | cacgtctagt | agctatgcca | tgagctgggt | ccgccaggct | 120 |
| ccagggaagg | ggctggagtg | ggtctcaggt | attagtggta | gtggtgatag | tacatattac | 180 |
| gcagactccg | tgaagggccg | gttcattatt | tccagagaca | attccaagaa | cacgctgtat | 240 |
| ctgcaaatga | acagcctgag | agccgaggac | acggccgtat | attactgtgc | gaaaggggat | 300 |
| tactatggtt | cggggagtta | tcccctttt | gactactggg | gacagggaac | ccgggtcacc | 360 |
| gtctcctcag | | | | | | 370 |

<210> SEQ ID NO 190
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 190

| | | | | | |
|---|---|---|---|---|---|
| gccatccagt | tgacccagtc | tccatcctcc | ctgtctgcat | ctgtaggaga | cagagtcacc | 60 |
| atcacttgcc | gggcaagtca | gggcattagc | agtgctttag | cctggtatca | gcaaaaacca | 120 |
| gggaaagctc | ctaagctcct | gatctctgat | gcctccagtt | tggaaagtgg | ggtcccatca | 180 |
| aggttcagcg | gcggtggatc | tgggacagat | ttcactctca | ccatcagcag | cctgcagcct | 240 |
| gaagattttg | ctacttatta | ctgtcaacag | ttttataatt | accctccac | tttcggccct | 300 |
| gggaccaaag | tggatatcat | a | | | | 321 |

<210> SEQ ID NO 191
<211> LENGTH: 361
<212> TYPE: DNA
<213> ORGANISM: Artificial Sequence
<220> FEATURE:
<223> OTHER INFORMATION: synthetic nucleic acid sequence

<400> SEQUENCE: 191

| | | | | | |
|---|---|---|---|---|---|
| caggtgcagc | tgcaggagtc | gggcccagga | ctggtgaagc | cttcggagac | cctgtccctc | 60 |
| acctgcactg | tctctggtgg | ctccatcagt | tattactact | ggagctggat | ccggcagccc | 120 |

```
ccagggacgg gactggagtg gattgggtat atctattata gtgggagcac caaatacaac    180
ccctccctca agaggcgagt caccatatca gtagacacgt ccaagaacca gttctccctg    240
aagctgagct ctgtgaccgc tgcggacacg gccgtgtatt actgtgcgag aatacgtggg    300
gacagctatg gttgggattt tgactactgg ggccagggaa ccctggtcac cgtctcctca    360
g                                                                    361
```

<210> SEQ ID NO 192
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 192

```
gaaattgtaa tgacacagtc tccagccacc ctgtctttgt ctccagggga aagagccacc     60
ctctcctgca gggccagtca gagtattagc aacaactatt tattctggta ccagcagaaa    120
cctgggcagg ctcccaggct cctcatctat ggtgcttcca ccagggccac tggcatccca    180
gccaggttca gtggcagtgg gtctgggaca gacttcactc tcaccatcag cagcctgcag    240
cctgaagatt ttgcagttta ttactgtcag caggattata acttcctctc cactttcggc    300
ggagggacca aggtggagat caaa                                           324
```

<210> SEQ ID NO 193
<211> LENGTH: 348
<212> TYPE: DNA
<213> ORGANISM: Artificial Sequence
<220> FEATURE:
<223> OTHER INFORMATION: synthetic nucleic acid sequence

<400> SEQUENCE: 193

```
caggtgcagc tgcaggagtc gggcccagga ctggtgaagc cttcggagac cctgtccctc     60
acctgcactg tctctggtgg ctccatcagt agttactact ggagttggat ccggcagccc    120
ccagggaagg gactggagtg gattggatat atctcttata gtgggagcac caactacaac    180
ccctccctca agagtcgagt caccatatca gcagacacgt ccaagaacca attctccctg    240
aagctgagct ctgtgaccgc tgcggacacg gccgtgtatt actgtgcgag agacttttac    300
tacggtatgg acgtctgggg ccaagggacc acggtcaccg tctcctca                 348
```

<210> SEQ ID NO 194
<211> LENGTH: 318
<212> TYPE: DNA
<213> ORGANISM: Artificial Sequence
<220> FEATURE:
<223> OTHER INFORMATION: synthetic nucleic acid sequence

<400> SEQUENCE: 194

```
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaaactcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaccag tttgattatt accctacttt cggcggaggg    300
accaaggtgg agatcaaa                                                  318
```

<210> SEQ ID NO 195

```
<211> LENGTH: 370
<212> TYPE: DNA
<213> ORGANISM: Artificial Sequence
<220> FEATURE:
<223> OTHER INFORMATION: synthetic nucleic acid sequence

<400> SEQUENCE: 195
gaggtgcagc tgttggagtc tgggggaggc tcggaacagc cggggggggtc cctgagactc      60 tcctgtgcag cctctggatt cacctctagc agctatgcca tgagctgggt ccgcctggct     120
ccagggaagg ggctggagtg ggtctcaggt attagtggga gtggtggtgg cacatactac     180
gcagactccg tgaagggccg gttcaccact tccagagaca attccaagaa cacgctgtat     240
ctgcaaatga acagcctgag agccgaggac acggccgtat attactgtac gaaaggggat     300
tactatggtt cggggagtta tccccttttt gactactggg gccagggaac cctggtcacc     360
gtctcctcag                                                             370

<210> SEQ ID NO 196
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 196
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaaactcct gatctctgat gcctccagtt tggaaagtgg ggtcccatct     180
aggttcagcg gcagtggctc tgggacagat ttcactctca ccatcagcag cctgcaacct     240
gaagattttg caacttatta ctgtcaacaa tttaataact cccctccac tttcggccct     300 gggaccaaag tggatatcaa a                                                321

<210> SEQ ID NO 197
<211> LENGTH: 367
<212> TYPE: DNA
<213> ORGANISM: Artificial Sequence
<220> FEATURE:
<223> OTHER INFORMATION: synthetic nucleic acid sequence

<400> SEQUENCE: 197
cagttgcagc tgcaggagtc gggcccagga ctggtgaagc cttcggagac cctgtccctc      60
acctgcactg tctctggtga ctccatcagc agtagtggtt actactgggg ctggatccgc     120
cagcccccag ggaaggggct ggaatggatt gggagtatct attatagtgg gagcacccac     180
tacaacccgt ccctcaagag tcgagtcacc atatccgtag actcgtccaa gagccagttc     240
tccctgaagc taagctctgt gaccgccgca gacacggctg tgtattgctg tgcgagacat     300
aaggtagata gcagtggctg gcccctgac tactggggcc agggaaccct ggtcaccgtc     360
tcctcag                                                                367

<210> SEQ ID NO 198
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 198
gaaattgtaa tgacacagtc tccagccacc ctgtctttgt ctccagggga aagagccacc      60
```

```
ctctcctgca gggccagtca gagtattagc agcagctgct tgtcctggta ccagcagaaa      120
cctgggcagg ctcccaggct cctcatctat gatacatcca ccagggccac tggcatccca      180
gccaggttca gtggcagtgg gtctgggaca gacttcactc tcaccatcag cagcctgcag      240
cctgaagatt ttgcagttta ttactgtcag caggattata acttaccgct cactttcggc      300
ggagggacca aggtggagat caaa                                             324
```

<210> SEQ ID NO 199
<211> LENGTH: 367
<212> TYPE: DNA
<213> ORGANISM: Artificial Sequence
<220> FEATURE:
<223> OTHER INFORMATION: synthetic nucleic acid sequence

<400> SEQUENCE: 199

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtata tggaagtaa tagatactat     180 gcagactccg tgaagggccg attcaccatc tccagagaca attccaagaa cacgctgtat     240
ctgcaaatga acagcctgag agccgaggac acggctgtgt attactgtgc gagagatgac     300
gtagtacgat attttgactg gccccttgac tactggggcc agggaaccct ggtcaccgtc     360
tcctcag                                                               367
```

<210> SEQ ID NO 200
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 200

```
gccatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaaggtcct gatctatgct gcatccagtt tacaaagtgg ggtcccatca     180
aggttcagcg gcagtggatc tggcacagat ttcactctca ccatcagcag cctgcagcct     240
gaagattttg caacttatta ctgtctacaa gattacaatt cccgtggac gttcggccaa     300 gggaccaagg tggaaatcaa a                                                321
```

<210> SEQ ID NO 201
<211> LENGTH: 367
<212> TYPE: DNA
<213> ORGANISM: Artificial Sequence
<220> FEATURE:
<223> OTHER INFORMATION: synthetic nucleic acid sequence

<400> SEQUENCE: 201

```
caggtgcagc tggtggagtc tgggggaggc gtggtccagc ctgggaggtc cctgagactc      60
tcctgtgcag cgtctggatt caccttcagt aactatggca tgcactgggt ccgccaggct     120
ccaggcaagg ggctggagtg ggtggcagtt atatggtata tggaagtaa taaatactat     180 gcagactccg tgaagggccg attcaccatc tccagagaca attccaagaa cacgctgtat     240
ctgcaaatga acagcctgag agccgaggac acggctgtgt attactgtgc gagagatgac     300
gtcgtacgat attttgactg gccccttgac tactggggcc agggaaccct ggtcaccgtc     360
``` tcctcag 367

<210> SEQ ID NO 202
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 202
gccatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaaggtcct gatttatgct gcatccagtt tacaaagtgg ggtcccatca  180
aggttcagcg gcagtggatc tggcacagat ttcactctca ccatcagcag cctgcagcct  240
gaagattttg caacttatta ctgtctacaa gattacaatt acccgtggac gttcggccaa  300
gggaccaagg tggaaatcaa a                                            321

<210> SEQ ID NO 203
<211> LENGTH: 361
<212> TYPE: DNA
<213> ORGANISM: Artificial Sequence
<220> FEATURE:
<223> OTHER INFORMATION: synthetic nucleic acid sequence

<400> SEQUENCE: 203
caggtgcagc tgcaggagtc gggcccagga ctggtgaagc cttcggagac cctgtccctc    60
acctgcactg tctctggtgg ctccatcagt agttactact ggagctggat ccggcagccc  120
ccagggaagg gactggagtg gattgggtat atctattaca gtgggagcac caactacaac  180
ccctccctca gagtcgaat caccatatca gtagacacgt ccaagaacca gttctccctg   240
aagctgagct ctgtgaccgc tgcggacacg gccgtgtatt actgtgcgag agtaatcctg  300
tatagcagtg gctggtcctt cgactactgg ggccagggaa ccctggtcac cgtctcctca  360
g                                                                  361

<210> SEQ ID NO 204
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 204
gaaattgtaa tgacacagtc tccagccacc ctgtctttgt ctccagggga aagagccacc    60
ctctcctgca gggccagtca gagtgttagc agcagctact tatcctggta ccagcagaaa  120
cctgggcagg ctcccaggct cctcatctat ggtgcatcca ccagggccac tggcatccca  180
gccaggttca gtggcagtgg gtctgggaca gacttcactc tcaccatcag cagcctgcag  240
cctgaagatt ttgcagttta ttactgtcag caggattata acttaccgct cactttcggc  300
ggagggacca aggtggagat caaa                                         324

<210> SEQ ID NO 205
<211> LENGTH: 361
<212> TYPE: DNA
<213> ORGANISM: Artificial Sequence
<220> FEATURE:
<223> OTHER INFORMATION: synthetic nucleic acid sequence

<400> SEQUENCE: 205

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgaat caccatatca gtagacacgt ccaagaacca gttctccctg   240
aaactgagct ctgtgaccgc tgcggacacg gccgtgtatt actgtgcgag agtaatcctg   300
tatagcagtg gctggtcctt cgactactgg ggccagggaa ccctggtcac cgtctcctca   360
g                                                                   361
```

<210> SEQ ID NO 206
<211> LENGTH: 324
<212> TYPE: DNA
<213> ORGANISM: Artificial Sequence
<220> FEATURE:
<223> OTHER INFORMATION: synthetic nucleic acid sequence

<400> SEQUENCE: 206

```
gaaattgtaa tgacacagtc tccagccacc ctgtctttgt ctccagggga aagagccacc    60
ctctcctgca gggccagtca gagtgttagc agcagctact tatcctggta ccaacagaag   120
cctgggcagg ctcccaggct cctcatctat gatgcatcca ccagggccac tggcatccca   180
gccaggttca gtggcagtgg gtctgggaca gacttcactc tcaccatcag cagcctgcag   240
cctgaagatt ttgcagttta ttactgtcag caggattata acttaccgct cactttcggc   300
ggagggacca aggtggagat caaa                                          324
```

<210> SEQ ID NO 207
<211> LENGTH: 370
<212> TYPE: DNA
<213> ORGANISM: Artificial Sequence
<220> FEATURE:
<223> OTHER INFORMATION: synthetic nucleic acid sequence

<400> SEQUENCE: 207

```
gaggtgcagt tgttggagtc tgggggaggc ttggtacagc ctgggggtc cctgagactc     60 tcctgtgcag cctctggatt cacctctagc agctatggca tgagctgggt ccgccaggct   120
ccagggaagg ggctggagtg ggtctcaggt attagtggta gtggtggtgg cacatactac   180
gcagactccg tgaagggccg gttcaccatc tccagagaca attccaagaa cacgctgtat   240
ctgcaaatga acagcctgag agccgaggac acggccgtat attactgtgc gaaaggggat   300
tactatggtt cggggagtta tccccttttt gactactggg gccagggaac cctggtcacc   360
gtctcctcag                                                          370
```

<210> SEQ ID NO 208
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 208

```
gccatccagt tgacccagtc tccatcctcc ctgtctgcat ctgtaggaga cagagtcacc    60
atcacttgcc gggcaagtca ggacattagc agtgctttag cctggtatca gcagaaacca   120
gggaaagctc ctaagctcct gatctctgat gcctccagtt tggaaagtgg ggtcccatca   180
aggttcagcg gcagtggatc tgggacagat ttcactctca ccatcagcag cctgcaacct   240
```

| | |
|---|---|
| gaagattttg caacttttta ctgtcaacag tttaataatt accctcccac tttcggccct | 300 |
| gggaccaaag tggatatcaa a | 321 |

<210> SEQ ID NO 209
<211> LENGTH: 369
<212> TYPE: DNA
<213> ORGANISM: Artificial Sequence
<220> FEATURE:
<223> OTHER INFORMATION: synthetic nucleic acid sequence

<400> SEQUENCE: 209

| | |
|---|---|
| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctgaaatg ggtctcaggt attagtggta gtggtggtgg cacatactac | 180 |
| gcagactccg tgaagggccg gttcaccctc tccagagaca attccaagaa cacactatat | 240 |
| ctgcaaatga acagcctgag agccgaggac acggccgtat atttctgtgc gaaaggggat | 300 |
| tactatggtt cggggagtta tccccttttt gacttctggg gccagggaac cctggtcacc | 360 |
| gtctcctca | 369 |

<210> SEQ ID NO 210
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 210

| | |
|---|---|
| gccatccagt tgacccagtc tccatcctcc ctgtctgcat ctgtaggaga cagagtcacc | 60 |
| atcacttgcc gggcaagtca gggcattagc agtgctttag cctggtatca acagaaacca | 120 |
| gggaaagctc ctaagctcct gatctttgat gcctccagtt tggaaagtgg ggtcccatca | 180 |
| aggttcagcg gcagtggatc tgggacagat ttcactctca ccatcagcag cctgcagcct | 240 |
| gaagattttg caacttatta ctgtcaacag tttaatgatt accctcccac tttcggccct | 300 |
| gggaccaaac tggatatcaa a | 321 |

<210> SEQ ID NO 211
<211> LENGTH: 348
<212> TYPE: DNA
<213> ORGANISM: Artificial Sequence
<220> FEATURE:
<223> OTHER INFORMATION: synthetic nucleic acid sequence

<400> SEQUENCE: 211

| | |
|---|---|
| caggtgcagc tgcaggagtc gggcccagga ctggtgaagc cttcggagac cctgtccctc | 60 |
| acctgcactg tctctggtgg ctccatcagt agttactact ggacctggat ccggcagccc | 120 |
| ccagggaagg gactggagtg gattggacat atctcttaca gtgggagcac ccactacaac | 180 |
| ccctccctca gagtcgatt caccatatca gcagacacgt ccaagaaccg gttctccctg | 240 |
| aagctgagct ctgtgaccgc tgcggacacg gccgtgtatt actgtgcgcg agatggctac | 300 |
| tacgctttgg acgtctgggg ccaagggacc acggtcaccg tctcctca | 348 |

<210> SEQ ID NO 212
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 212

```
gccatccagt tgacccagtc tccatcctcc ctgtctgcat ctgtaggaga cagagtcacc    60
atcacttgcc gggcaagtca ggacattagc aatactgtag cctggtatca gcagaaccca   120
gggaaagctc ctaagctcct gatctatgat gcctccagtt tggaaagtgg ggtctcatca   180
aggttcagcg gcagtggatc ggggacagat ttcactctca ccatcagcag cctgcagcct   240
gaagattttg caacttatta ctgtcaacag tttaataatt acccgtacac ttttggccag   300
gggaccaagc tggagatcaa a                                             321
```

<210> SEQ ID NO 213
<211> LENGTH: 369
<212> TYPE: DNA
<213> ORGANISM: Artificial Sequence
<220> FEATURE:
<223> OTHER INFORMATION: synthetic nucleic acid sequence

<400> SEQUENCE: 213

```
gaggtgcagc tgttggagtc tgggggaggc ttggaacagc cggggggtc cctgagactc     60
tcctgtgcag cctctggatt cacctctagc agctatgcca tgagctgggt ccgccaggct   120
ccagggaagg gctggagtg gtctcaggt attagtggga gtggtggtgg cacatactac     180
gcagactccg tgaagggccg gttctccact tccagagaca attccaagaa cacgctttat   240
ctgcaaatga acagcctgag agccgaggac acggccgtat attactgtgc gaaaggggat   300
tactatggtt cggggagtta tccccttttt gactactggg gccagggaac cctggtcacc   360
gtctcctca                                                           369
```

<210> SEQ ID NO 214
<211> LENGTH: 321
<212> TYPE: DNA
<213> ORGANISM: Artificial Sequence
<220> FEATURE:
<223> OTHER INFORMATION: synthetic nucleic acid sequence

<400> SEQUENCE: 214

```
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaacctc ctaagctcct gatctctgat gcctccagtt tggaaagtgg ggtcccatct   180
aggttcagcg gcagtggctc tgggacagat ttcactctca ccatcagcag cctgcagcct   240
gaagattttg caacttatta ctgtcaacag tttaataact accctcccac tttcggccct   300
gggaccaaag tggatatcaa a                                             321
```

BTLA-BINDING ANTIBODIES FOR MODULATING IMMUNE RESPONSE AND TREATING DISEASE

CROSS-REFERENCE TO RELATED APPLICATION

This application claims priority to U.S. Provisional Patent Application No. 62/827,744, filed on Apr. 1, 2019, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 29, 2020, is named 119519-5001-US ST25.txt and is 100 kilobytes in size.

TECHNICAL FIELD

The present disclosure relates to novel anti-BTLA antibodies and pharmaceutical compositions comprising such antibodies for use in modulating immune response, and treatment of diseases such as cancer or autoimmune disease.

BACKGROUND OF THE INVENTION

The treatment of diseases by inducing, enhancing, or suppressing an immune response is referred to as immunotherapy. Immunotherapy has demonstrated increasing effectiveness in treating cancer. In general, the tumor microenvironment enables cancer cells to evade detection by the immune system, for example, by upregulation of immune-inhibitory proteins expressed by the tumor cells themselves (e.g., PDL1, HVEM). White blood cells express specific receptors (also known as immune checkpoint receptors) for these inhibitory proteins (e.g., PD1 for PDL1, and BTLA for HVEM), and therefore, tumor cells can engage immune checkpoint receptors to suppress immune responses against themselves.

Much immunotherapeutic success in cancer treatment is based on the use of immune-modulating antibodies that target immune checkpoints CTLA-4 and PD-1/PD-L1. However, many FDA-approved antibodies that block the immune checkpoint pair are only effective in ~20% of cancer patients. For the responders, the treatment is highly effective and durable. However, for the remaining 80% of cancer patients who are non-responders, there is a demand for new immunotherapies that target other immune checkpoints.

BTLA (B- and T-lymphocyte attenuator) is a transmembrane protein, and its expression is induced during activation of T cells. BTLA is also expressed on B cells and dendritic cells. Like PD1 and CTLA4, BTLA interacts with a B7 homolog, B7H4. However, unlike PD-1 and CTLA-4, BTLA also interacts with tumor necrosis family receptors. One such receptor is tumor necrosis factor (receptor) superfamily member 14 (TNFRSF14), also known as herpes virus entry mediator (HVEM). HVEM is the receptor for the HSV glycoprotein D involved in viral entry, and is expressed in hematopoietic cells, including B and T cells, as well as in nonhematopoietic cells (parenchymal cells). In addition, HVEM is expressed in a variety of hematological and solid tumors. BTLA-HVEM interaction down-regulates T cell response, such as CD8+ T cell response. Upregulation of BTLA and/or HVEM is found to be a mechanism exerted by tumor cells to escape immune recognition and destruction. For example, BTLA and HVEM are highly expressed in B-cell chronic lymphocytic leukemia, and gastric cancer; and BTLA expression is upregulated in Hodgkin's lymphoma, B-cell non-Hodgkin's lymphoma and some T-cell non-Hodgkin's lymphomas, as well as on cytotoxic CD8+ T cells in peripheral blood of the patients with hepatocellular carcinoma. In addition, the absence of HVEM-BTLA signaling results in exaggerated immune responses that lead to dysregulated inflammation and autoimmune diseases. As such, modulation of BTLA signaling can be a target for both cancer and autoimmune disease.

SUMMARY OF THE INVENTION

In one aspect, the present invention relates to novel anti-BTLA antibodies. In some embodiments, the anti-BTLA antibodies include a heavy chain variable region comprising an amino acid sequence of SEQ ID NO:1 and a light chain variable region comprising an amino acid sequence of SEQ ID NO:2. In some embodiments, the anti-BTLA antibodies include a heavy chain variable region comprising an amino acid sequence of SEQ ID NO:3 and a light chain variable region comprising an amino acid sequence of SEQ ID NO:4. In some embodiments, the anti-BTLA antibodies include a heavy chain variable region comprising an amino acid sequence of SEQ ID NO:5 and a light chain variable region comprising an amino acid sequence of SEQ ID NO:6. In some embodiments, the anti-BTLA antibodies include a heavy chain variable region comprising an amino acid sequence of SEQ ID NO:7 and a light chain variable region comprising an amino acid sequence of SEQ ID NO:8. In some embodiments, the anti-BTLA antibodies include a heavy chain variable region comprising an amino acid sequence of SEQ ID NO:9 and a light chain variable region comprising an amino acid sequence of SEQ ID NO:10. In some embodiments, the anti-BTLA antibodies include a heavy chain variable region comprising an amino acid sequence of SEQ ID NO:11 and a light chain variable region comprising an amino acid sequence of SEQ ID NO:12. In some embodiments, the anti-BTLA antibodies include a heavy chain variable region comprising an amino acid sequence of SEQ ID NO:13 and a light chain variable region comprising an amino acid sequence of SEQ ID NO:14. In some embodiments, the anti-BTLA antibodies include a heavy chain variable region comprising an amino acid sequence of SEQ ID NO:15 and a light chain variable region comprising an amino acid sequence of SEQ ID NO:16. In some embodiments, the anti-BTLA antibodies include a heavy chain variable region comprising an amino acid sequence of SEQ ID NO:17 and a light chain variable region comprising an amino acid sequence of SEQ ID NO:18. In some embodiments, the anti-BTLA antibodies include a heavy chain variable region comprising an amino acid sequence of SEQ ID NO:19 and a light chain variable region comprising an amino acid sequence of SEQ ID NO:20. In some embodiments, the anti-BTLA antibodies include a heavy chain variable region comprising an amino acid sequence of SEQ ID NO:21 and a light chain variable region comprising an amino acid sequence of SEQ ID NO:22. In some embodiments, the anti-BTLA antibodies include a heavy chain variable region comprising an amino acid sequence of SEQ ID NO:23 and a light chain variable region comprising an amino acid sequence of SEQ ID NO:24. In some embodiments, the anti-BTLA antibodies include a heavy chain variable region comprising an amino acid sequence of SEQ ID NO:25 and a light chain variable region comprising an amino acid sequence of SEQ ID NO:26. In some embodiments, the anti-BTLA antibodies include a heavy chain variable region comprising an amino acid sequence of SEQ ID NO:27 and a light chain variable region comprising an amino acid sequence of SEQ ID NO:28. In some embodiments, the anti-BTLA antibodies include a heavy chain variable region comprising an amino acid sequence of SEQ ID NO:29 and a light chain variable region comprising an amino acid sequence of SEQ ID NO:30. In some embodiments, the anti-BTLA antibodies include a heavy chain variable region comprising an amino acid sequence of SEQ ID NO:31 and a light chain variable region comprising an amino acid sequence of SEQ ID NO:32. In some embodiments, the anti-BTLA antibodies include a heavy chain variable region comprising an amino acid sequence of SEQ ID NO:33 and a light chain variable region comprising an amino acid sequence of SEQ ID NO:34. In some embodiments, the anti-BTLA antibodies include a heavy chain variable region comprising an amino acid sequence of SEQ ID NO:35 and a light chain variable region comprising an amino acid sequence of SEQ ID NO:36. In some embodiments, the anti-BTLA antibodies include a heavy chain variable region comprising an amino acid sequence of SEQ ID NO:37 and a light chain variable region comprising an amino acid sequence of SEQ ID NO:38. In some embodiments, the anti-BTLA antibodies include a heavy chain variable region comprising an amino acid sequence of SEQ ID NO:39 and a light chain variable region comprising an amino acid sequence of SEQ ID NO:40. In some embodiments, the anti-BTLA antibodies include a heavy chain variable region comprising an amino acid sequence of SEQ ID NO:41 and a light chain variable region comprising an amino acid sequence of SEQ ID NO:42.

In some embodiments, the anti-BTLA antibodies include a vhCDR1 comprising SEQ ID NO:47, a vhCDR2 comprising SEQ ID NO:48, a vhCDR3 comprising SEQ ID NO:49, a vlCDR1 comprising SEQ ID NO:50, a vlCDR2 comprising SEQ ID NO:51, and a vlCDR3 comprising SEQ ID NO:52. In some embodiments, the anti-BTLA antibodies include a vhCDR1 comprising SEQ ID NO:53, a vhCDR2 comprising SEQ ID NO:54, a vhCDR3 comprising SEQ ID NO:55, a vlCDR1 comprising SEQ ID NO:56, a vlCDR2 comprising SEQ ID NO:57, and a vlCDR3 comprising SEQ ID NO:58. In some embodiments, the anti-BTLA antibodies include a vhCDR1 comprising SEQ ID NO:59, a vhCDR2 comprising SEQ ID NO:60, a vhCDR3 comprising SEQ ID NO:61, a vlCDR1 comprising SEQ ID NO:62, a vlCDR2 comprising SEQ ID NO:63, and a vlCDR3 comprising SEQ ID NO:64. In some embodiments, the anti-BTLA antibodies include a vhCDR1 comprising SEQ ID NO:65, a vhCDR2 comprising SEQ ID NO:66, a vhCDR3 comprising SEQ ID NO:67, a vlCDR1 comprising SEQ ID NO:68, a vlCDR2 comprising SEQ ID NO:69, and a vlCDR3 comprising SEQ ID NO:70. In some embodiments, the anti-BTLA antibodies include a vhCDR1 comprising SEQ ID NO:71, a vhCDR2 comprising SEQ ID NO:72, a vhCDR3 comprising SEQ ID NO:73, a vlCDR1 comprising SEQ ID NO:74, a vlCDR2 comprising SEQ ID NO:75, and a vlCDR3 comprising SEQ ID NO:76. In some embodiments, the anti-BTLA antibodies include a vhCDR1 comprising SEQ ID NO:77, a vhCDR2 comprising SEQ ID NO:78, a vhCDR3 comprising SEQ ID NO:79, a vlCDR1 comprising SEQ ID NO:80, a vlCDR2 comprising SEQ ID NO:81, and a vlCDR3 comprising SEQ ID NO:82. In some embodiments, the anti-BTLA antibodies include a vhCDR1 comprising SEQ ID NO:83, a vhCDR2 comprising SEQ ID NO:84, a vhCDR3 comprising SEQ ID NO:85, a vlCDR1 comprising SEQ ID NO:86, a vlCDR2 comprising SEQ ID NO:87, and a vlCDR3 comprising SEQ ID NO:88. In some embodiments, the anti-BTLA antibodies include a vhCDR1 comprising SEQ ID NO:89, a vhCDR2 comprising SEQ ID NO:90, a vhCDR3 comprising SEQ ID NO:91, a vlCDR1 comprising SEQ ID NO:92, a vlCDR2 comprising SEQ ID NO:93, and a vlCDR3 comprising SEQ ID NO:94. In some embodiments, the anti-BTLA antibodies include a vhCDR1 comprising SEQ ID NO:95, a vhCDR2 comprising SEQ ID NO:96, a vhCDR3 comprising SEQ ID NO:97, a vlCDR1 comprising SEQ ID NO:98, a vlCDR2 comprising SEQ ID NO:99, and a vlCDR3 comprising SEQ ID NO:100. In some embodiments, the anti-BTLA antibodies include a vhCDR1 comprising SEQ ID NO:101, a vhCDR2 comprising SEQ ID NO:102, a vhCDR3 comprising SEQ ID NO:103, a vlCDR1 comprising SEQ ID NO:104, a vlCDR2 comprising SEQ ID NO:105, and a vlCDR3 comprising SEQ ID NO:106. In some embodiments, the anti-BTLA antibodies include a vhCDR1 comprising SEQ ID NO:107, a vhCDR2 comprising SEQ ID NO:108, a vhCDR3 comprising SEQ ID NO:109, a vlCDR1 comprising SEQ ID NO:110, a vlCDR2 comprising SEQ ID NO:111, and a vlCDR3 comprising SEQ ID NO:112. In some embodiments, the anti-BTLA antibodies include a vhCDR1 comprising SEQ ID NO:113, a vhCDR2 comprising SEQ ID NO:114, a vhCDR3 comprising SEQ ID NO:115, a vlCDR1 comprising SEQ ID NO:116, a vlCDR2 comprising SEQ ID NO:117, and a vlCDR3 comprising SEQ ID NO:118. In some embodiments, the anti-BTLA antibodies include a vhCDR1 comprising SEQ ID NO:119, a vhCDR2 comprising SEQ ID NO:120, a vhCDR3 comprising SEQ ID NO:121, a vlCDR1 comprising SEQ ID NO:122, a vlCDR2 comprising SEQ ID NO:123, and a vlCDR3 comprising SEQ ID NO:124. In some embodiments, the anti-BTLA antibodies include a vhCDR1 comprising SEQ ID NO:125, a vhCDR2 comprising SEQ ID NO:126, a vhCDR3 comprising SEQ ID NO:127, a vlCDR1 comprising SEQ ID NO:128, a vlCDR2 comprising SEQ ID NO:129, and a vlCDR3 comprising SEQ ID NO:130. In some embodiments, the anti-BTLA antibodies include a vhCDR1 comprising SEQ ID NO:131, a vhCDR2 comprising SEQ ID NO:132, a vhCDR3 comprising SEQ ID NO:133, a vlCDR1 comprising SEQ ID NO:134, a vlCDR2 comprising SEQ ID NO:135, and a vlCDR3 comprising SEQ ID NO:136. In some embodiments, the anti-BTLA antibodies include a vhCDR1 comprising SEQ ID NO:137, a vhCDR2 comprising SEQ ID NO:138, a vhCDR3 comprising SEQ ID NO:139, a vlCDR1 comprising SEQ ID NO:140, a vlCDR2 comprising SEQ ID NO:141, and a vlCDR3 comprising SEQ ID NO:142. In some embodiments, the anti-BTLA antibodies include a vhCDR1 comprising SEQ ID NO:143, a vhCDR2 comprising SEQ ID NO:144, a vhCDR3 comprising SEQ ID NO:145, a vlCDR1 comprising SEQ ID NO:146, a vlCDR2 comprising SEQ ID NO:147, and a vlCDR3 comprising SEQ ID NO:148. In some embodiments, the anti-BTLA antibodies include a vhCDR1 comprising SEQ ID NO:149, a vhCDR2 comprising SEQ ID NO:150, a vhCDR3 comprising SEQ ID NO:151, a vlCDR1 comprising SEQ ID NO:152, a vlCDR2 comprising SEQ ID NO:153, and a vlCDR3 comprising SEQ ID NO:154. In some embodiments, the anti-BTLA antibodies include a vhCDR1 comprising SEQ ID NO:155, a vhCDR2 comprising SEQ ID NO:156, a vhCDR3 comprising SEQ ID NO:157, a vlCDR1 comprising SEQ ID NO:158, a vlCDR2 comprising SEQ ID NO:159, and a vlCDR3 comprising SEQ ID NO:160. In some embodiments, the anti-BTLA antibodies include a vhCDR1 comprising SEQ ID NO:161, a vhCDR2 comprising SEQ ID NO:162, a vhCDR3 comprising SEQ ID NO:163, a vlCDR1 comprising SEQ ID NO:164, a vlCDR2 comprising SEQ ID NO:165, and a vlCDR3 comprising SEQ ID NO:166. In some embodiments, the anti-BTLA antibodies include a vhCDR1 comprising SEQ ID NO:167, a vhCDR2 comprising SEQ ID NO:168, a vhCDR3 comprising SEQ ID NO:169, a vlCDR1 comprising SEQ ID NO:170, a vlCDR2 comprising SEQ ID NO:171, and a vlCDR3 comprising SEQ ID NO:172.

In some embodiments, the anti-BTLA antibodies described herein bind human and/or cynomolgus BTLA.

In some embodiments, the anti-BTLA antibodies act as BTLA antagonists, and block binding of BTLA to HVEM as well as HVEM-mediated suppression of T cell functions. Examples of such antibodies include antibodies that contain a heavy chain variable region comprising an amino acid sequence of SEQ ID NO:21 and a light chain variable region comprising an amino acid sequence of SEQ ID NO:22; a heavy chain variable region comprising an amino acid sequence of SEQ ID NO:31 and a light chain variable region comprising an amino acid sequence of SEQ ID NO:32; a heavy chain variable region comprising an amino acid sequence of SEQ ID NO:35 and a light chain variable region comprising an amino acid sequence of SEQ ID NO:36; a vhCDR1 comprising SEQ ID NO:107, a vhCDR2 comprising SEQ ID NO:108, a vhCDR3 comprising SEQ ID NO:109, a vlCDR1 comprising SEQ ID NO:110, a vlCDR2 comprising SEQ ID NO:111, and a vlCDR3 comprising SEQ ID NO:112; a vhCDR1 comprising SEQ ID NO:137, a vhCDR2 comprising SEQ ID NO:138, a vhCDR3 comprising SEQ ID NO:139, a vlCDR1 comprising SEQ ID NO:140, a vlCDR2 comprising SEQ ID NO:141, and a vlCDR3 comprising SEQ ID NO:142; or a vhCDR1 comprising SEQ ID NO:149, a vhCDR2 comprising SEQ ID NO:150, a vhCDR3 comprising SEQ ID NO:151, a vlCDR1 comprising SEQ ID NO:152, a vlCDR2 comprising SEQ ID NO:153, and a vlCDR3 comprising SEQ ID NO:154.

In some embodiments, the anti-BTLA antibodies act as BTLA agonists, and suppress pro-inflammatory immune cell functions. Examples of such antibodies include antibodies that contain a heavy chain variable region comprising an amino acid sequence of SEQ ID NO:19 and a light chain variable region comprising an amino acid sequence of SEQ ID NO:20; a heavy chain variable region comprising an amino acid sequence of SEQ ID NO:25 and a light chain variable region comprising an amino acid sequence of SEQ ID NO:26; a heavy chain variable region comprising an amino acid sequence of SEQ ID NO:29 and a light chain variable region comprising an amino acid sequence of SEQ ID NO:30; a vhCDR1 comprising SEQ ID NO:101, a vhCDR2 comprising SEQ ID NO:102, a vhCDR3 comprising SEQ ID NO:103, a vlCDR1 comprising SEQ ID NO:104, a vlCDR2 comprising SEQ ID NO:105, and a vlCDR3 comprising SEQ ID NO:106; a vhCDR1 comprising SEQ ID NO:119, a vhCDR2 comprising SEQ ID NO:120, a vhCDR3 comprising SEQ ID NO:121, a vlCDR1 comprising SEQ ID NO:122, a vlCDR2 comprising SEQ ID NO:123, and a vlCDR3 comprising SEQ ID NO:124; or a vhCDR1 comprising SEQ ID NO:131, a vhCDR2 comprising SEQ ID NO:132, a vhCDR3 comprising SEQ ID NO:133, a vlCDR1 comprising SEQ ID NO:134, a vlCDR2 comprising SEQ ID NO:135, and a vlCDR3 comprising SEQ ID NO:136.

In some embodiments, the anti-BTLA antibodies described herein include a constant region with an amino acid sequence at least 90% identical to a human IgG. In some embodiments, the IgG is selected from an IgG1, IgG2, IgG3 or IgG4. In some embodiments, the IgG is an IgG2.

In another aspect, the present invention relates to a nucleic acid composition encoding any one of the anti-BTLA antibodies described herein. In some embodiments, the nucleic acid composition includes a first nucleic acid comprising SEQ ID NO:185, and a second nucleic acid comprising SEQ ID NO186. In some embodiments, the nucleic acid composition includes a first nucleic acid comprising SEQ ID NO:187, and a second nucleic acid comprising SEQ ID NO:188. In some embodiments, the nucleic acid composition includes a first nucleic acid comprising SEQ ID NO:189, and a second nucleic acid comprising SEQ ID NO:190. In some embodiments, the nucleic acid composition includes a first nucleic acid comprising SEQ ID NO:191, and a second nucleic acid comprising SEQ ID NO:192. In some embodiments, the nucleic acid composition includes a first nucleic acid comprising SEQ ID NO:193, and a second nucleic acid comprising SEQ ID NO:194. In some embodiments, the nucleic acid composition includes a first nucleic acid comprising SEQ ID NO:195, and a second nucleic acid comprising SEQ ID NO:196. In some embodiments, the nucleic acid composition includes a first nucleic acid comprising SEQ ID NO:197, and a second nucleic acid comprising SEQ ID NO:198. In some embodiments, the nucleic acid composition includes a first nucleic acid comprising SEQ ID NO:199, and a second nucleic acid comprising SEQ ID NO:200. In some embodiments, the nucleic acid composition includes a first nucleic acid comprising SEQ ID NO:201, and a second nucleic acid comprising SEQ ID NO:202. In some embodiments, the nucleic acid composition includes a first nucleic acid comprising SEQ ID NO:203, and a second nucleic acid comprising SEQ ID NO:204. In some embodiments, the nucleic acid composition includes a first nucleic acid comprising SEQ ID NO:205, and a second nucleic acid comprising SEQ ID NO:206. In some embodiments, the nucleic acid composition includes a first nucleic acid comprising SEQ ID NO:207, and a second nucleic acid comprising SEQ ID NO:208. In some embodiments, the nucleic acid composition includes a first nucleic acid comprising SEQ ID NO:209, and a second nucleic acid comprising SEQ ID NO:210. In some embodiments, the nucleic acid composition includes a first nucleic acid comprising SEQ ID NO:211, and a second nucleic acid comprising SEQ ID NO:212. In some embodiments, the nucleic acid composition includes a first nucleic acid comprising SEQ ID NO:213, and a second nucleic acid comprising SEQ ID NO:214. In some embodiments, the nucleic acid composition includes a first nucleic acid comprising SEQ ID NO:215, and a second nucleic acid comprising SEQ ID NO:216. In some embodiments, the nucleic acid composition includes a first nucleic acid comprising SEQ ID NO:217, and a second nucleic acid comprising SEQ ID NO:218. In some embodiments, the nucleic acid composition includes a first nucleic acid comprising SEQ ID NO:219, and a second nucleic acid comprising SEQ ID NO:220. In some embodiments, the nucleic acid composition includes a first nucleic acid comprising SEQ ID NO:221, and a second nucleic acid comprising SEQ ID NO:222. In some embodiments, the nucleic acid composition includes a first nucleic acid comprising SEQ ID NO:223, and a second nucleic acid comprising SEQ ID NO:224. In some embodiments, the nucleic acid composition includes a first nucleic acid comprising SEQ ID NO:225, and a second nucleic acid comprising SEQ ID NO:226.

Another aspect of the present invention relates to an expression vector composition that includes any one of the nucleic acid compositions described herein. In some embodiments, the first nucleic acid is contained in a first expression vector and the second nucleic acid is contained in a second expression vector. In some other embodiments, the first nucleic acid and the second nucleic acid are contained in a single expression vector.

Another aspect of the present invention relates to a host cell that includes any one of the expression vectors described herein. Also presented is a method of making anti-BTLA antibodies, and the method includes culturing the host cell under conditions wherein the antibodies expressed, and recovering the antibodies.

In another aspect, the present invention relates to a composition that includes any one of the anti-BTLA antibodies described herein, and a pharmaceutical acceptable carrier or diluent.

Also described is a method of modulating an immune response in a subject, and the method includes administering to the subject an effective amount of any one of the anti-BTLA antibodies described herein, or any one of the compositions described herein. In some embodiments, the method stimulates an immune response in the subject and the method includes administering to the subject an effective amount of an anti-BTLA antibody that serves as a BTLA antagonist, or a pharmaceutical composition thereof. In some embodiments, the method suppresses an immune response in the subject and the method includes administering to the subject an effective amount of an anti-BTLA antibody that serves as a BTLA agonist, or a pharmaceutical composition thereof.

In some embodiments, the method stimulates an immune response in the subject, and the method includes administering to the subject an effective amount of an anti-BTLA antibody, wherein the anti-BTLA antibody includes a heavy chain variable region comprising an amino acid sequence of SEQ ID NO:21 and a light chain variable region comprising an amino acid sequence of SEQ ID NO:22; and/or a vhCDR1 comprising SEQ ID NO:107, a vhCDR2 comprising SEQ ID NO:108, a vhCDR3 comprising SEQ ID NO:109, a vlCDR1 comprising SEQ ID NO:110, a vlCDR2 comprising SEQ ID NO:111, and a vlCDR3 comprising SEQ ID NO:112.

In some embodiments, the method stimulates an immune response in the subject, and the method includes administering to the subject an effective amount of an anti-BTLA antibody, wherein the anti-BTLA antibody includes a heavy chain variable region comprising an amino acid sequence of SEQ ID NO:31 and a light chain variable region comprising an amino acid sequence of SEQ ID NO:32; and/or a vhCDR1 comprising SEQ ID NO:137, a vhCDR2 comprising SEQ ID NO:138, a vhCDR3 comprising SEQ ID NO:139, a vlCDR1 comprising SEQ ID NO:140, a vlCDR2 comprising SEQ ID NO:141, and a vlCDR3 comprising SEQ ID NO:142.

In some embodiments, the method stimulates an immune response in the subject, and the method includes administering to the subject an effective amount of an anti-BTLA antibody, wherein the anti-BTLA antibody includes a heavy chain variable region comprising an amino acid sequence of SEQ ID NO:35 and a light chain variable region comprising an amino acid sequence of SEQ ID NO:36; and/or a vhCDR1 comprising SEQ ID NO:149, a vhCDR2 comprising SEQ ID NO:150, a vhCDR3 comprising SEQ ID NO:151, a vlCDR1 comprising SEQ ID NO:152, a vlCDR2 comprising SEQ ID NO:153, and a vlCDR3 comprising SEQ ID NO:154.

In some embodiments, the method suppresses an immune response in the subject, and the method includes administering to the subject an effective amount of an anti-BTLA antibody, wherein the anti-BTLA antibody includes a heavy chain variable region comprising an amino acid sequence of SEQ ID NO:19 and a light chain variable region comprising an amino acid sequence of SEQ ID NO:20; and/or a vhCDR1 comprising SEQ ID NO:101, a vhCDR2 comprising SEQ ID NO:102, a vhCDR3 comprising SEQ ID NO:103, a vlCDR1 comprising SEQ ID NO:104, a vlCDR2 comprising SEQ ID NO:105, and a vlCDR3 comprising SEQ ID NO:106.

In some embodiments, the method suppresses an immune response in the subject, and the method includes administering to the subject an effective amount of an anti-BTLA antibody, wherein the anti-BTLA antibody includes a heavy chain variable region comprising an amino acid sequence of SEQ ID NO:25 and a light chain variable region comprising an amino acid sequence of SEQ ID NO:26; and/or a vhCDR1 comprising SEQ ID NO:119, a vhCDR2 comprising SEQ ID NO:120, a vhCDR3 comprising SEQ ID NO:121, a vlCDR1 comprising SEQ ID NO:122, a vlCDR2 comprising SEQ ID NO:123, and a vlCDR3 comprising SEQ ID NO:124.

In some embodiments, the method suppresses an immune response in the subject, and the method includes administering to the subject an effective amount of an anti-BTLA antibody, wherein the anti-BTLA antibody includes a heavy chain variable region comprising an amino acid sequence of SEQ ID NO:29 and a light chain variable region comprising an amino acid sequence of SEQ ID NO:30; and/or a vhCDR1 comprising SEQ ID NO:131, a vhCDR2 comprising SEQ ID NO:132, a vhCDR3 comprising SEQ ID NO:133, a vlCDR1 comprising SEQ ID NO:134, a vlCDR2 comprising SEQ ID NO:135, and a vlCDR3 comprising SEQ ID NO:136.

In another aspect, the present invention relates to a method of treating cancer in a subject, and the method includes administering to the subject an effective amount of an anti-BTLA antibody described herein, or a composition thereof, wherein the anti-BTLA antibody serves as a BTLA antagonist. In some embodiments, the cancer to be treated upregulates HVEM compared to the corresponding non-cancerous tissue. In some embodiments, the subject to be treated expresses a high level of BTLA on T cells. The cancer to be treated can be a gastric cancer. In some embodiments, an anti-BTLA antibody is used in combination with one or more additional therapeutic agents to treat cancer. In some embodiments, such anti-cancer therapeutic agents are other immune checkpoint inhibitors, such as Ipilimumab, Nivolumab, Pembrolizumab, Avelumab, Durvalumab, and Atezolizumab.

In another aspect, the present invention relates to a method of treating an autoimmune disease in a subject, and the method includes administering to the subject an effective amount of an anti-BTLA antibody described herein, or a composition thereof, wherein the anti-BTLA antibody serves as a BTLA agonist. In some embodiments, the subject to be treated has a low level of HVEM on autoreactive T cells residing at sites where the autoimmune disease develops. In some embodiments, the autoimmune disease is multiple sclerosis.

BRIEF DESCRIPTION OF THE DRAWINGS

The invention may be best understood from the following detailed description when read in conjunction with the accompanying drawings. Included in the drawings are the following figures:

FIG. 2A shows binding of 13-F7A to human BTLA expressed on HEK-293 cells. FIG. 2B shows binding of 13-F7A to cynomolgus BTLA expressed on HEK-293 cells. FIG. 2C is a negative control showing binding of 13-F7A to HEK-293 cells. 10 μg/ml and 1 μg/ml of the antibody were tested together with the secondary antibody only control.

FIGS. 5A-5C show anti-BTLA antibodies 16420A, 15-C19A, and 16-H16A and their antagonistic effects on T cell function. FIGS. 5D-5F show anti-BTLA antibodies 12-IBA, 8-M23A and 13-F7A and their agonistic effects on T cell function.

DETAILED DESCRIPTION

Figure 1:
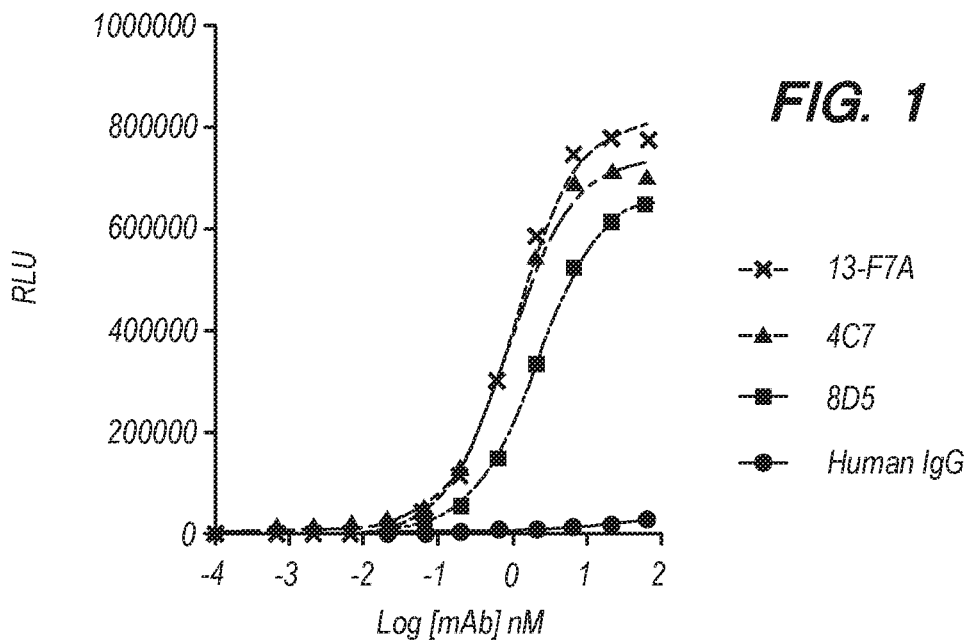
FIG. 1 shows binding of anti-BTLA antibody 13-F7A to human BTLA by ELISA. Anti-BTLA antibodies 4C7 and 8D5 were used as controls. Human IgG was used as a negative control. Relative light units (RLU) were calculated.

The present disclosure provides novel anti-BTLA antibodies. The anti-BTLA antibodies described herein bind human and/or cynomolgus BTLA. In some embodiments, the anti-BTLA antibodies bind human and/or cynomolgus BTLA with high affinities. In some embodiments, the anti-BTLA antibodies act as functional BTLA antagonists, and upon binding to BTLA they block interaction of BTLA with HVEM, and block HVEM-mediated suppression of T cell functions. In some embodiments, the anti-BTLA antibodies act as functional BTLA agonists, and upon binding to BTLA they suppress T cell functions. Also provided in the present disclosure are methods of using such antibodies to modulate an immune response in a subject, and, for example, to treat cancer or an autoimmune disease. In addition, nucleic acids encoding these antibodies, as well as host cells that include such nucleic acids are described in the present disclosure.

To facilitate an understanding of the present invention, a number of terms and phrases are defined below.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, an "antigen binding domain" binds a target antigen as outlined herein. As is known in the art, these CDRs are generally present as a first set of variable heavy CDRs (vhCDRs or VHCDRs or CDR-HC) and a second set of variable light CDRs (vlCDRs or VLCDRs or CDR-LC), each comprising three CDRs: vhCDR1, vhCDR2, vhCDR3 for the heavy chain and vlCDR1, vlCDR2 and vlCDR3 for the light chain. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the VH and VL domains are covalently attached, generally through the use of a linker as outlined herein, into a single polypeptide sequence, which can be either (starting from the N-terminus) vh-linker-vl or vl-linker-vh, with the former being generally preferred (including optional domain linkers on each side, depending on the format used. As is understood in the art, the CDRs are separated by framework regions in each of the variable heavy and variable light domains: for the light variable region, these are FR1-vlCDR1-FR2-vlCDR2-FR3-vlCDR3-FR4, and for the heavy variable region, these are FR1-vhCDR1-FR2-vhCDR2-FR3-vhCDR3-FR4, with the framework regions showing high identity to human germline sequences. Antigen binding domains of the invention include, Fab, Fv and scFv.

By "linker" herein is meant a linker used in scFv and/or other antibody structures. Generally, there are a number of suitable scFv linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 4), glycine-alanine polymers, alanine-serine polymers, and other flexible linkers. Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers, that is may find use as linkers. Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR), hinge region-derived sequences, and other natural sequences from other proteins. In some embodiments, the linker is a "domain linker", used to link any two domains as outlined herein together. While any suitable linker can be used, many embodiments utilize a glycine-serine polymer, including for example (GS)n, (GSGGS)n, (GGGGS)n, and (GGGS)n, where n is an integer of at least one (and generally from 3 to 4 to 5) as well as any peptide sequence that allows for recombinant attachment of the two domains with sufficient length and flexibility to allow each domain to retain its biological function.

The term "antibody" is used in the broadest sense and includes, for example, an intact immunoglobulin or an antigen binding portion. Antigen binding portions may be produced by recombinant DNA techniques or by enzymatic or chemical cleavage of intact antibodies. Thus the term antibody includes traditional tetrameric antibodies of two heavy chains and two light chains, as well as antigen binding fragments such as Fv, Fab and scFvs. In some cases, the invention provides bispecific antibodies that include at least one antigen binding domain as outlined herein.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution M252Y refers to a variant polypeptide, in this case an Fc variant, in which the methionine at position 252 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4. The protein variant sequence herein will preferably possess at least about 80% identity with a parent protein sequence, and most preferably at least about 90% identity, more preferably at least about 95%-98%-99% identity. Variant protein can refer to the variant protein itself, compositions comprising the protein variant, or the DNA sequence that encodes it.

Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example M252Y or 252Y is an Fc variant with the substitution tyrosine at position 252 relative to the parent Fc polypeptide, wherein the numbering is according to the EU index. Likewise, M252Y/S254T/T256E defines an Fc variant with the substitutions M252Y, S254T and T256E relative to the parent Fc polypeptide. The identity of the wild type amino acid may be unspecified, in which case the aforementioned variant is referred to as 252Y/254T/256E. It is noted that the order in which substitutions are provided is arbitrary, that is to say that, for example, 252Y/254T/256E is the same Fc variant as 254T/252Y/256E, and so on. For all positions discussed in the present invention that relate to antibodies, unless otherwise noted, amino acid position numbering is according to Kabat for the variable region numbering and is according to the EU index for the constant regions, including the Fc region. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids.

As used herein, "protein" herein is meant at least two covalently attached amino acids, which includes proteins, polypeptides, oligopeptides and peptides. The peptidyl group may comprise naturally occurring amino acids and peptide bonds.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein.

By "Fv" or "Fv fragment" or "Fv region" as used herein is meant a polypeptide that comprises the VL and VH domains of a single antigen binding domain (ABD). As will be appreciated by those in the art, these generally are made up of two chains, or can be combined (generally with a linker as discussed herein) to form a scFv.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. In some cases, as outlined herein, binding to one or more of the FcγR receptors is reduced or ablated. For example, reducing binding to FcγRIIIa reduces ADCC, and in some cases, reducing binding to FcγRIIIa and FcγRIIb is desired.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "heavy constant region" herein is meant the CH1-hinge-CH2-CH3 portion of an antibody, generally from human IgG1, IgG2 or IgG4.

By "target antigen" as used herein is meant the molecule that is bound specifically by the variable region of a given antibody. In the present case, the target antigen is a BTLA protein.

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

By "position" as used herein is meant a location in the sequence of a protein. Positions may be numbered sequentially, or according to an established format, for example the EU index for antibody numbering.

By "residue" as used herein is meant a position in a protein and its associated amino acid identity. For example, Asparagine 297 (also referred to as Asn297 or N297) is a residue at position 297 in the human antibody IgG1.

The antibodies of the present invention are generally recombinant. "Recombinant" means the antibodies are generated using recombinant nucleic acid techniques in exogenous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

An example of an implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by Intelli-Genetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In some embodiments, the $K_D$ of an antibody is determined by Bio-Layer Interferometry. In some embodiments, the $K_D$ value is measured with the immobilized. In other embodiments, the $K_D$ value is measured with the antibody (e.g., parent mouse antibody, chimeric antibody, or humanized antibody variants) immobilized. In certain embodiments, the $K_D$ value is measured in a bivalent binding mode. In other embodiments, the $K_D$ value is measured in a monovalent binding mode.

A "disease" includes a state of health of an animal, including a human, wherein the animal cannot maintain homeostasis, and wherein if the disease is not ameliorated then the animal's health continues to deteriorate.

In contrast, a "disorder" in an animal, including a human, includes a state of health in which the animal is able to maintain homeostasis, but in which the animal's state of health is less favorable than it would be in the absence of the disorder. Left untreated, a disorder does not necessarily cause a further decrease in the animal's state of health.

The terms "treatment", "treating", "treat", and the like, refer to obtaining a desired pharmacologic and/or physiologic effect. The effect may be prophylactic in terms of completely or partially preventing a disease or symptom thereof or reducing the likelihood of a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

As used herein, the term "mammal" refers to any mammal, including, but not limited to, mammals of the order Rodentia, such as mice and hamsters, and mammals of the order Logomorpha, such as rabbits. In some embodiments, the mammals are from the order Carnivora, including felines (cats) and canines (dogs). In some embodiments, the mammals are from the order Artiodactyla, including bovines (cows) and swines (pigs) or of the order Perssodactyla, including Equines (horses). It is most preferred that the mammals are of the order Primates, Ceboids, or Simoids (monkeys) or of the order Anthropoids (humans and apes). In some embodiments, the mammal is a human. In some embodiments, the mammal is cynomolgus monkey.

The term "regression," as well as words stemming therefrom, as used herein, does not necessarily imply 100% or complete regression. Rather, there are varying degrees of regression of which one of ordinary skill in the art recognizes as having a potential benefit or therapeutic effect. In this respect, the disclosed methods can provide any amount of any level of regression of a cancer in a mammal. Furthermore, the regression provided by the inventive method can include regression of one or more conditions or symptoms of the disease, e.g., a cancer. Also, for purposes herein, "regression" can encompass delaying the onset of the disease, delaying the onset of a symptom, and/or delaying the onset of a condition thereof. With respect to progressive diseases and disorders, "regression" can encompass slowing the progression of the disease or disorder, slowing the progression of a symptom of the disease or disorder, and/or slowing the progression of a condition thereof.

An "effective amount" or "therapeutically effective amount" of a composition includes that amount of the composition which is sufficient to provide a beneficial effect to the subject to which the composition is administered. An "effective amount" of a delivery vehicle includes that amount sufficient to effectively bind or deliver a composition.

By "individual" or "host" or "subject" or "patient" is meant any mammalian subject for whom diagnosis, treatment, or therapy is desired, particularly humans. Other subjects may include cynomolgus monkey, cattle, dogs, cats, guinea pigs, rabbits, rats, mice, horses, and so on.

The term "in combination with" as used herein refers to uses where, for example, a first therapy is administered during the entire course of administration of a second therapy; where the first therapy is administered for a period of time that is overlapping with the administration of the second therapy, e.g., where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

"Encoding" includes the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if, for example, transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

The term "operably linked" as used herein includes a polynucleotide in functional relationship with a second polynucleotide, e.g., a single-stranded or double-stranded nucleic acid moiety comprising the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. The order specified when indicating operably linkage is not important. For example, the phrases: "the promoter is operably linked to the nucleotide sequence" and "the nucleotide sequence is operably linked to the promoter" are used interchangeably herein and are considered equivalent. In some cases, when the nucleic acid encoding the desired protein further comprises a promoter/regulatory sequence, the promoter/regulatory sequence is positioned at the 5' end of the desired protein coding sequence such that it drives expression of the desired protein in a cell.

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

The term "recombinant," as applied to a polynucleotide means the polynucleotide is the product of various combinations of cloning, restriction or ligation steps, and other procedures resulting in a construct distinct and/or different from a polynucleotide found in nature. The terms respectively include replicates of the original polynucleotide construct and progeny of the original virus construct.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors.

A "vector" is capable of transferring gene sequences to target-cells. Typically, "vector construct," "expression vector," and "gene transfer vector," mean any nucleic acid construct capable of directing the expression of a gene of interest and which can transfer gene sequences to target-cells, which can be accomplished by genomic integration of all or a portion of the vector, or transient or inheritable maintenance of the vector as an extrachromosomal element. Thus, the term includes cloning, and expression vehicles, as well as integrating vectors.

The term "regulatory element" as used herein includes a nucleotide sequence which controls some aspect of the expression of nucleic acid sequences. Examples of regulatory elements illustratively include an enhancer, an internal ribosome entry site (IRES), an intron, an origin of replication, a polyadenylation signal (pA), a promoter, an enhancer, a transcription termination sequence, and an upstream regulatory domain, which contribute to the replication, transcription, and/or post-transcriptional processing of a nucleic acid sequence. In cases, regulatory elements can also include cis-regulatory DNA elements as well as transposable elements (TEs). Those of ordinary skill in the art are capable of selecting and using these and other regulatory elements in an expression construct with no more than routine experimentation. Expression constructs can be generated using a genetic recombinant approach or synthetically using well-known methodology.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

The statement that an amino acid residue is "phosphorylated" used herein means that a phosphate group is ester-linked to the side chain of the amino acid residue. Typical amino acid residues that may be phosphorylated include serine (Ser), threonine (Thr), and tyrosine (Tyr).

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

Various aspects of the invention are set forth below in sections; however, aspects of the invention described in one particular section are not to be limited to any particular section.

I. Antibodies

The present disclosure provides novel anti-BTLA antibodies. Such antibodies can bind human and/or cynomolgus BTLA. Table 1 lists peptide sequences of heavy chain variable regions and light chain variable regions that, in combination as designated in Table 1, can bind to human and/or cynomolgus BTLA. In some embodiments, the heavy chain variable region and the light chain variable region are arranged in an Fab format. In some embodiments, the heavy chain variable region and the light chain variable region are fused together to from an scFv.

TABLE 1

| Clone | Heavy chain variable region amino acid sequence | Light chain variable region amino acid sequence |
| --- | --- | --- |
| 18-E7A | EVQLLESGGGLVQPGGSLRLSC AASGFTSSGYAMSWVRQAPGK GLEWVSGISGSGGGTYYADSVK GRFTISRDNSKNTLYLQMNNLR AEDTAVYYCAKGDYYGSGSYP LFDYWGQGTLVIVSSX SEQ ID NO: 1 CDR1 (SEQ ID NO: 47)- GFTSSGYA CDR2 (SEQ ID NO: 48)- ISGSGGGT CDR3 (SEQ ID NO: 49)- AKGDYYGSGSYPLFDY | AIQLTQSPSSLSASVGDRVTIT CRASQGISSALAWYQQKPGK APKLLISDASSLESGVPSRFSG SGSGTDFTLTISSLQPEDFATF YCQQFNNYPPTFGPGTKVDIK SEQ ID NO: 2 CDR1 (SEQ ID NO: 50)- QGISSA CDR2 (SEQ ID NO: 51)- DAS CDR3 (SEQ ID NO: 52)- QQFNNYPPT |
| 3-A18A | QVQLQESGPGLVKPSETLSLTCT VSGGSISSYYWSWIRQPPGKGLE WIGYIYYSGTTNYNPSLKSRVTI SVDTSKNQFSLKLSSVTAADTA VYYCARVVLYSTGWSFDYWGQ GTLVTVSSX SEQ ID NO: 3 CDR1 (SEQ ID NO: 53)- GGSISSYY CDR2 (SEQ ID NO: 54)- IYYSGTT CDR3 (SEQ ID NO: 55)- ARVVLYSTGWSFDY | EIVMTQSPATLSLSPGERATLS CRASQSVSSSYLSWYQQRPG QAPRLLIYGTSTRATGIPARFS GSGSGTDFTLTISSLQPEDFAV YYCQQDYNLPLTFGGGTKVE IK SEQ ID NO: 4 CDR1 (SEQ ID NO: 56)- QSVSSSY CDR2 (SEQ ID NO: 57)- GTS CDR3 (SEQ ID NO: 58)- QQDYNLPLT |
| 10-P12A | QVQLQESGPGLVKPSETLSLTCT VSGGSISSYYWSWIRQPPGKGLE WIGYIYYSGSTNYNPSLKSRVTI SVDTSKNQFSLKLSSVTAADTA VYYCARVVLYSSGWSFDYWGQ GTLVTVSSX SEQ ID NO: 5 CDR1 (SEQ ID NO: 59)- GGSISSYY CDR2 (SEQ ID NO: 60)- IYYSGST CDR3 (SEQ ID NO: 61)- ARVVLYSSGWSFDY | EIVMTQSPATLSLSPGERATLS CRASQSFSSSYLSWYQQKPG QAPRLLIYGASTRATGIPARFS GSGSGTDFTLTISSLQPEDFAV YYCQQDYNLPLTFGGGTKVE IK SEQ ID NO: 6 CDR1 (SEQ ID NO: 62)- QSFSSSY CDR2 (SEQ ID NO: 63)- GAS CDR3 (SEQ ID NO: 64)- QQDYNLPLT |

TABLE 1-continued

| Clone | Heavy chain variable region amino acid sequence | Light chain variable region amino acid sequence |
|---|---|---|
| 2-M12A | QVQLQESGPGLVKPSETLSLTCT VSGGSISHYYWSWIRQPPGKGL EWIGYIYYSGSTNYNPSLKSRVT ISVDTSKNQFSLKLSSVTAADTA VYYCARVVLYSSGWSFDYWGQ GTLVTVSSX<br>SEQ ID NO: 7<br>CDR1 (SEQ ID NO: 65)-GGSISHYY<br>CDR2 (SEQ ID NO: 66)-IYYSGST<br>CDR3 (SEQ ID NO: 67)-ARVVLYSSGWSFDY | EIVMTQSPATLSLSPGERATLS CRASQSVSSSYLSWYQQKPG QAPRLLIYGASTRATGIPARFS GSGSGTDFTLTISSLQPEDFAV YYCQQDYNLPLTFGGGTKVE IK<br>SEQ ID NO: 8<br>CDR1 (SEQ ID NO: 68)-QSVSSSY<br>CDR2 (SEQ ID NO: 69)-GAS<br>CDR3 (SEQ ID NO: 70)-QQDYNLPLT |
| 1-G20A | QVQLQESGPGLVKPSETLSLTCT VSGGSISSYYWSWIRQPPGKGLE WIGYIYYSGSTNYNPSLKSRVTI SVDTSKNQFSLKLSSVTAADTA VYYCARVMVFSSGWYFDYWG QGTLVTVSSX<br>SEQ ID NO: 9<br>CDR1 (SEQ ID NO: 71)-GGSISSYY<br>CDR2 (SEQ ID NO: 72)-IYYSGST<br>CDR3 (SEQ ID NO: 73)-ARVMVFSSGWYFDY | EIVMTQSPATLSLSPGERATLS CRASQNITSSYLSWYQQKPG QSPRLLIYDASTRATGIPARFS GSGSGTDFTLTISSLQPEDFAV YYCQQDYNLPLTFGGGTKVE IK<br>SEQ ID NO: 10<br>CDR1 (SEQ ID NO: 74)-QNITSSY<br>CDR2 (SEQ ID NO: 75)-DAS<br>CDR3 (SEQ ID NO: 76)-QQDYNLPLT |
| 12-F16A | QVQLQESGPGLVKPSETLSLTCT VSGGSISSHYWSWIRQPPGKGLE WIGYIYYSGNTKYNPSLKSRVTI SVDTSKNQFSLKLTSVTAADTA VYYCARVGPGSHYNPHNWFDP WGQGTLVTVSSX<br>SEQ ID NO: 11<br>CDR1 (SEQ ID NO: 77)-GGSISSHY<br>CDR2 (SEQ ID NO: 78)-IYYSGNT<br>CDR3 (SEQ ID NO: 79)-ARVGPGSHYNPHNWFDP | EIVMTQSPATLSLSPGERATLS CRASQTVTSSYLSWYQQKPG QAPRLLIYGASTRATGFPARF SVSGSGTDFTLTISSLQPEDFA VYYCQQDYNLPWTFGQGTK VEIK<br>SEQ ID NO: 12<br>CDR1 (SEQ ID NO: 80)-QTVTSSY<br>CDR2 (SEQ ID NO: 81)-GAS<br>CDR3 (SEQ ID NO: 82)-QQDYNLPWT |
| 11-N12A | QVQLVQSGAEVKKPGASVKVS CKASGYTFTNYGIIWVRQAPGQ GLEWMGWISAYNGNTNYAQKL QGRVTMTTDTSTSTAYMELRTL RSDDTAVYYCARDYYSSGSYG GWFDPWGQGTLVTVSSX<br>SEQ ID NO: 13<br>CDR1 (SEQ ID NO: 83)-GYTFTNYG<br>CDR2 (SEQ ID NO: 84)-ISAYNGNT<br>CDR3 (SEQ ID NO: 85)-ARDYYSSGSYGGWFDP | QLVLTQSPSASASLGASVKLT CTLSSGHSSYAIAWHQQQPEK GPRYLMKLNSDGSHSKGDGI PDRFSGSSSGAERYLTISSLQS VDEADYYCQTWGTGIRVFGG GTKLTVL<br>SEQ ID NO: 14<br>CDR1 (SEQ ID NO: 86)-SGHSSYA<br>CDR2 (SEQ ID NO: 87)-LNSDGSH<br>CDR3 (SEQ ID NO: 88)-QTWGTGIRV |
| 18-K8A | QVQLVQSGAEVKKPGASVKVS CKASGYTFTNYGIIWVRQAPGQ GLEWMGWISAYNGNTNYAQKL QGRVTMTTDTSTSTAYMELRSL RSDDTAVYYCARDYYSSGSYG GWFDPWGQGTLVTVSS<br>SEQ ID NO: 15<br>CDR1 (SEQ ID NO: 89)-GYTFTNYG<br>CDR2 (SEQ ID NO: 90)-ISAYNGNT<br>CDR3 (SEQ ID NO: 91)-ARDYYSSGSYGGWFDP | QLVLTQSPSASASLGASVKLT CTLSSGHSSYAIAWHQQQPEK GPRYLMKLNSDGSHSKGDGI PDRFSGSSSGAERYLTISSLQS VDEADYYCQTWGTGIRVFGG GTKLTVL<br>SEQ ID NO: 16<br>CDR1 (SEQ ID NO: 92)-SGHSSYA<br>CDR2 (SEQ ID NO: 93)-LNSDGSH<br>CDR3 (SEQ ID NO: 94)-QTWGTGIRV |
| 17-L17A | EVQLLESGGGLVQPGGSLRLSC AASGFTSSSYAMSWVRQAPGK GLEWVSGISGSGDSTYYADSVK GRFIISRDNSKNTLYLQMNSLRA EDTAVYYCAKGDYYGSGSYPLF | AIQLTQSPSSLSASVGDRVTIT CRASQGISSALAWYQQKPGK APKLLISDASSLESGVPSRFSG GGSGTDFTLTISSLQPEDFATY YCQQFYNYPPTFGPGTKVDII |

TABLE 1-continued

| Clone | Heavy chain variable region amino acid sequence | Light chain variable region amino acid sequence |
|---|---|---|
| | DYWGQGTRVTVSSX SEQ ID NO: 17 CDR1 (SEQ ID NO: 95)- GFTSSSYA CDR2 (SEQ ID NO: 96)- ISGSGDST CDR3 (SEQ ID NO: 97)- AKGDYYGSGSYPLFDY | SEQ ID NO: 18 CDR1 (SEQ ID NO: 98)- QGISSA CDR2 (SEQ ID NO: 99)- DAS CDR3 (SEQ ID NO: 100)- QQFYNYPPT |
| 16-I20A | QVQLQESGPGLVKPSETLSLTCT VSGGSISYYYWSWIRQPPGTGLE WIGYIYYSGSTKYNPSLKRRVTI SVDTSKNQFSLKLSSVTAADTA VYYCARIRGDSYGWDFDYWGQ GTLVTVSSX SEQ ID NO: 19 CDR1 (SEQ ID NO: 101)- GGSISYYY CDR2 (SEQ ID NO: 102)- IYYSGST CDR3 (SEQ ID NO: 103)- ARIRGDSYGWDFDY | EIVMTQSPATLSLSPGERATLS CRASQSISNNYLFWYQQKPG QAPRLLIYGASTRATGIPARFS GSGSGTDFTLTISSLQPEDFAV YYCQQDYNFPLTFGGGTKVEI K SEQ ID NO: 20 CDR1 (SEQ ID NO: 104)- QSISNNY CDR2 (SEQ ID NO: 105)- GAS CDR3 (SEQ ID NO: 106)- QQDYNFPLT |
| 15-C19A | QVQLQESGPGLVKPSETLSLTCT VSGGSISSYYWSWIRQPPGKGLE WIGYISYSGSTNYNPSLKSRVTIS ADTSKNQFSLKLSSVTAADTAV YYCARDFYYGMDVWGQGTTV TVSS SEQ ID NO: 21 CDR1 (SEQ ID NO: 107)- GGSISSYY CDR2 (SEQ ID NO: 108)- ISYSGST CDR3 (SEQ ID NO: 109)- ARDFYYGMDV | AIQLTQSPSSLSASVGDRVTIT CRASQGISSALAWYQQKPGK APKLLIYDASSLESGVPSRFSG SGSGTDFTLTISSLQPEDFATY YCHQFDYYPTFGGGTKVEIK SEQ ID NO: 22 CDR1 (SEQ ID NO: 110)- QGISSA CDR2 (SEQ ID NO: 111)- DAS CDR3 (SEQ ID NO: 112)- HQFDYYPT |
| 15-E14A | EVQLLESGGGSEQPGGSLRLSCA ASGFTSSSYAMSWVRLAPGKGL EWVSGISGSGGGTYYADSVKGR FTTSRDNSKNTLYLQMNSLRAE DTAVYYCTKGDYYGSGSYPLFD YWGQGTLVTVSSX SEQ ID NO: 23 CDR1 (SEQ ID NO: 113)- GFTSSSYA CDR2 (SEQ ID NO: 114)- ISGSGGT CDR3 (SEQ ID NO: 115)- TKGDYYGSGSYPLFDY | AIQLTQSPSSLSASVGDRVTIT CRASQGISSALAWYQQKPGK APKLLISDASSLESGVPSRFSG SGSGTDFTLTISSLQPEDFATY YCQQFNNYPPTFGPGTKVDIK SEQ ID NO: 24 CDR1 (SEQ ID NO: 116)- QGISSA CDR2 (SEQ ID NO: 117)- DAS CDR3 (SEQ ID NO: 118)- QQFNNYPPT |
| 16-H16A | QLQLQESGPGLVKPSETLSLTCT VSGDSISSSGYYWGWIRQPPGK GLEWIGSIYYSGSTHYNPSLKSR VTISVDSSKSQFSLKLSSVTAAD TAVYCCARHKVDSSGWPLDYW GQGTLVTVSSX SEQ ID NO: 25 CDR1 (SEQ ID NO: 119)- GDSISSSGYY CDR2 (SEQ ID NO: 120)- IYYSGST CDR3 (SEQ ID NO: 121)- ARHKVDSSGWPLDY | EIVMTQSPATLSLSPGERATLS CRASQSISSSCLSWYQQKPGQ APRLLIYDTSTRATGIPARFSG SGSGTDFTLTISSLQPEDFAVY YCQQDYNLPLTFGGGTKVEI K SEQ ID NO: 26 CDR1 (SEQ ID NO: 122)- QSISSSC CDR2 (SEQ ID NO: 123)- DTS CDR3 (SEQ ID NO: 124)- QQDYNLPLT |
| 12-08A | QVQLVESGGGVVQPGRSLRLSC AASGFTFSSYGMHWVRQAPGK GLEWVAVIWYNGSNRYYADSV KGRFTISRDNSKNTLYLQMNSL RAEDTAVYYCARDDVVRYFDW PLDYWGQGTLVTVSSX SEQ ID NO: 27 CDR1 (SEQ ID NO: 125)- GFTFSSYG CDR2 (SEQ ID NO: 126)- IWYNGSNR | AIQMTQSPSSLSASVGDRVTIT CRASQGIRNDLGWYQQKPGK APKVLIYAASSLQSGVPSRFS GSGSGTDFTLTISSLQPEDFAT YYCLQDYNYPWTFGQGTKV EIK SEQ ID NO: 28 CDR1 (SEQ ID NO: 128)- QGIRND CDR2 (SEQ ID NO: 129)- AAS |

TABLE 1-continued

| Clone | Heavy chain variable region amino acid sequence | Light chain variable region amino acid sequence |
|---|---|---|
| | CDR3 (SEQ ID NO: 127)-<br>ARDDVVRYFDWPLDY | CDR3 (SEQ ID NO: 130)-<br>LQDYNYPWT |
| 12-I8A | QVQLVESGGGVVQPGRSLRLSC<br>AASGFTFSNYGMHWVRQAPGK<br>GLEWVAVIWYNGSNKYYADSV<br>KGRFTISRDNSKNTLYLQMNSL<br>RAEDTAVYYCARDDVVRYFDW<br>PLDYWGQGTLVTVSSX<br>SEQ ID NO: 29<br>CDR1 (SEQ ID NO: 131)-<br>GFTFSNYG<br>CDR2 (SEQ ID NO: 132)-<br>IWYNGSNK<br>CDR3 (SEQ ID NO: 133)-<br>ARDDVVRYFDWPLDY | AIQMTQSPSSLSASVGDRVTIT<br>CRASQGIRNDLGWYQQKPGK<br>APKVLIYAASSLQSGVPSRFS<br>GSGSGTDFTLTISSLQPEDFAT<br>YYCLQDYNYPWTFGQGTKV<br>EIK<br>SEQ ID NO: 30<br>CDR1 (SEQ ID NO: 134)-<br>QGIRND<br>CDR2 (SEQ ID NO: 135)-<br>AAS<br>CDR3 (SEQ ID NO: 136)-<br>LQDYNYPWT |
| 8-M23A | QVQLQESGPGLVKPSETLSLTCT<br>VSGGSISSYYWSWIRQPPGKGLE<br>WIGYIYYSGSTNYNPSLKSRITIS<br>VDTSKNQFSLKLSSVTAADTAV<br>YYCARVILYSSGWSFDYWGQG<br>TLVTVSSX<br>SEQ ID NO: 31<br>CDR1 (SEQ ID NO: 137)-<br>GGSISSYY<br>CDR2 (SEQ ID NO: 138)-<br>IYYSGST<br>CDR3 (SEQ ID NO: 139)-<br>ARVILYSSGWSFDY | EIVMTQSPATLSLSPGERATLS<br>CRASQSVSSSYLSWYQQKPG<br>QAPRLLIYGASTRATGIPARFS<br>GSGSGTDFTLTISSLQPEDFAV<br>YYCQQDYNLPLTFGGGTKVE<br>IK<br>SEQ ID NO: 32<br>CDR1 (SEQ ID NO: 140)-<br>QSVSSSY<br>CDR2 (SEQ ID NO: 141)-<br>GAS<br>CDR3 (SEQ ID NO: 142)-<br>QQDYNLPLT |
| 1-F23A | QVQLQESGPGLVKPSETLSLTCT<br>VSGGSISSYYWSWIRQPPGKGLE<br>WIGYIYYSGSTNYNPSLKSRITIS<br>VDTSKNQFSLKLSSVTAADTAV<br>YYCARVILYSSGWSFDYWGQG<br>TLVTVSSX<br>SEQ ID NO: 33<br>CDR1 (SEQ ID NO: 143)-<br>GGSISSYY<br>CDR2 (SEQ ID NO: 144)-<br>IYYSGST<br>CDR3 (SEQ ID NO: 145)-<br>ARVILYSSGWSFDY | EIVMTQSPATLSLSPGERATLS<br>CRASQSVSSSYLSWYQQKPG<br>QAPRLLIYDASTRATGIPARFS<br>GSGSGTDFTLTISSLQPEDFAV<br>YYCQQDYNLPLTFGGGTKVE<br>IK<br>SEQ ID NO: 34<br>CDR1 (SEQ ID NO: 146)-<br>QSVSSSY<br>CDR2 (SEQ ID NO: 147)-<br>DAS<br>CDR3 (SEQ ID NO: 148)-<br>QQDYNLPLT |
| 13-F7A | EVQLLESGGGLVQPGGSLRLSC<br>AASGFTSSSYGMSWVRQAPGK<br>GLEWVSGISGSGGTYYADSVK<br>GRFTISRDNSKNTLYLQMNSLR<br>AEDTAVYYCAKGDYYGSGSYP<br>LFDYWGQGTLVTVSSX<br>SEQ ID NO: 35<br>CDR1 (SEQ ID NO: 149)-<br>GFTSSSYG<br>CDR2 (SEQ ID NO: 150)-<br>ISGSGGT<br>CDR3 (SEQ ID NO: 151)-<br>AKGDYYGSGSYPLFDY | AIQLTQSPSSLSASVGDRVTIT<br>CRASQDISSALAWYQQKPGK<br>APKLLISDASSLESGVPSRFSG<br>SGSGTDFTLTISSLQPEDFATF<br>YCQQFNNYPPTFGPGTKVDIK<br>SEQ ID NO: 36<br>CDR1 (SEQ ID NO: 152)-<br>QDISSA<br>CDR2 (SEQ ID NO: 153)-<br>DAS<br>CDR3 (SEQ ID NO: 154)-<br>QQFNNYPPT |
| 11-F3A | EVQLLESGGGLVQPGGSLRLSC<br>AASGFTFSSYAMSWVRQAPGK<br>GLKWVSGISGSGGTYYADSVK<br>GRFTLSRDNSKNTLYLQMNSLR<br>AEDTAVYFCAKGDYYGSGSYPL<br>FDFWGQGTLVTVSS<br>SEQ ID NO: 37<br>CDR1 (SEQ ID NO: 155)-<br>GFTFSSYA<br>CDR2 (SEQ ID NO: 156)-<br>ISGSGGT<br>CDR3 (SEQ ID NO: 157)-<br>AKGDYYGSGSYPLFDF | AIQLTQSPSSLSASVGDRVTIT<br>CRASQGISSALAWYQQKPGK<br>APKLLIFDASSLESGVPSRFSG<br>SGSGTDFTLTISSLQPEDFATY<br>YCQQFNDYPPTFGPGTKLDIK<br>SEQ ID NO: 38<br>CDR1 (SEQ ID NO: 158)-<br>QGISSA<br>CDR2 (SEQ ID NO: 159)-<br>DAS<br>CDR3 (SEQ ID NO: 160)-<br>QQFNDYPPT |
| 20-E16A | QVQLQESGPGLVKPSETLSLTCT<br>VSGGSISSYYWTWIRQPPGKGLE<br>WIGHISYSGSTHYNPSLKSRFTIS | AIQLTQSPSSLSASVGDRVTIT<br>CRASQDISNTVAWYQQNPGK<br>APKLLIYDASSLESGVSSRFSG |

TABLE 1-continued

| Clone | Heavy chain variable region amino acid sequence | Light chain variable region amino acid sequence |
|---|---|---|
|  | ADTSKNRFSLKLSSVTAADTAV YYCARDGYYALDVWGQGTTVT VSS SEQ ID NO: 39 CDR1 (SEQ ID NO: 161)- GGSISSYY CDR2 (SEQ ID NO: 162)- ISYSGST CDR3 (SEQ ID NO: 163)- ARDGYYALDV | SGSGTDFTLTISSLQPEDFATY YCQQFNNYPYTFGQGTKLEIK SEQ ID NO: 40 CDR1 (SEQ ID NO: 164)- QDISNT CDR2 (SEQ ID NO: 165)- DAS CDR3 (SEQ ID NO: 166)- QQFNNYPYT |
| 16-K19A | EVQLLESGGGLEQPGGSLRLSC AASGFTSSSYAMSWVRQAPGK GLEWVSGISGSGGGTYYADSVK GRFSTSRDNSKNTLYLQMNSLR AEDTAVYYCAKGDYYGSGSYP LFDYWGQGTLVTVSS SEQ ID NO: 41 CDR1 (SEQ ID NO: 167)- GFTSSSYA CDR2 (SEQ ID NO: 168)- ISGSGGGT CDR3 (SEQ ID NO: 169)- AKGDYYGSGSYPLFDY | AIQLTQSPSSLSASVGDRVTIT CRASQGISSALAWYQQKPGK PPKLLISDASSLESGVPSRFSG SGSGTDFTLTISSLQPEDFATY YCQQFNNYPPTFGPGTKVDIK SEQ ID NO: 42 CDR1 (SEQ ID NO: 170)- QGISSA CDR2 (SEQ ID NO: 171)- DAS CDR3 (SEQ ID NO: 172)- QQFNNYPPT |

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:2.

In some embodiments, the anti-BTLA antibodies include a vhCDR1 comprising SEQ ID NO:47, a vhCDR2 comprising SEQ ID NO:48, a vhCDR3 comprising SEQ ID NO:49, a vlCDR1 comprising SEQ ID NO:50, a vlCDR2 comprising SEQ ID NO:51, and a vlCDR3 comprising SEQ ID NO:52. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:3 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:4.

In some embodiments, the anti-BTLA antibodies include a vhCDR1 comprising SEQ ID NO:53, a vhCDR2 comprising SEQ ID NO:54, a vhCDR3 comprising SEQ ID NO:55, a vlCDR1 comprising SEQ ID NO:56, a vlCDR2 comprising SEQ ID NO:57, and a vlCDR3 comprising SEQ ID NO:58. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:5 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:6.

In some embodiments, the anti-BTLA antibodies include a vhCDR1 comprising SEQ ID NO:59, a vhCDR2 comprising SEQ ID NO:60, a vhCDR3 comprising SEQ ID NO:61, a vlCDR1 comprising SEQ ID NO:62, a vlCDR2 comprising SEQ ID NO:63, and a vlCDR3 comprising SEQ ID NO:64. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:7 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:8.

In some embodiments, the anti-BTLA antibodies include a vhCDR1 comprising SEQ ID NO:65, a vhCDR2 comprising SEQ ID NO:66, a vhCDR3 comprising SEQ ID NO:67, a vlCDR1 comprising SEQ ID NO:68, a vlCDR2 comprising SEQ ID NO:69, and a vlCDR3 comprising SEQ ID NO:70. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:9 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:10.

In some embodiments, the anti-BTLA antibodies include a vhCDR1 comprising SEQ ID NO:71, a vhCDR2 comprising SEQ ID NO:72, a vhCDR3 comprising SEQ ID NO:73, a vlCDR1 comprising SEQ ID NO:74, a vlCDR2 comprising SEQ ID NO:75, and a vlCDR3 comprising SEQ ID NO:76. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:11 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:12.

In some embodiments, the anti-BTLA antibodies that include a vhCDR1 comprising SEQ ID NO:77, a vhCDR2 comprising SEQ ID NO:78, a vhCDR3 comprising SEQ ID NO:79, a vlCDR1 comprising SEQ ID NO:80, a vlCDR2 comprising SEQ ID NO:81, and a vlCDR3 comprising SEQ ID NO:82. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:13 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:14.

In some embodiments, the anti-BTLA antibodies that include a vhCDR1 comprising SEQ ID NO:83, a vhCDR2 comprising SEQ ID NO:84, a vhCDR3 comprising SEQ ID NO:85, a vlCDR1 comprising SEQ ID NO:86, a vlCDR2 comprising SEQ ID NO:87, and a vlCDR3 comprising SEQ ID NO:88. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:15 and a light chain variable region having an amino acid sequence at least 80% (e.g., 80%, 81%, 82%, 83%, 84%, 85%, 86%, 8'7%, 88%, 89%, 90%, 91%, 92%, 93%, 94%, 95%, 96%, 97%, 98%, 99%, or 100%) identical to SEQ ID NO:16.

In some embodiments, the anti-BTLA antibodies that include a vhCDR1 comprising SEQ ID NO:89, a vhCDR2 comprising SEQ ID NO:90, a vhCDR3 comprising SEQ ID NO:91, a vlCDR1 comprising SEQ ID NO:92, a vlCDR2 comprising SEQ ID NO:93, and a vlCDR3 comprising SEQ ID NO:94. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:17 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:18.

In some embodiments, the anti-BTLA antibodies include a vhCDR1 comprising SEQ ID NO:95, a vhCDR2 comprising SEQ ID NO:96, a vhCDR3 comprising SEQ ID NO:97, a vlCDR1 comprising SEQ ID NO:98, a vlCDR2 comprising SEQ ID NO:99, and a vlCDR3 comprising SEQ ID NO:100. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:19 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:20.

In some embodiments, the anti-BTLA antibodies include a vhCDR1 comprising SEQ ID NO:101, a vhCDR2 comprising SEQ ID NO:102, a vhCDR3 comprising SEQ ID NO:103, a vlCDR1 comprising SEQ ID NO:104, a vlCDR2 comprising SEQ ID NO:105, and a vlCDR3 comprising SEQ ID NO:106. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:21 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:22.

In some embodiments, the anti-BTLA antibodies include a vhCDR1 comprising SEQ ID NO:107, a vhCDR2 comprising SEQ ID NO:108, a vhCDR3 comprising SEQ ID NO:109, a vlCDR1 comprising SEQ ID NO:110, a vlCDR2 comprising SEQ ID NO:111, and a vlCDR3 comprising SEQ ID NO:112. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:23 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:24.

In some embodiments, the anti-BTLA antibodies include a vhCDR1 comprising SEQ ID NO:113, a vhCDR2 comprising SEQ ID NO:114, a vhCDR3 comprising SEQ ID NO:115, a vlCDR1 comprising SEQ ID NO:116, a vlCDR2 comprising SEQ ID NO:117, and a vlCDR3 comprising SEQ ID NO:118. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:25 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:26.

In some embodiments, the anti-BTLA antibodies include a vhCDR1 comprising SEQ ID NO:119, a vhCDR2 comprising SEQ ID NO:120, a vhCDR3 comprising SEQ ID NO:121, a vlCDR1 comprising SEQ ID NO:122, a vlCDR2 comprising SEQ ID NO:123, and a vlCDR3 comprising SEQ ID NO:124. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:27 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:28.

In some embodiments, the anti-BTLA antibodies include a vhCDR1 comprising SEQ ID NO:125, a vhCDR2 comprising SEQ ID NO:126, a vhCDR3 comprising SEQ ID NO:127, a vlCDR1 comprising SEQ ID NO:128, a vlCDR2 comprising SEQ ID NO:129, and a vlCDR3 comprising SEQ ID NO:130. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:29 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:30.

In some embodiments, the anti-BTLA antibodies include a vhCDR1 comprising SEQ ID NO:131, a vhCDR2 comprising SEQ ID NO:132, a vhCDR3 comprising SEQ ID NO:133, a vlCDR1 comprising SEQ ID NO:134, a vlCDR2 comprising SEQ ID NO:135, and a vlCDR3 comprising SEQ ID NO:136. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:31 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:32.

In some embodiments, the anti-BTLA antibodies include a vhCDR1 comprising SEQ ID NO:137, a vhCDR2 comprising SEQ ID NO:138, a vhCDR3 comprising SEQ ID NO:139, a vlCDR1 comprising SEQ ID NO:140, a vlCDR2 comprising SEQ ID NO:141, and a vlCDR3 comprising SEQ ID NO:142. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:33 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:34.

In some embodiments, the anti-BTLA antibodies include a vhCDR1 comprising SEQ ID NO:143, a vhCDR2 comprising SEQ ID NO:144, a vhCDR3 comprising SEQ ID NO:145, a vlCDR1 comprising SEQ ID NO:146, a vlCDR2 comprising SEQ ID NO:147, and a vlCDR3 comprising SEQ ID NO:148. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:35 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:36.

In some embodiments, the anti-BTLA antibodies include a vhCDR1 comprising SEQ ID NO:149, a vhCDR2 comprising SEQ ID NO:150, a vhCDR3 comprising SEQ ID NO:151, a vlCDR1 comprising SEQ ID NO:152, a vlCDR2 comprising SEQ ID NO:153, and a vlCDR3 comprising SEQ ID NO:154. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:37 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:38.

In some embodiments, the anti-BTLA antibodies include a vhCDR1 comprising SEQ ID NO:155, a vhCDR2 comprising SEQ ID NO:156, a vhCDR3 comprising SEQ ID NO:157, a vlCDR1 comprising SEQ ID NO:158, a vlCDR2 comprising SEQ ID NO:159, and a vlCDR3 comprising SEQ ID NO:160. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:39 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:40.

In some embodiments, the anti-BTLA antibodies include a vhCDR1 comprising SEQ ID NO:161, a vhCDR2 comprising SEQ ID NO:162, a vhCDR3 comprising SEQ ID NO:163, a vlCDR1 comprising SEQ ID NO:164, a vlCDR2 comprising SEQ ID NO:165, and a vlCDR3 comprising SEQ ID NO:166. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In some embodiments, the anti-BTLA antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:41 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:42.

In some embodiments, the anti-BTLA antibodies include a vhCDR1 comprising SEQ ID NO:167, a vhCDR2 comprising SEQ ID NO:168, a vhCDR3 comprising SEQ ID NO:169, a vlCDR1 comprising SEQ ID NO:170, a vlCDR2 comprising SEQ ID NO:171, and a vlCDR3 comprising SEQ ID NO:172. In some embodiments, one or more of such 6 CDRs have from 1, 2, 3, 4 or 5 amino acid modifications. In further embodiments, a single CDR contains 1 or 2 amino acid substitutions, and the modified anti-BTLA antibodies retain binding to human and/or cynomolgus BTLA.

In addition to the sequence variants described herein in the heavy chain and light chain variable regions and/or CDRs, changes in the framework region(s) of the heavy and/or light variable region(s) can be made. In some embodiment, variants in the framework regions (e.g., excluding the CDRs) retain at least about 80, 85, 90 or 95% identity to a germline sequence. Table 2 lists the germline gene alleles encoding the anti-BTLA antibodies described herein. Variants can be made to retain at least about 80, 85, 90 or 95% identity to any one of the light chain V-GENE, light chain J-GENE, heavy chain V-GENE, heavy chain J-GENE, and heavy chain D-GENE alleles.

TABLE 2

| Clone | Light chain V-GENE allele | Light chain J-GENE allele | Heavy chain V-GENE allele | Heavy chain J-GENE allele | Heavy chain D-GENE allele |
|---|---|---|---|---|---|
| 18-E7A | IGKV1D-13*01 F | IGKJ3*01 F | IGHV3-23*01 F | IGHJ4*02 F | IGHD3-10*01 F |
| 3-A18A | IGKV3D-7*01 F | IGKJ4*01 F | IGHV4-59*01 F | IGHJ4*02 F | IGHD6-19*01 F |
| 10-P12A | IGKV3D-7*01 F | IGKJ4*01 F | IGHV4-59*01 F | IGHJ4*02 F | IGHD6-19*01 F |
| 2-M12A | IGKV3D-7*01 F | IGKJ4*01 F | IGHV4-59*01 F | IGHJ4*02 F | IGHD6-19*01 F |
| 1-G20A | IGKV3D-7*01 F | IGKJ4*01 F | IGHV4-59*01 F | IGHJ4*02 F | IGHD6-19*01 F |
| 12-F16A | IGKV3D-7*01 F | IGKJ1*01 F | IGHV4-59*01 F | IGHJ5*02 F | IGHD3-10*01 F |
| 11-N12A | IGLV4-69*01 F | IGLJ3*02 F | IGHV1-18*01 F | IGHJ5*02 F | IGHD3-10*01 F |
| 18-K8A | IGLV4-69*01 F | IGLJ3*02 F | IGHV1-18*01 F | IGHJ5*02 F | IGHD3-10*01 F |
| 17-L17A | IGKV1D-13*01 F | IGKJ3*01 F | IGHV3-23*01 F | IGHJ4*02 F | IGHD3-10*01 F |
| 16-I20A | IGKV3D-7*01 F | IGKJ4*01 F | IGHV4-59*01 F | IGHJ4*02 F | IGHD5-18*01 F |
| 15-C19A | IGKV1D-13*01 F | IGKJ4*01 F | IGHV4-59*03 F | IGHJ6*02 F | NA |
| 15-E14A | IGKV1D-13*01 F | IGKJ3*01 F | IGHV3-23*01 F | IGHJ4*02 F | IGHD3-10*01 F |
| 16-H16A | IGKV3D-7*01 F | IGKJ4*01 F | IGHV4-39*01 F | IGHJ4*02 F | IGHD6-19*01 F |
| 12-O8A | IGKV1-6*01 F | IGKJ1*01 F | IGHV3-33*01 F | IGHJ4*02 F | IGHD3-9*01 F |
| 12-I8A | IGKV1-6*01 F | IGKJ1*01 F | IGHV3-33*01 F | IGHJ4*02 F | IGHD3-9*01 F |
| 8-M23A | IGKV3D-7*01 F | IGKJ4*01 F | IGHV4-59*01 F | IGHJ4*02 F | IGHD6-19*01 F |
| 1-F23A | IGKV3D-7*01 F | IGKJ4*01 F | IGHV4-59*01 F | IGHJ4*02 F | IGHD6-19*01 F |
| 13-F7A | IGKV1D-13*01 F | IGKJ3*01 F | IGHV3-23*01 F | IGHJ4*02 F | IGHD3-10*01 F |
| 11-F3A | IGKV1D-13*01 F | IGKJ3*01 F | IGHV3-23*01 F | IGHJ4*02 F | IGHD3-10*01 F |
| 20-E16A | IGKV1D-13*01 F | IGKJ2*01 F | IGHV4-59*01 F | IGHJ6*02 F | NA |
| 16-K19A | IGKV1D-13*01 F | IGKJ3*01 F | IGHV3-23*01 F | IGHJ4*02 F | IGHD3-10*01 F |

In some embodiments, variations are made in the framework regions that retain at least 80, 85, 90 or 95% identity to the germline gene sequences described in the Table 2, while keeping 6 CDRs unchanged.

In some embodiments, variations are made in both the framework regions that retain at least 80, 85, 90 or 95% identity to the germline gene sequences described in the Table 2, and the 6 CDRs. The CDRs can have amino acid modifications (e.g., from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.).

By selecting amino acid sequences of CDRs and/or variable regions of a heavy chain and a light chain from those described herein and combining them with amino acid sequences of framework regions and/or constant regions of a heavy chain and a light chain of an antibody as appropriate, a person skilled in the art will be able to design an anti-BTLA antibody according to the present invention. The antibody framework regions and/or constant region (Fc domain) described in the current invention can derive from an antibody of any species, such as from human, rabbit, dog, cat, mouse, horse or monkey.

In some embodiments, the constant region is derived from human, and includes a heavy chain constant region derived from those of IgG, IgA, IgM, IgE, and IgD subtypes or variants thereof, and a light chain constant region derived from kappa or lambda subtypes or variants thereof. In some embodiments, the heavy chain constant region is derived from a human IgG, including IgG1, IgG2, IgG3, and IgG4. In some embodiments, the amino acid sequence of the heavy chain constant region is at least 80%, 85%, 90%, or 95% identical to a human IgG1, IgG2, IgG3, or IgG4 constant region. In some other embodiments, the amino acid sequence of the constant region is at least 80%, 85%, 90%, or 95% identical to an antibody constant region from another mammal, such as rabbit, dog, cat, mouse, horse or monkey. In some embodiments, the antibody constant region includes a hinge, a CH2 domain, a CH3 domain and optionally a CH1 domain.

In some embodiments, the antibodies described herein can be derived from a mixture from different species, e.g., forming a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system, as described for example in Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci, USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. Other humanization methods may involve the grafting of only parts of the CDRs, including but not limited to methods described in Tan et al., 2002, J. Immunol. 169:1119-1125; De Pascalis et al., 2002, J. Immunol. 169:3076-3084, all entirely incorporated by reference.

In some embodiments, the antibodies of the current invention comprise a heavy chain variable region derived from a particular human germline heavy chain immunoglobulin gene and/or a light chain variable region derived from a particular human germline light chain immunoglobulin gene. Such antibodies may contain amino acid differences as compared to the human germline sequences, due to, for example, naturally-occurring somatic mutations or intentional introduction of site-directed mutation. However, a humanized antibody typically is at least 80% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the human germline immunoglobulin gene. Typically, a humanized antibody derived from a particular human germline sequence will display no more than 10-20 amino acid differences from the amino acid sequence encoded by the human germline immunoglobulin gene. In certain cases, the humanized antibody may display no more than 5, or even no more than 4, 3, 2, or 1 amino acid difference from the amino acid sequence encoded by the germline immunoglobulin gene.

In some embodiments, the antibodies of the current disclosure are humanized and affinity matured, as is known in the art. Structure-based methods may be employed for humanization and affinity maturation, for example as described in U.S. Pat. No. 7,657,380. Selection based methods may be employed to humanize and/or affinity mature antibody variable regions, including but not limited to methods described in Wu et al., 1999, J. Mol. Biol. 294: 151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95:

8910-8915; Krauss et al., 2003, Protein Engineering 16(10): 753-759, all entirely incorporated by reference.

II. Characteristics of the Antibodies

In some embodiments, the anti-BTLA antibodies described herein bind to human and/or cynomolgus BTLA. In some embodiments, binding of the anti-BTLA antibodies to human and/or cynomolgus BTLA is measured by ELISA, such as the exemplary assay described in Example 1. In such embodiments, antibodies described herein display an EC50 that can range from 0.1-20 nM as measured by such assays. In some embodiments, binding of the anti-BTLA antibodies to human and/or cynomolgus BTLA is measured by FACS, such as the exemplary assay described in Example 2. In such embodiments, the antibodies described herein display an EC50 that ranges from 0.1-20 nM as measured by FACS. In further embodiments, the EC50 of antibodies described herein range from about 0.1-30, 1-28, 2-26, 3-24, 4-22, 5-20, 6-18, 7-16, 8-14, or 9-12 nM as measured by either ELISA or FACS.

In some embodiments, the anti-BTLA antibodies described herein bind human and/or cynomolgus BTLA with high affinities. The $K_D$ value can be measured with the antigen immobilized or with the antibody immobilized. The $K_D$ value can also be measured in a monovalent or a bivalent binding mode. For example, when measured by Bio-Layer interferometry, the $K_D$ values between the antibodies and human BTLA can be $1\times10^{-6}$M or less, $5\times10^{-7}$M or less, $2.5\times10^{-7}$M or less, $1\times10^{-7}$M or less, $5\times10^{-8}$M or less, $1\times10^{-8}$M or less, $1\times10^{-9}$M or less, or $1\times10^{-10}$ M or less. The $K_D$ value between the antibodies and cynomolgus BTLA can be $1\times10^{-6}$M or less, $5\times10^{-7}$M or less, $2.5\times10^{-7}$M or less, $1\times10^{-7}$M or less, $5\times10^{-8}$M or less, $2.5\times10^{-8}$M or less, $1\times10^{-8}$M or less, $5\times10^{-9}$M or less, $1\times10^{-9}$M or less, $5\times10^{-10}$M or less, or $1\times10^{-10}$ M or less. In some embodiments, the $K_D$ values between the antibodies and human BTLA range from 0.1 nM-1 µM, 0.25 nM-500 nM, 0.5 nM-250 nM, 1 nM-100 nM M, or 2 nM-50 nM. In some embodiments, the $K_D$ values between the antibodies and cynomolgus BTLA range from 0.1 nM-1 µM, 0.25 nM-500 nM, 0.5 nM-250 nM, 1 nM-100 nM M, or 2 nM-50 nM.

The binding affinities of the anti-BTLA antibodies described herein are compared with a BTLA monoclonal antibody 4C7 described in U.S. Pat. No. 8,563,694. In some embodiments, the anti-BTLA antibodies described herein have higher binding affinity to human BTLA than 4C7. In some embodiments, the anti-BTLA antibodies described herein have higher binding affinity to cynomolgus BTLA than 4C7. Table 7 lists exemplary Kis of some of the antibody clones as well as 4C7. One advantage of having a higher binding affinity than 4C7 is that the antibodies described herein can be more efficacious in modulating immune response and/or engaging anti-tumor immune response. Another advantage of having a higher binding affinity to cynomolgus BTLA than 4C7 is that preclinical monkey studies, such as pharmacokinetics, pharmacodynamics, safety, toxicity studies derived from these antibodies can have better predictive power than the studies using 4C7.

In some embodiments, the anti-BTLA antibodies display low immunogenicity when administered into human subjects. These antibodies can contain an Fc domain derived from human IgG1, human IgG2 or human IgG3. In some embodiments, these antibodies are humanized using the framework regions derived from human immunoglobulins.

Effects of the anti-BTLA antibodies on T cell function can be assayed using a variety of methods known in the art and described herein, including for example, by the method described in Example 5. Accordingly, the anti-BTLA antibodies can serve as BTLA antagonists or BTLA agonists.

In some embodiments, anti-BTLA antibodies described act as BTLA antagonists, and block interaction of BTLA with HVEM as well as HVEM-mediated suppression of T cell function. As a result, such anti-BTLA antibodies stimulate an immune response. Examples of such anti-BTLA antibodies include antibodies that contain a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:21, and a light chain variable region comprising amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:22; and/or a vhCDR1 comprising SEQ ID NO:107, a vhCDR2 comprising SEQ ID NO:108, a vhCDR3 comprising SEQ ID NO:109, a vlCDR1 comprising SEQ ID NO:110, a vlCDR2 comprising SEQ ID NO:111, and a vlCDR3 comprising SEQ ID NO:112. Alternatively, such anti-BTLA antibodies that act as antagonists can include a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:31 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:32; and/or vhCDR1 comprising SEQ ID NO:137, a vhCDR2 comprising SEQ ID NO:138, a vhCDR3 comprising SEQ ID NO:139, a vlCDR1 comprising SEQ ID NO:140, a vlCDR2 comprising SEQ ID NO:141, and a vlCDR3 comprising SEQ ID NO:142. Alternatively, such anti-BTLA antibodies that act as antagonists can include a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:35, and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:36; and/or a vhCDR1 comprising SEQ ID NO:149, a vhCDR2 comprising SEQ ID NO:150, a vhCDR3 comprising SEQ ID NO:151, a vlCDR1 comprising SEQ ID NO:152, a vlCDR2 comprising SEQ ID NO:153, and a vlCDR3 comprising SEQ ID NO:154.

In some other embodiments, anti-BTLA antibodies described herein act as BTLA agonists, and suppress immune cell functions, including pro-inflammatory T cell functions. As a result, such anti-BTLA antibodies suppress an immune response. For example, such anti-BTLA antibodies can include a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:19 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:20; and/or a vhCDR1 comprising SEQ ID NO:101, a vhCDR2 comprising SEQ ID NO:102, a vhCDR3 comprising SEQ ID NO:103, a vlCDR1 comprising SEQ ID NO:104, a vlCDR2 comprising SEQ ID NO:105, and a vlCDR3 comprising SEQ ID NO:106. Alternatively, such anti-BTLA antibodies can include a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:25 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:26; and/or a vhCDR1 comprising SEQ ID NO:119, a vhCDR2 comprising SEQ ID NO:120, a vhCDR3 comprising SEQ ID NO:121, a vlCDR1 comprising SEQ ID NO:122, a vlCDR2 comprising SEQ ID NO:123, and a vlCDR3 comprising SEQ ID NO:124. Alternatively, such anti-BTLA antibodies that act as agonists can include a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:29 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to comprising SEQ ID NO:30; and/or a vhCDR1 comprising SEQ ID NO:131, a vhCDR2 comprising SEQ ID NO:132, a vhCDR3 comprising SEQ ID NO:133, a vlCDR1 comprising SEQ ID NO:134, a vlCDR2 comprising SEQ ID NO:135, and a vlCDR3 comprising SEQ ID NO:136.

III. Nucleic Acids of the Invention

Nucleic acids encoding the anti-BTLA antibodies described herein are also provided, as well as expression vectors containing such nucleic acids and host cells transformed with such nucleic acids and/or expression vectors. As will be appreciated by those in the art, the protein sequences depicted herein can be encoded by any number of possible nucleic acid sequences due to the degeneracy of the genetic code. Table 3 gives exemplary nucleic acids encoding the heavy chain variable region and light chain variable region of the antibodies described herein.

TABLE 3

| Clone | Heavy chain variable region nucleic acid sequence | Light chain variable region nucleic acid sequence |
|---|---|---|
| 18-E7A | GAGGTGCAGTTGTTGGAGTCTG GGGGAGGCTTGGTACAGCCTGG GGGGTCCCTGAGACTCTCCTGTG CAGCCTCTGGATTCACCTCTAGC GGCTATGCCATGAGCTGGGTCC GCCAGGCTCCAGGGAAGGGGCT GGAGTGGGTCTCAGGTATTAGT GGTAGTGGTGGTGGCACATACT ACGCAGACTCCGTGAAGGGCCG GTTCACCATCTCCAGAGACAATT CCAAGAACACACTGTATCTGCA AATGAACAACCTGAGAGCCGAG GACACGGCCGTATATTACTGTGC GAAAGGGGATTACTATGGTTCG GGGAGTTATCCGCTTTTTGACTA CTGGGGCCAGGGAACCCTGGTC ATCGTCTCCTCAG SEQ ID NO: 185 | GCCATCCAGTTGACCCAGTCT CCATCCTCCCTGTCTGCATCTG TAGGAGACAGAGTCACCATCA CTTGCCGGGCAAGTCAGGGCA TTAGCAGTGCTTTAGCCTGGT ATCAGCAGAAACCAGGGAAA GCTCCTAAGCTCCTGATCTCT GATGCCTCCAGTTTGGAAAGT GGGGTCCCATCAAGGTTCAGC GGCAGTGGATCTGGGACAGAT TTCACTCTCACCATCAGCAGC CTGCAACCTGAAGATTTTGCA ACTTTTTACTGTCAACAGTTTA ATAATTACCCTCCCACTTTCG GCCCTGGGACCAAAGTGGATA TCAAA SEQ ID NO: 186 |
| 3-A18A | CAGGTGCAGCTGCAGGAGTCGG GCCCAGGACTGGTGAAGCCTTC GGAGACCCTGTCCCTCACCTGCA CTGTCTCTGGTGGCTCCATCAGT AGTTACTACTGGAGCTGGATCCG GCAGCCCCAGGGAAGGGACTG GAGTGGATTGGGTATATCTATTA CAGTGGGACCACCAACTACAAC CCCTCCCTCAAGAGTCGAGTCAC CATATCAGTAGACACGTCCAAG AACCAGTTCTCCCTGAAGCTGAG CTCTGTGACCGCTGCGGACACG GCCGTGTATTACTGTGCGAGAGT AGTCCTGTATAGCACTGGCTGGT CCTTCGACTACTGGGGCCAGGG AACCCTGGTCACCGTCTCCTCAG SEQ ID NO: 187 | GAAATTGTAATGACACAGTCT CCAGCCACCCTGTCTTTGTCTC CAGGGGAAAGAGCCACCCTCT CCTGCAGGGCCAGTCAGAGTG TTAGCAGCAGCTACTTATCCT GGTACCAGCAGAGACCTGGG CAGGCTCCCAGGCTCCTCATC TATGGTACGTCCACCAGGGCC ACTGGCATCCCAGCCAGGTTC AGTGGCAGTGGGTCTGGGACA GACTTCACTCTCACCATCAGC AGCCTGCAGCCTGAAGATTTT GCAGTTTATTACTGTCAGCAG GATTATAACTTACCGCTCACT TTCGGCGGAGGGACCAAGGT GGAGATCAAA SEQ ID NO: 188 |
| 10-P12A | CAGGTGCAGCTGCAGGAGTCGG GCCCAGGACTGGTGAAGCCTTC GGAGACCCTGTCCCTCACCTGCA CTGTCTCTGGTGGCTCCATCAGT AGTTACTACTGGAGCTGGATCCG GCAGCCCCAGGGAAGGGACTG GAGTGGATTGGGTATATCTATTA CAGTGGGAGCACCAACTACAAC CCCTCCCTCAAGAGTCGAGTCAC CATATCAGTAGACACGTCCAAG AACCAGTTCTCCCTGAAGCTGAG CTCTGTGACCGCTGCGGACACG GCCGTGTATTACTGTGCGAGAGT | GAAATTGTAATGACACAGTCT CCAGCCACCCTGTCTTTGTCTC CAGGGGAAAGAGCCACCCTCT CCTGCAGGGCCAGTCAGAGTT TTAGCAGCAGCTACTTATCCT GGTACCAGCAGAAACCTGGG CAGGCTCCCAGGCTCCTCATC TATGGTGCATCCACCAGGGCC ACTGGCATCCCAGCCAGGTTC AGTGGCAGTGGGTCTGGGACA GACTTCACTCTCACCATCAGC AGCCTGCAGCCTGAAGATTTT GCAGTTTATTACTGTCAGCAG |

TABLE 3-continued

| Clone | Heavy chain variable region nucleic acid sequence | Light chain variable region nucleic acid sequence |
| --- | --- | --- |
| | AGTCCTGTATAGCAGTGGCTGGT<br>CCTTCGACTACTGGGGCCAGGG<br>AACCCTGGTCACCGTCTCCTCAG<br>SEQ ID NO: 189 | GATTATAACTTACCGCTCACT<br>TTCGGCGGAGGGACCAAGGT<br>GGAGATCAAA<br>SEQ ID NO: 190 |
| 2-M12A | CAGGTGCAGCTGCAGGAGTCGG<br>GCCCAGGACTGGTGAAGCCTTC<br>GGAGACCCTGTCCCTCACCTGCA<br>CTGTCTCTGGTGGCTCCATCAGT<br>CATTACTACTGGAGCTGGATCCG<br>GCAGCCCCCAGGGAAGGGACTG<br>GAGTGGATTGGGTATATCTATTA<br>CAGTGGGAGCACCAACTACAAC<br>CCCTCCCTCAAGAGTCGAGTCAC<br>CATATCAGTAGACACGTCCAAG<br>AACCAGTTCTCCCTGAAGCTGAG<br>CTCTGTGACCGCTGCGGACACG<br>GCCGTGTATTACTGTGCGAGAGT<br>AGTCCTGTATAGCAGTGGCTGGT<br>CCTTCGACTACTGGGGCCAGGG<br>AACCCTGGTCACCGTCTCCTCAG<br>SEQ ID NO: 191 | GAAATTGTAATGACACAGTCT<br>CCAGCCACCCTGTCTTTGTCTC<br>CAGGGGAAAGAGCCACCCTCT<br>CCTGCAGGGCCAGTCAGAGTG<br>TTAGCAGCAGCTACTTATCCT<br>GGTACCAGCAGAAACCTGGG<br>CAGGCTCCCAGGCTCCTCATC<br>TATGGTGCATCCACCAGGGCC<br>ACTGGCATCCCAGCCAGGTTC<br>AGTGGCAGTGGGTCTGGGACA<br>GACTTCACTCTCACCATCAGC<br>AGCCTGCAGCCTGAAGATTTT<br>GCAGTTTATTACTGTCAGCAG<br>GATTATAACTTACCGCTCACT<br>TTCGGCGGAGGGACCAAGGT<br>GGAGATCAAA<br>SEQ ID NO: 192 |
| 1-G20A | CAGGTGCAGCTGCAGGAGTCGG<br>GCCCAGGACTGGTGAAGCCTTC<br>GGAGACCCTGTCCCTCACCTGCA<br>CTGTCTCTGGTGGCTCCATCAGT<br>AGTTACTACTGGAGCTGGATCCG<br>GCAGCCCCCAGGGAAGGGACTG<br>GAGTGGATTGGGTATATCTATTA<br>CAGTGGGAGCACCAACTACAAC<br>CCCTCCCTCAAGAGTCGAGTCAC<br>CATATCAGTTGACACGTCCAAG<br>AACCAGTTCTCCCTGAAGCTGAG<br>CTCTGTGACCGCTGCGGACACG<br>GCCGTGTATTACTGTGCGAGAGT<br>AATGGTGTTTAGCAGTGGCTGGT<br>ACTTTGACTACTGGGGCCAGGG<br>AACCCTGGTCACCGTCTCCTCAG<br>SEQ ID NO: 193 | GAAATTGTAATGACACAGTCT<br>CCAGCCACCCTGTCTTTGTCTC<br>CAGGGGAAAGAGCCACCCTCT<br>CCTGCAGGGCCAGTCAAAATA<br>TTACCAGCAGCTACTTATCCT<br>GGTACCAGCAGAAACCTGGG<br>CAGTCTCCCAGGCTCCTCATT<br>TATGATGCATCCACCAGGGCC<br>ACTGGCATCCCAGCCAGGTTC<br>AGTGGCAGTGGGTCTGGGACA<br>GACTTCACTCTCACCATCAGC<br>AGCCTGCAGCCTGAAGATTTT<br>GCAGTTTATTACTGTCAGCAG<br>GATTATAACTTACCGCTCACT<br>TTCGGCGGAGGGACCAAGGT<br>GGAGATCAAA<br>SEQ ID NO: 194 |
| 12-F16A | CAGGTGCAGCTGCAGGAGTCGG<br>GCCCAGGACTGGTGAAGCCTTC<br>GGAGACCCTGTCCCTCACCTGCA<br>CTGTCTCTGGTGGCTCCATCAGT<br>AGTCACTACTGGAGCTGGATCC<br>GGCAGCCCCCAGGGAAGGGACT<br>GGAGTGGATTGGGTATATCTATT<br>ACAGTGGGAATACCAAGTACAA<br>CCCCTCCCTCAAGAGTCGAGTCA<br>CCATTTCAGTCGACACGTCCAAG<br>AACCAGTTCTCCCTGAAGCTGAC<br>CTCTGTGACCGCTGCGGACACG<br>GCCGTGTATTACTGTGCGAGAGT<br>GGGCCCGGGGAGTCATTATAAC<br>CCTCACAACTGGTTCGACCCCTG<br>GGGCCAGGGAACCCTGGTCACC<br>GTCTCCTCAG<br>SEQ ID NO: 195 | GAAATTGTAATGACACAGTCT<br>CCAGCCACCCTGTCTTTGTCTC<br>CAGGGGAAAGAGCCACCCTCT<br>CCTGCAGGGCCAGTCAGACTG<br>TTACCAGCAGCTACTTATCCT<br>GGTACCAGCAGAAACCTGGG<br>CAGGCTCCCAGGCTCCTCATC<br>TATGGTGCATCCACCAGGGCC<br>ACTGGCTTCCCAGCCAGGTTC<br>AGTGTCAGTGGGTCTGGGACA<br>GACTTCACTCTCACCATCAGC<br>AGCCTGCAGCCTGAAGATTTT<br>GCAGTTTATTACTGTCAGCAG<br>GATTATAACTTACCGTGGACG<br>TTCGGCCAAGGGACCAAGGTG<br>GAAATCAAA<br>SEQ ID NO: 196 |
| 11-N12A | CAGGTTCAGCTGGTGCAGTCTGG<br>AGCTGAGGTGAAGAAGCCTGGG<br>GCCTCAGTGAAGGTCTCCTGCAA<br>GGCTTCTGGTTACACCTTTACCA<br>ACTATGGTATCATCTGGGTGCGA<br>CAGGCCCCTGGACAAGGGCTTG<br>AGTGGATGGGATGGATCAGCGC<br>TTACAATGGTAACACAAACTAT<br>GCACAGAAGCTCCAGGGCAGAG<br>TCACCATGACCACAGACACATC<br>CACGAGCACAGCCTACATGGAG<br>CTGAGGACCCTGAGATCTGACG<br>ACACGGCCGTGTATTACTGTGCG<br>AGAGATTACTATAGTTCGGGGA | CAGCTTGTGCTGACTCAATCG<br>CCCTCTGCCTCTGCCTCCCTGG<br>GAGCCTCGGTCAAGCTCACCT<br>GCACTCTGAGCAGTGGGCACA<br>GCAGCTACGCCATCGCATGGC<br>ATCAGCAGCAGCCAGAGAAG<br>GGCCCTCGGTACTTGATGAAG<br>CTTAACAGTGATGGCAGCCAC<br>AGCAAGGGGGACGGGATCCC<br>TGATCGCTTCTCAGGCTCCAG<br>CTCTGGGGCTGAGCGCTACCT<br>CACCATCTCCAGCCTCCAGTC<br>TGTGGATGAGGCTGACTATTA<br>CTGTCAGACCTGGGGCACTGG |

TABLE 3-continued

| Clone | Heavy chain variable region nucleic acid sequence | Light chain variable region nucleic acid sequence |
|---|---|---|
| | GTTATGGGGCTGGTTCGACCCC<br>TGGGGCCAGGGAACCCTGGTCA<br>CCGTCTCCTCAG<br>SEQ ID NO: 197 | CATTCGGGTGTTCGGTGGAGG<br>AACCAAACTGACTGTCCTA<br>SEQ ID NO: 198 |
| 18-K8A | CAGGTTCAGCTGGTGCAGTCTGG<br>AGCTGAGGTGAAGAAGCCTGGG<br>GCCTCAGTGAAGGTCTCCTGCAA<br>GGCTTCTGGTTACACCTTTACCA<br>ACTATGGTATCATCTGGGTGCGA<br>CAGGCCCCTGGACAAGGGCTTG<br>AGTGGATGGGATGGATCAGCGC<br>TTACAATGGTAACACAAACTAT<br>GCACAGAAGCTCCAGGGCAGAG<br>TCACCATGACCACAGACACATC<br>CACGAGCACAGCCTACATGGAG<br>CTGAGGAGCCTGAGATCTGACG<br>ACACGGCCGTGTATTACTGTGCG<br>AGAGATTACTATAGTTCGGGGA<br>GTTATGGGGCTGGTTCGACCCC<br>TGGGGCCAGGGAACCCTGGTCA<br>CCGTCTCCTC<br>SEQ ID NO: 199 | CAGCTTGTGCTGACTCAATCG<br>CCCTCTGCCTCTGCCTCCCTGG<br>GAGCCTCGGTCAAGCTCACCT<br>GCACTCTGAGCAGTGGGCACA<br>GCAGCTACGCCATCGCATGGC<br>ATCAGCAGCAGCCAGAGAAG<br>GGCCCTCGGTACTTGATGAAG<br>CTTAACAGTGATGGCAGCCAC<br>AGCAAGGGGGACGGGATCCC<br>TGATCGCTTCTCAGGCTCCAG<br>CTCTGGGGCTGAGCGCTACCT<br>CACCATCTCCAGCCTCCAGTC<br>TGTGGATGAGGCTGACTATTA<br>CTGTCAGACCTGGGGCACTGG<br>CATTCGGGTGTTCGGTGGAGG<br>AACCAAACTGACTGTCCTA<br>SEQ ID NO: 200 |
| 17-L17A | GAGGTGCAGCTGTTGGAGTCTG<br>GGGGAGGCTTGGTACAGCCGGG<br>GGGGTCCCTGAGACTCTCCTGTG<br>CAGCCTCTGGATTCACGTCTAGT<br>AGCTATGCCATGAGCTGGGTCC<br>GCCAGGCTCCAGGGAAGGGGCT<br>GGAGTGGGTCTCAGGTATTAGT<br>GGTAGTGGTGATAGTACATATTA<br>CGCAGACTCCGTGAAGGGCCGG<br>TTCATTATTTCCAGAGACAATTC<br>CAAGAACACGCTGTATCTGCAA<br>ATGAACAGCCTGAGAGCCGAGG<br>ACACGGCCGTATATTACTGTGCG<br>AAAGGGGATTACTATGGTTCGG<br>GGAGTTATCCCTTTTTGACTAC<br>TGGGGACAGGGAACCCGGGTCA<br>CCGTCTCCTCAG<br>SEQ ID NO: 201 | GCCATCCAGTTGACCCAGTCT<br>CCATCCTCCCTGTCTGCATCTG<br>TAGGAGACAGAGTCACCATCA<br>CTTGCCGGGCAAGTCAGGGCA<br>TTAGCAGTGCTTTAGCCTGGT<br>ATCAGCAAAAACCAGGGAAA<br>GCTCCTAAGCTCCTGATCTCT<br>GATGCCTCCAGTTTGGAAAGT<br>GGGGTCCCATCAAGGTTCAGC<br>GGCGGTGGATCTGGGACAGAT<br>TTCACTCTCACCATCAGCAGC<br>CTGCAGCCTGAAGATTTTGCT<br>ACTTATTACTGTCAACAGTTTT<br>ATAATTACCCTCCCACTTTCG<br>GCCCTGGGACCAAAGTGGATA<br>TCATA<br>SEQ ID NO: 202 |
| 16-I20A | CAGGTGCAGCTGCAGGAGTCGG<br>GCCCAGGACTGGTGAAGCCTTC<br>GGAGACCCTGTCCCTCACCTGCA<br>CTGTCTCTGGTGGCTCCATCAGT<br>TATTACTACTGGAGCTGGATCCG<br>GCAGCCCCCAGGGACGGGACTG<br>GAGTGGATTGGGTATATCTATTA<br>TAGTGGGAGCACCAAATACAAC<br>CCCTCCCTCAAGAGGCGAGTCA<br>CCATATCAGTAGACACGTCCAA<br>GAACCAGTTCTCCCTGAAGCTGA<br>GCTCTGTGACCGCTGCGGACAC<br>GGCCGTGTATTACTGTGCGAGA<br>ATACGTGGGACAGCTATGGTT<br>GGGATTTTGACTACTGGGGCCA<br>GGGAACCCTGGTCACCGTCTCCT<br>CAG<br>SEQ ID NO: 203 | GAAATTGTAATGACACAGTCT<br>CCAGCCACCCTGTCTTTGTCTC<br>CAGGGGAAAGAGCCACCCTCT<br>CCTGCAGGGCCAGTCAGAGTA<br>TTAGCAACAACTATTTATTCT<br>GGTACCAGCAGAAACCTGGG<br>CAGGCTCCCAGGCTCCTCATC<br>TATGGTGCTTCCACCAGGGCC<br>ACTGGCATCCCAGCCAGGTTC<br>AGTGGCAGTGGGTCTGGGACA<br>GACTTCACTCTCACCATCAGC<br>AGCCTGCAGCCTGAAGATTTT<br>GCAGTTTATTACTGTCAGCAG<br>GATTATAACTTTCCTCTCACTT<br>TCGGCGGAGGGACCAAGGTG<br>GAGATCAAA<br>SEQ ID NO: 204 |
| 15-C19A | CAGGTGCAGCTGCAGGAGTCGG<br>GCCCAGGACTGGTGAAGCCTTC<br>GGAGACCCTGTCCCTCACCTGCA<br>CTGTCTCTGGTGGCTCCATCAGT<br>AGTTACTACTGGAGTTGGATCCG<br>GCAGCCCCCAGGGAAGGGACTG<br>GAGTGGATTGGATATATCTCTTA<br>TAGTGGGAGCACCAACTACAAC<br>CCCTCCCTCAAGAGTCGAGTCAC<br>CATATCAGCAGACACGTCCAAG<br>AACCAATTCTCCCTGAAGCTGAG<br>CTCTGTGACCGCTGCGGACACG<br>GCCGTGTATTACTGTGCGAGAG<br>ACTTTTACTACGGTATGGACGTC | GCCATCCAGTTGACCCAGTCT<br>CCATCCTCCCTGTCTGCATCTG<br>TAGGAGACAGAGTCACCATCA<br>CTTGCCGGGCAAGTCAGGGCA<br>TTAGCAGTGCTTTAGCCTGGT<br>ATCAGCAGAAACCAGGGAAA<br>GCTCCTAAACTCCTGATCTAT<br>GATGCCTCCAGTTTGGAAAGT<br>GGGGTCCCATCAAGGTTCAGC<br>GGCAGTGGATCTGGGACAGAT<br>TTCACTCTCACCATCAGCAGC<br>CTGCAGCCTGAAGATTTTGCA<br>ACTTATTACTGTCACCAGTTT<br>GATTATTACCCTACTTTCGGC |

TABLE 3-continued

| Clone | Heavy chain variable region nucleic acid sequence | Light chain variable region nucleic acid sequence |
|---|---|---|
| | TGGGGCCAAGGGACCACGGTCA<br>CCGTCTCCTCA<br>SEQ ID NO: 205 | GGAGGGACCAAGGTGGAGAT<br>CAAA<br>SEQ ID NO: 206 |
| 15-E14A | GAGGTGCAGCTGTTGGAGTCTG<br>GGGGAGGCTCGGAACAGCCGGG<br>GGGGTCCCTGAGACTCTCCTGTG<br>CAGCCTCTGGATTCACCTCTAGC<br>AGCTATGCCATGAGCTGGGTCC<br>GCCTGGCTCCAGGGAAGGGGCT<br>GGAGTGGGTCTCAGGTATTAGT<br>GGGAGTGGTGGTGGCACATACT<br>ACGCAGACTCCGTGAAGGGCCG<br>GTTCACCACTTCCAGAGACAATT<br>CCAAGAACACGCTGTATCTGCA<br>AATGAACAGCCTGAGAGCCGAG<br>GACACGGCCGTATATTACTGTAC<br>GAAAGGGGATTACTATGGTTCG<br>GGGAGTTATCCCCTTTTTGACTA<br>CTGGGGCCAGGGAACCCTGGTC<br>ACCGTCTCCTCAG<br>SEQ ID NO: 207 | GCCATCCAGTTGACCCAGTCT<br>CCATCCTCCCTGTCTGCATCTG<br>TAGGAGACAGAGTCACCATCA<br>CTTGCCGGGCAAGTCAGGGCA<br>TTAGCAGTGCTTTAGCCTGGT<br>ATCAGCAGAAACCAGGGAAA<br>GCTCCTAAACTCCTGATCTCT<br>GATGCCTCCAGTTTGGAAAGT<br>GGGGTCCCATCTAGGTTCAGC<br>GGCAGTGGCTCTGGGACAGAT<br>TTCACTCTCACCATCAGCAGC<br>CTGCAACCTGAAGATTTTGCA<br>ACTTATTACTGTCAACAATTT<br>AATAACTACCCTCCCACTTTC<br>GGCCCTGGGACCAAAGTGGAT<br>ATCAAA<br>SEQ ID NO: 208 |
| 16-H16A | CAGTTGCAGCTGCAGGAGTCGG<br>GCCCAGGACTGGTGAAGCCTTC<br>GGAGACCCTGTCCCTCACCTGCA<br>CTGTCTCTGGTGACTCCATCAGC<br>AGTAGTGGTTACTACTGGGGCTG<br>GATCCGCCAGCCCCCAGGGAAG<br>GGGCTGGAATGGATTGGGAGTA<br>TCTATTATAGTGGGAGCACCCAC<br>TACAACCCGTCCCTCAAGAGTCG<br>AGTCACCATATCCGTAGACTCGT<br>CCAAGAGCCAGTTCTCCCTGAA<br>GCTAAGCTCTGTGACCGCCGCA<br>GACACGGCTGTGTATTGCTGTGC<br>GAGACATAAGGTAGATAGCAGT<br>GGCTGGCCCCTTGACTACTGGGG<br>CCAGGGAACCCTGGTCACCGTCT<br>CCTCAG<br>SEQ ID NO: 209 | GAAATTGTAATGACACAGTCT<br>CCAGCCACCCTGTCTTTGTCTC<br>CAGGGGAAAGAGCCACCCTCT<br>CCTGCAGGGCCAGTCAGAGTA<br>TTAGCAGCAGCTGCTTGTCCT<br>GGTACCAGCAGAAACCTGGG<br>CAGGCTCCCAGGCTCCTCATC<br>TATGATACATCCACCAGGGCC<br>ACTGGCATCCCAGCCAGGTTC<br>AGTGGCAGTGGGTCTGGGACA<br>GACTTCACTCTCACCATCAGC<br>AGCCTGCAGCCTGAAGATTTT<br>GCAGTTTATTACTGTCAGCAG<br>GATTATAACTTACCGCTCACT<br>TTCGGCGGAGGGACCAAGGT<br>GGAGATCAAA<br>SEQ ID NO: 210 |
| 12-O8A | CAGGTGCAGCTGGTGGAGTCTG<br>GGGGAGGCGTGGTCCAGCCTGG<br>GAGGTCCCTGAGACTCTCCTGTG<br>CAGCGTCTGGATTCACCTTCAGT<br>AGCTATGGCATGCACTGGGTCC<br>GCCAGGCTCCAGGCAAGGGGCT<br>GGAGTGGGTGGCAGTTATATGG<br>TATAATGGAAGTAATAGATACT<br>ATGCAGACTCCGTGAAGGGCCG<br>ATTCACCATCTCCAGAGACAATT<br>CCAAGAACACGCTGTATCTGCA<br>AATGAACAGCCTGAGAGCCGAG<br>GACACGGCTGTGTATTACTGTGC<br>GAGAGATGACGTAGTACGATAT<br>TTTGACTGGCCCCTTGACTACTG<br>GGGCCAGGGAACCCTGGTCACC<br>GTCTCCTCAG<br>SEQ ID NO: 211 | GCCATCCAGATGACCCAGTCT<br>CCATCCTCCCTGTCTGCATCTG<br>TAGGAGACAGAGTCACCATCA<br>CTTGCCGGGCAAGTCAGGGCA<br>TTAGAAATGATTTAGGCTGGT<br>ATCAGCAGAAACCAGGGAAA<br>GCCCCTAAGGTCCTGATCTAT<br>GCTGCATCCAGTTTACAAAGT<br>GGGGTCCCATCAAGGTTCAGC<br>GGCAGTGGATCTGGCACAGAT<br>TTCACTCTCACCATCAGCAGC<br>CTGCAGCCTGAAGATTTTGCA<br>ACTTATTACTGTCTACAAGAT<br>TACAATTACCCGTGGACGTTC<br>GGCCAAGGGACCAAGGTGGA<br>AATCAAA<br>SEQ ID NO: 212 |
| 12-I8A | CAGGTGCAGCTGGTGGAGTCTG<br>GGGGAGGCGTGGTCCAGCCTGG<br>GAGGTCCCTGAGACTCTCCTGTG<br>CAGCGTCTGGATTCACCTTCAGT<br>AACTATGGCATGCACTGGGTCC<br>GCCAGGCTCCAGGCAAGGGGCT<br>GGAGTGGGTGGCAGTTATATGG<br>TATAATGGAAGTAATAAATACT<br>ATGCAGACTCCGTGAAGGGCCG<br>ATTCACCATCTCCAGAGACAATT<br>CCAAGAACACGCTGTATCTGCA<br>AATGAACAGCCTGAGAGCCGAG<br>GACACGGCTGTGTATTACTGTGC<br>GAGAGATGACGTCGTACGATAT<br>TTTGACTGGCCCCTTGACTACTG | GCCATCCAGATGACCCAGTCT<br>CCATCCTCCCTGTCTGCATCTG<br>TAGGAGACAGAGTCACCATCA<br>CTTGCCGGGCAAGTCAGGGCA<br>TTAGAAATGATTTAGGCTGGT<br>ATCAGCAGAAACCAGGGAAA<br>GCCCCTAAGGTCCTGATTTAT<br>GCTGCATCCAGTTTACAAAGT<br>GGGGTCCCATCAAGGTTCAGC<br>GGCAGTGGATCTGGCACAGAT<br>TTCACTCTCACCATCAGCAGC<br>CTGCAGCCTGAAGATTTTGCA<br>ACTTATTACTGTCTACAAGAT<br>TACAATTACCCGTGGACGTTC<br>GGCCAAGGGACCAAGGTGGA |

TABLE 3-continued

| Clone | Heavy chain variable region nucleic acid sequence | Light chain variable region nucleic acid sequence |
| --- | --- | --- |
| | GGGCCAGGGAACCCTGGTCACC GTCTCCTCAG SEQ ID NO: 213 | AATCAAA SEQ ID NO: 214 |
| 8-M23A | CAGGTGCAGCTGCAGGAGTCGG GCCCAGGACTGGTGAAGCCTTC GGGAGACCCTGTCCCTCACCTGCA CTGTCTCTGGTGGCTCCATCAGT AGTTACTACTGGAGCTGGATCCG GCAGCCCCCAGGGAAGGGACTG GAGTGGATTGGGTATATCTATTA CAGTGGGAGCACCAACTACAAC CCCTCCCTCAAGAGTCGAATCAC CATATCAGTAGACACGTCCAAG AACCAGTTCTCCCTGAAGCTGAG CTCTGTGACCGCTGCGGACACG GCCGTGTATTACTGTGCGAGAGT AATCCTGTATAGCAGTGGCTGGT CCTTCGACTACTGGGGCCAGGG AACCCTGGTCACCGTCTCCTCAG SEQ ID NO: 215 | GAAATTGTAATGACACAGTCT CCAGCCACCCTGTCTTTGTCTC CAGGGGAAAGAGCCACCCTCT CCTGCAGGGCCAGTCAGAGTG TTAGCAGCAGCTACTTATCCT GGTACCAGCAGAAACCTGGG CAGGCTCCCAGGCTCCTCATC TATGGTGCATCCACCAGGGCC ACTGGCATCCCAGCCAGGTTC AGTGGCAGTGGGTCTGGGACA GACTTCACTCTCACCATCAGC AGCCTGCAGCCTGAAGATTTT GCAGTTTATTACTGTCAGCAG GATTATAACTTACCGCTCACT TTCGGCGGAGGGACCAAGGT GGAGATCAAA SEQ ID NO: 216 |
| 1-F23A | CAGGTGCAGCTGCAGGAGTCGG GCCCAGGACTGGTGAAGCCTTC GGGAGACCCTGTCCCTCACCTGCA CTGTCTCTGGTGGCTCCATCAGT AGTTACTACTGGAGCTGGATCCG GCAGCCCCCAGGGAAGGGACTG GAGTGGATTGGGTATATCTATTA CAGTGGGAGCACCAACTACAAC CCCTCCCTCAAGAGTCGAATCAC CATATCAGTAGACACGTCCAAG AACCAGTTCTCCCTGAAACTGAG CTCTGTGACCGCTGCGGACACG GCCGTGTATTACTGTGCGAGAGT AATCCTGTATAGCAGTGGCTGGT CCTTCGACTACTGGGGCCAGGG AACCCTGGTCACCGTCTCCTCAG SEQ ID NO: 217 | GAAATTGTAATGACACAGTCT CCAGCCACCCTGTCTTTGTCTC CAGGGGAAAGAGCCACCCTCT CCTGCAGGGCCAGTCAGAGTG TTAGCAGCAGCTACTTATCCT GGTACCAACAGAAGCCTGGG CAGGCTCCCAGGCTCCTCATC TATGATGCATCCACCAGGGCC ACTGGCATCCCAGCCAGGTTC AGTGGCAGTGGGTCTGGGACA GACTTCACTCTCACCATCAGC AGCCTGCAGCCTGAAGATTTT GCAGTTTATTACTGTCAGCAG GATTATAACTTACCGCTCACT TTCGGCGGAGGGACCAAGGT GGAGATCAAA SEQ ID NO: 218 |
| 13-F7A | GAGGTGCAGTTGTTGGAGTCTG GGGGAGGCTTGGTACAGCCTGG GGGGTCCCTGAGACTCTCCTGTG CAGCCTCTGGATTCACCTCTAGC AGCTATGGCATGAGCTGGGTCC GCCAGGCTCCAGGGAAGGGGCT GGAGTGGGTCTCAGGTATTAGT GGTAGTGGTGGTGGCACATACT ACGCAGACTCCGTGAAGGGCCG GTTCACCATCTCCAGAGACAATT CCAAGAACACGCTGTATCTGCA AATGAACAGCCTGAGAGCCGAG GACACGGCCGTATATTACTGTGC GAAAGGGGATTACTATGGTTCG GGGAGTTATCCCCTTTTTGACTA CTGGGGCCAGGGAACCCTGGTC ACCGTCTCCTCAG SEQ ID NO: 219 | GCCATCCAGTTGACCCAGTCT CCATCCTCCCTGTCTGCATCTG TAGGAGACAGAGTCACCATCA CTTGCCGGGCAAGTCAGGACA TTAGCAGTGCTTTAGCCTGGT ATCAGCAGAAACCAGGGAAA GCTCCTAAGCTCCTGATCTCT GATGCCTCCAGTTTGGAAAGT GGGGTCCCATCAAGGTTCAGC GGCAGTGGATCTGGGACAGAT TTCACTCTCACCATCAGCAGC CTGCAACCTGAAGATTTTGCA ACTTTTTACTGTCAACAGTTTA ATAATTACCCTCCCACTTTCG GCCCTGGGACCAAAGTGGATA TCAAA SEQ ID NO: 220 |
| 11-F3A | GAGGTGCAGCTGTTGGAGTCTG GGGGAGGCTTGGTACAGCCTGG GGGGTCCCTGAGACTCTCCTGTG CAGCCTCTGGATTCACCTTTAGC AGCTATGCCATGAGCTGGGTCC GCCAGGCTCCAGGGAAGGGGCT GAAATGGGTCTCAGGTATTAGT GGTAGTGGTGGTGGCACATACT ACGCAGACTCCGTGAAGGGCCG GTTCACCCTCTCCAGAGACAATT CCAAGAACACATATATCTGCA AATGAACAGCCTGAGAGCCGAG GACACGGCCGTATATTTCTGTGC | GCCATCCAGTTGACCCAGTCT CCATCCTCCCTGTCTGCATCTG TAGGAGACAGAGTCACCATCA CTTGCCGGGCAAGTCAGGGCA TTAGCAGTGCTTTAGCCTGGT ATCAACAGAAACCAGGGAAA GCTCCTAAGCTCCTGATCTTT GATGCCTCCAGTTTGGAAAGT GGGGTCCCATCAAGGTTCAGC GGCAGTGGATCTGGGACAGAT TTCACTCTCACCATCAGCAGC CTGCAGCCTGAAGATTTTGCA ACTTATTACTGTCAACAGTTT |

TABLE 3-continued

| Clone | Heavy chain variable region nucleic acid sequence | Light chain variable region nucleic acid sequence |
|---|---|---|
| | GAAAGGGGATTACTATGGTTCG<br>GGGAGTTATCCCCTTTTTGACTT<br>CTGGGGCCAGGGAACCCTGGTC<br>ACCGTCTCCTCA<br>SEQ ID NO: 221 | AATGATTACCCTCCCACTTTC<br>GGCCCTGGGACCAAACTGGAT<br>ATCAAA<br>SEQ ID NO: 222 |
| 20-E16A | CAGGTGCAGCTGCAGGAGTCGG<br>GCCCAGGACTGGTGAAGCCTTC<br>GGAGACCCTGTCCCTCACCTGCA<br>CTGTCTCTGGTGGCTCCATCAGT<br>AGTTACTACTGGACCTGGATCCG<br>GCAGCCCCCAGGGAAGGGACTG<br>GAGTGGATTGGACATATCTCTTA<br>CAGTGGGAGCACCCACTACAAC<br>CCCTCCCTCAAGAGTCGATTCAC<br>CATATCAGCAGACACGTCCAAG<br>AACCGGTTCTCCCTGAAGCTGAG<br>CTCTGTGACCGCTGCGGACACG<br>GCCGTGTATTACTGTGCGCGAGA<br>TGGCTACTACGCTTTGGACGTCT<br>GGGGCCAAGGGACCACGGTCAC<br>CGTCTCCTCA<br>SEQ ID NO: 223 | GCCATCCAGTTGACCCAGTCT<br>CCATCCTCCCTGTCTGCATCTG<br>TAGGAGACAGAGTCACCATCA<br>CTTGCCGGGCAAGTCAGGACA<br>TTAGCAATACTGTAGCCTGGT<br>ATCAGCAGAACCCAGGGAAA<br>GCTCCTAAGCTCCTGATCTAT<br>GATGCCTCCAGTTTGGAAAGT<br>GGGGTCTCATCAAGGTTCAGC<br>GGCAGTGGATCGGGGACAGA<br>TTTCACTCTCACCATCAGCAG<br>CCTGCAGCCTGAAGATTTTGC<br>AACTTATTACTGTCAACAGTT<br>TAATAATTACCCGTACACTTT<br>TGGCCAGGGGACCAAGCTGG<br>AGATCAAA<br>SEQ ID NO: 224 |
| 16-K19A | GAGGTGCAGCTGTTGGAGTCTG<br>GGGGAGGCTTGGAACAGCCGGG<br>GGGGTCCCTGAGACTCTCCTGTG<br>CAGCCTCTGGATTCACCTCTAGC<br>AGCTATGCCATGAGCTGGGTCC<br>GCCAGGCTCCAGGGAAGGGGCT<br>GGAGTGGGTCTCAGGTATTAGT<br>GGGAGTGGTGGTGGCACATACT<br>ACGCAGACTCCGTGAAGGGCCG<br>GTTCTCCACTTCCAGAGACAATT<br>CCAAGAACACGCTTTATCTGCAA<br>ATGAACAGCCTGAGAGCCGAGG<br>ACACGGCCGTATATTACTGTGCG<br>AAAGGGGATTACTATGGTTCGG<br>GGAGTTATCCCCTTTTTGACTAC<br>TGGGGCCAGGGAACCCTGGTCA<br>CCGTCTCCTCA<br>SEQ ID NO: 225 | GCCATCCAGTTGACCCAGTCT<br>CCATCCTCCCTGTCTGCATCTG<br>TAGGAGACAGAGTCACCATCA<br>CTTGCCGGGCAAGTCAGGGCA<br>TTAGCAGTGCTTTAGCCTGGT<br>ATCAGCAGAAACCAGGGAAA<br>CCTCCTAAGCTCCTGATCTCT<br>GATGCCTCCAGTTTGGAAAGT<br>GGGGTCCCATCTAGGTTCAGC<br>GGCAGTGGCTCTGGGACAGAT<br>TTCACTCTCACCATCAGCAGC<br>CTGCAGCCTGAAGATTTTGCA<br>ACTTATTACTGTCAACAGTTT<br>AATAACTACCCTCCCACTTTC<br>GGCCCTGGGACCAAAGTGGAT<br>ATCAAA<br>SEQ ID NO: 226 |

Nucleic acid compositions encoding the anti-BTLA antibodies and/or BTLA-binding domains are also provided. As will be appreciated by those in the art, in the case of antigen binding domains, the nucleic acid compositions generally include a first nucleic acid encoding the heavy chain variable region and a second nucleic acid encoding the light chain variable region. In the case of scFvs, a single nucleic acid encoding the heavy chain variable region and light chain variable region, separated by a linker described herein, can be made. In the case of traditional antibodies, the nucleic acid compositions generally include a first nucleic acid encoding the heavy chain and a second nucleic acid encoding the light chain, which will, upon expression in a cell, spontaneously assemble into the "traditional" tetrameric format of two heavy chains and two light chains.

As is known in the art, the nucleic acids encoding the components of the invention can be incorporated into expression vectors, and depending on the host cells, used to produce the antibodies of the invention. These two nucleic acids can be incorporated into a single expression vector or into two different expression vectors. Generally, the nucleic acids can be operably linked to any number of regulatory elements (promoters, origin of replication, selectable markers, ribosomal binding sites, inducers, etc.) in an expression vector. The expression vectors can be extra-chromosomal or integrating vectors.

The nucleic acids and/or expression vectors of the current invention can be introduced into any type of host cells, which are well known in the art, including mammalian, bacterial, yeast, insect and fungal cells. After transfection, single cell clones can be isolated for cell bank generation using methods known in the art, such as limited dilution, ELISA, FACS, microscopy, or Clonepix. Clones can be cultured under conditions suitable for bio-reactor scale-up and maintained expression of the antibodies. The antibodies can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

IV. Therapeutic Applications

The current disclosure provides a method of modulating an immune response in a subject, and the method includes administering to the subject an effective amount of an anti-BTLA antibody described herein, or a pharmaceutical composition containing an anti-BTLA antibody.

In some embodiments, the methods of modulating an immune response encompassed by the present disclosure comprises stimulating an immune response in a subject, and in further embodiments, such methods comprise administering to the subject an effective amount of an anti-BTLA antibody that acts as a BTLA antagonist, or by administering a pharmaceutical composition containing an antagonistic anti-BTLA antibody.

In some embodiments, the methods encompassed by the present disclosure comprise methods of stimulating an immune response in a subject, for example, by administering an anti-BTLA antibody that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:21, and a light chain variable region comprising amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:22; and/or a vhCDR1 comprising SEQ ID NO:107, a vhCDR2 comprising SEQ ID NO:108, a vhCDR3 comprising SEQ ID NO:109, a vlCDR1 comprising SEQ ID NO:110, a vlCDR2 comprising SEQ ID NO:111, and a vlCDR3 comprising SEQ ID NO:112.

In some embodiments, the methods described herein stimulate an immune response in the subject, for example, by administering an anti-BTLA antibody that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:31 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:32; and/or vhCDR1 comprising SEQ ID NO:137, a vhCDR2 comprising SEQ ID NO:138, a vhCDR3 comprising SEQ ID NO:139, a vlCDR1 comprising SEQ ID NO:140, a vlCDR2 comprising SEQ ID NO:141, and a vlCDR3 comprising SEQ ID NO:142.

In some embodiments, the methods described herein stimulate an immune response in the subject, for example, by administering an anti-BTLA antibody that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:35, and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:36; and/or a vhCDR1 comprising SEQ ID NO:149, a vhCDR2 comprising SEQ ID NO:150, a vhCDR3 comprising SEQ ID NO:151, a vlCDR1 comprising SEQ ID NO:152, a vlCDR2 comprising SEQ ID NO:153, and a vlCDR3 comprising SEQ ID NO:154.

In some embodiments, the present disclosure provides methods for suppressing an immune response in a subject, for example, by administering to the subject an effective amount of an anti-BTLA antibody that acts as a BTLA agonist, or by administering to the subject a pharmaceutical composition containing such an agonistic anti-BTLA antibody.

In some other embodiments, the methods described herein suppress an immune response in the subject, for example, by administering an anti-BTLA antibody that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:19 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:20; and/or a vhCDR1 comprising SEQ ID NO:101, a vhCDR2 comprising SEQ ID NO:102, a vhCDR3 comprising SEQ ID NO:103, a vlCDR1 comprising SEQ ID NO:104, a vlCDR2 comprising SEQ ID NO:105, and a vlCDR3 comprising SEQ ID NO:106.

In some other embodiments, the methods described herein suppress an immune response in the subject, for example, by administering an anti-BTLA antibody that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:25 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:26; and/or a vhCDR1 comprising SEQ ID NO:119, a vhCDR2 comprising SEQ ID NO:120, a vhCDR3 comprising SEQ ID NO:121, a vlCDR1 comprising SEQ ID NO:122, a vlCDR2 comprising SEQ ID NO:123, and a vlCDR3 comprising SEQ ID NO:124.

In some other embodiments, the methods described herein suppress an immune response in the subject, for example, by administering an anti-BTLA antibody that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:29 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to comprising SEQ ID NO:30; and/or a vhCDR1 comprising SEQ ID NO:131, a vhCDR2 comprising SEQ ID NO:132, a vhCDR3 comprising SEQ ID NO:133, a vlCDR1 comprising SEQ ID NO:134, a vlCDR2 comprising SEQ ID NO:135, and a vlCDR3 comprising SEQ ID NO:136.

The present disclosure also provides methods of treating cancer in a subject, and such methods include administering to the subject an effective amount of an anti-BTLA antibody that acts as a BTLA antagonist, or a pharmaceutical composition containing such anti-BTLA antibody. In some embodiments, the cancer to be treated expresses HVEM and/or BTLA on the cancer cell surface. In some embodiments, the cancer to be treated upregulates HVEM and/or BTLA compared to the corresponding non-cancerous tissue. In some embodiments, the subject to be treated expresses HVEM and/or BTLA on T cells, such as on CD8+ and/or CD4+ T cells. In some embodiments, the subject to be treated expresses a high level of HVEM and/or BTLA on one or more types of immune cells including CD4+ T cells, CD8+ T cells, B cells, natural killer T cells, natural killer cells, macrophages, and dendritic cells. In some embodiments, the cancer to be treated uses the BTLA-HVEM pathway to downregulate the T cell response and/or escape from the immune recognition and destruction. In some embodiments, the cancer to treated is non-responsive to existing immune-modulating antibodies targeting other immune checkpoints, such as CTLA-4, PD-1 or PD-L1.

In some embodiments, the cancer is a solid tumor, such as gastric cancer, colorectal cancer, hepatocellular carcinoma, melanoma, or esophageal squamous cell carcinoma. In some embodiments, the cancer is B-cell chronic lymphocytic leukemia, Hodgkin's lymphoma, B-cell non-Hodgkin's lymphoma or T-cell non-Hodgkin's lymphomas.

In some other embodiments, the cancer is brain cancer, bladder cancer, breast cancer, cervical cancer, endometrial cancer, esophageal cancer, leukemia, lung cancer, liver cancer, melanoma, ovarian cancer, pancreatic cancer, prostate cancer, rectal cancer, renal cancer, testicular cancer, or uterine cancer. In yet other embodiments, the cancer is a vascularized tumor, squamous cell carcinoma, adenocarcinoma, small cell carcinoma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland cancer, carcinoid, cholangiocarcinoma, chondosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well-differentiated carcinoma, or Wilms tumor.

In some other embodiments, the cancer to be treated is a non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The present disclosure also provides methods of treating autoimmune or inflammatory disorders in a subject, and the method includes administering to the subject an effective amount of an anti-BTLA antibody that acts as a BTLA agonist, or a pharmaceutical composition containing such anti-BTLA antibody. In some embodiments, HVEM and/or BTLA is expressed at a low level in one or more types of immune cells in the subject to be treated, including T cells, B cells, natural killer cells, dendritic cells, endothelial cells, and macrophages. In some embodiments, HVEM and/or BTLA is expressed in the subject at a low level on autoreactive immune cells (e.g., T cells, B cells, natural killer cells, dendritic cells, endothelial cells, and macrophages) at sites where the autoimmune disease develops, for example, lymph nodes and central nervous system in the subject suffering from multiple sclerosis, joints in the subject suffering from Rheumatoid arthritis, and gastrointestinal tract in the subject suffering from Celiac disease). Administering an anti-BTLA antibody that acts as a BTLA agonist can suppress pro-inflammatory immune response, including pro-inflammatory T cell response, and modulate immune responses in the subject suffering from an autoimmune or inflammatory disorder.

In some embodiments, the autoimmune or inflammatory disorder to treated is multiple sclerosis, Addison's disease, amyotrophic lateral sclerosis, Crohn's disease, Cushing's Syndrome, diabetes mellitus type 1, graft versus host disease, Graves' disease, Guillain-Barré syndrome, lupus erythematosus, psoriasis, psoriatic arthritis, rheumatoid arthritis, sarcoidosis, scleroderma, systemic lupus erythematosus, transplant rejection, or vasculitis.

In some other embodiments, the autoimmune disorders to be treated include, but are not limited to, Acute disseminated encephalomyelitis (ADEM), Agammaglobulinemia, Alopecia areata, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Cutaneous leukocytoclastic angiitis, Dego's disease, Dercum's disease, Dermatitis herpetiformis, Dermatomyositis, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Meniere's disease, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatica, Polymyositis, Primary biliary cirrhosis, Primary sclerosing cholangitis, Progressive inflammatory neuropathy, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Schizophrenia, Schmidt syndrome, Schnitzler syndrome, Scleritis, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vitiligo, Wegener's granulomatosis.

V. Combination Therapy

Anti-BTLA antibodies described herein can be used in combination with additional therapeutic agents to treat cancer or autoimmune disorders.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3, such as Ipilimumab, Nivolumab, Pembrolizumab, Avelumab, Durvalumab, and Atezolizumab.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Antibodies of the invention can also be used as an adjunct to surgical removal of cancer from the primary lesion.

Exemplary therapeutic agents that may be used as a part of a combination therapy with an anti-BTLA antibody disclosed herein for treating, delaying the progression of, preventing a relapse of, or alleviating a symptom of an autoimmune or inflammatory disorder, include, for example, any anti-inflammatory and/or immunosuppressive therapy known in the art and described herein. In some embodiments, the anti-inflammatory and/or immunosuppressive therapies include, but are not limited to methotrexate, cyclosporin A (including, for example, cyclosporin microemulsion), tacrolimus, corticosteroids, statins, interferon beta, non-steroidal anti-inflammatory agents, and 6-MP (Mercaptopurine, also called 6-Mercaptopurine, or Purinethol).

In some embodiments, the anti-inflammatory and/or immunosuppressive therapies for combining with an anti-BTLA antibody disclosed herein include, but are not limited to a TOPK inhibitor (e.g., OTS964 ((R)-9-(4-(1-(dimethylamino)propan-2-yl)phenyl)-8-hydroxy-6-methylthieno[2,3-c] quinolin-4(5H)-one) (Oncotherapy Science)), a tyrosine kinase inhibitor (e.g., axitinib, dasatinib, icotinib), a topoisomerase inhibitor (e.g., topotecan), a sphingosine-1-phosphate receptor agonist (e.g., fingolimod, KRP-203), anti-T cell immunoglobulin (e.g., AtGam), anti-IL-2 receptor antibody (e.g., daclizumab), amides (CTX), ifosfamide (IFO), adriamycin (ADM), daunorubicin (DNR), vincristine (VCR), vinblastine (VBL), etoposide (VP16), vermeer (Vumon), carboplatin (CBP), tacrolimus, sirolimus, everolimus, azathioprine, brequinar, leflunomide, LEA-29Y, anti-CD3 antibody (e.g., OKT3), aspirin, B7-CD28 blocking molecules (e.g., belatacept, abatacept), CD40-CD154 blocking molecules (anti-CD40 antibodies), acetaminophen, ibuprofen, naproxen, piroxicam, and anti-inflammatory steroids (e.g., prednisolone or dexamethasone).

In some embodiments, the anti-inflammatory and/or immunosuppressive therapies for combining with an anti-BTLA antibody disclosed herein include ablation of autoimmune cells, for example, by administration of TNF-alpha, CFA, interleukin-1 (IL-1), proteasome inhibitors, NFκB inhibitors, anti-inflammatory drugs, tissue plasminogen activator (TPA), lipopolysaccharide, UV light, and an intracellular mediator of the TNF-alpha signaling pathway. Such agents induce the apoptosis of autoreactive lymphocytes by interrupting the pathway downstream from TNF-alpha receptor signaling or act downstream of TNF-alpha receptor binding. (Baldwin et al., Ann. Rev. Immunol. (1996) 12:141; Baltimore, Cell (1996) 87:13).

In some embodiments, an anti-BTLA antibody disclosed herein is used in conjunction with a surgical method of treating or otherwise alleviating autoimmune diseases.

For example, for treating, delaying the progression of, preventing a relapse of, or alleviating a symptom of multiple scelerosis, the anti-BTLA antibodies that act as BTLA agonists can be combined with any existing therapy for multiple scelerosis, for example, corticosteroids (e.g., oral prednisone and intravenous methylprednisolone), plasmapheresis, Ocrelizumab, beta interferons, Glatiramer acetate, Dimethyl fumarate, Fingolimod, Feriflunomide, Natalizumab, Alemtuzumab and/or Mitoxantrone.

The amount of the antibodies and additional therapeutic agents and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

VI. Pharmaceutical Composition and Administration

The present disclosure also features pharmaceutical compositions/formulations that contain a therapeutically effective amount of an anti-BTLA antibody described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The antibodies of the present disclosure can exist in a lyophilized formulation or liquid aqueous pharmaceutical formulation. The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The antibodies of the present disclosure could exist in a lyophilized formulation including the proteins and a lyoprotectant. The lyoprotectant may be sugar, e.g., disaccharides. In certain embodiments, the lyoprotectant is sucrose or maltose. The lyophilized formulation may also include one or more of a buffering agent, a surfactant, a bulking agent, and/or a preservative.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. It may be administered in the range of 0.1 mg to 1 g and preferably in the range of 0.5 mg to 500 mg of active antibody per administration for adults. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., Clinica Chimica Acta 308: 43-53, 2001; Steimer et al., Clinica Chimica Acta 308: 33-41, 2001).

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

EXAMPLES

The invention now being generally described, will be more readily understood by reference to the following examples, which are included merely for purposes of illustration of certain aspects and embodiments of the present invention, and is not intended to limit the invention.

Example 1—Anti-BTLA Antibodies Bind to Recombinant BTLA

Binding of anti-BTLA antibodies to human or cynomolgus BTLA was assayed by ELISA. Plates (384-well) were coated with 20 μl BTLA(ECD)-HIS (1 μg/ml) overnight at 4° C. The wells were then washed with PBS and then blocked with 55 µl blocking buffer for 1h at room temperature. The wells were then washed with PBS and anti-BTLA antibodies from the current invention as well as anti-BTLA antibodies 4C7 and 8D5 (described in U.S. Pat. No. 8,563,694), and human IgG control were added into the wells at various concentrations (67, 22, 7.4, 2.5, 0.8, 0.3, 0.09, 0.03, 0.01, 0.004, 0.001 nM) and incubated for 1h at room temperature. The wells were then washed with PBS, and 20 µl of the diluted HRP-conjugated secondary anti-human IgG antibody was then added to the wells and incubated at room temperature for 45 minutes. After removing excess HRP-conjugated secondary antibody, a substrate solution was added to the wells to develop a chemiluminescence signal. Photon emission was determined using an Omegastar plate reader and relative light units (RLU) were calculated. FIG. 1 shows an exemplary binding profile of anti-BTLA antibody 13-F7A to human BTLA in comparison with 4C7 and 8D5 antibodies. Human IgG was used as a negative control. Table 4 summarizes the binding EC50 of various anti-BTLA antibodies to human and cynomolgus BTLA measured by ELISA.

TABLE 4

| Clones | Human BTLA (RLU) EC50 (nM) | Cyno BTLA (RLU) EC50 (nM) |
| --- | --- | --- |
| 16-I20A | 0.7 | 0.8 |
| 15-C19A | 0.8 | 1.4 |
| 16-H16A | 0.9 | 1.9 |
| 12-I8A | 1.4 | 4.2 |
| 8-M23A | 0.8 | 4.2 |
| 13-F7A | 1.0 | 1.0 |
| 4C7 comparator | 0.9 | 12.6 |

Example 2—Anti-BTLA Antibodies Bind to BTLA Expressed on Cells

Figure 2A:
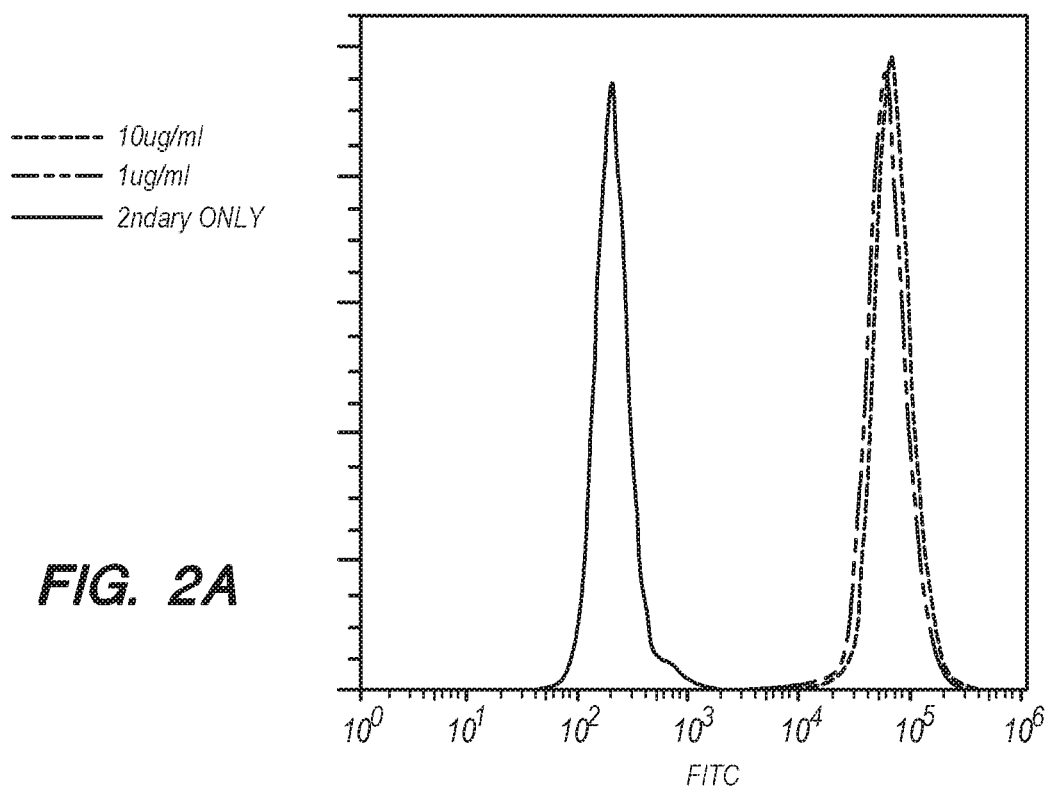
FIGS. 2A-2C are histograms showing binding of anti-BTLA antibody 13-F7A to BTLA by FACS analysis.
Figure 2B:
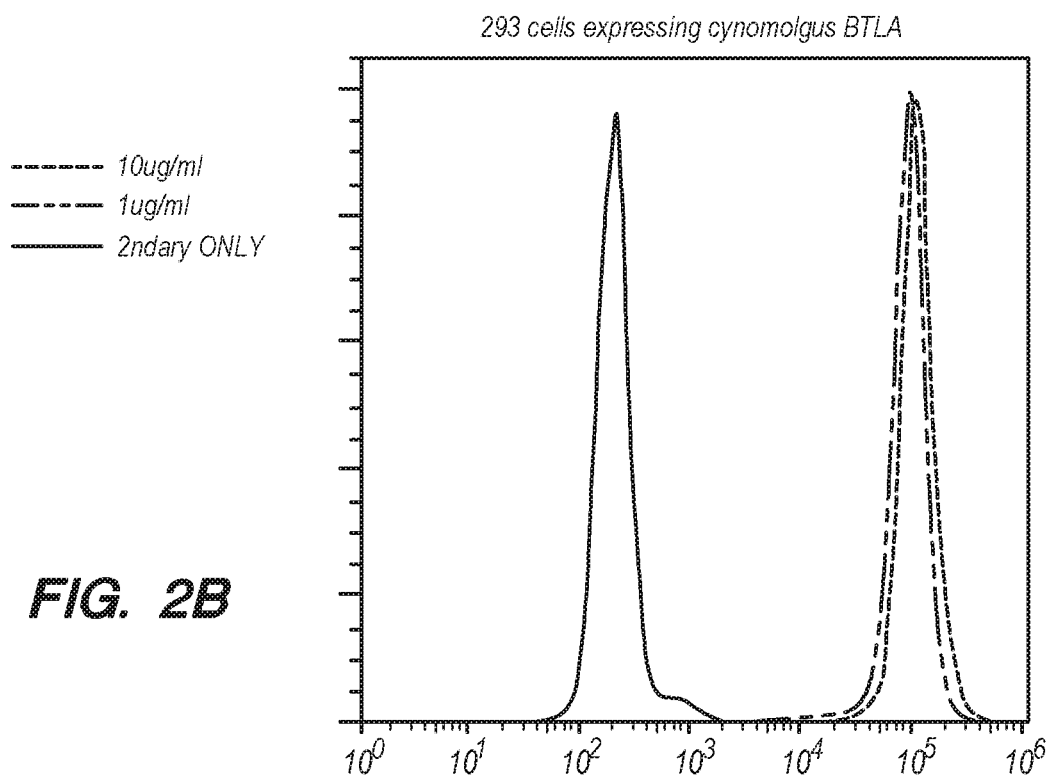
Figure 2C:
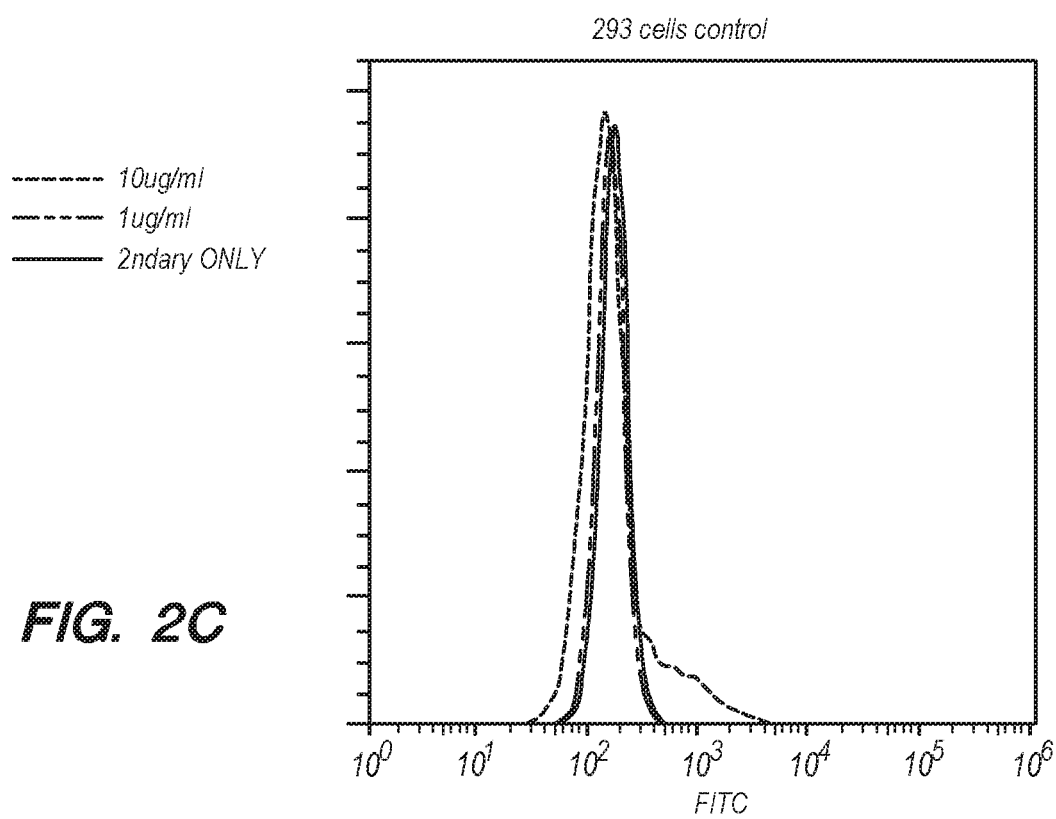

HEK 293 cells expressing human or cynomolgus BTLA were used to assess the binding of anti-BTLA antibodies to BTLA. Various concentrations of an anti-BTLA antibody (67, 22, 7.4, 2.5, 0.8, 0.3, 0.09, 0.03, 0.01, 0.004, and 0.001 nM) were incubated with the cells for 1 hour at room temperature. A fluorophore-conjugated anti-human IgG secondary antibody was then added, and the cells were analyzed by flow cytometry. FIGS. 2A-2B show exemplary binding profile of anti-BTLA antibody 13-F7A to HEK 293 cells that express human or cynomolgus BTLA. Compared with control HEK 293 cells (FIG. 2C), 13-F7A bind to both human BTLA and cynomolgus BTLA. Table 5 summarizes the binding EC50 of various anti-BTLA antibodies to human and cynomolgus BTLA measured by FACS.

TABLE 5

| Clones | Human BTLA (MFI) EC50 (nM) | Cyno BTLA (MFI) EC50 (nM) |
| --- | --- | --- |
| 16-I20A | 5.0 | 6.9 |
| 15-C19A | 5.5 | 4.4 |
| 16-H16A | 4.7 | 4.4 |
| 12-I8A | 2.9 | 5.0 |
| 8-M23A | 3.4 | 4.5 |
| 13-F7A | 1.5 | 2.6 |
| 4C7 comparator | 2.3 | 4.4 |

Example 3—Anti-BTLA Antibodies Inhibit BTLA/HVEM Interaction

Figure 3:
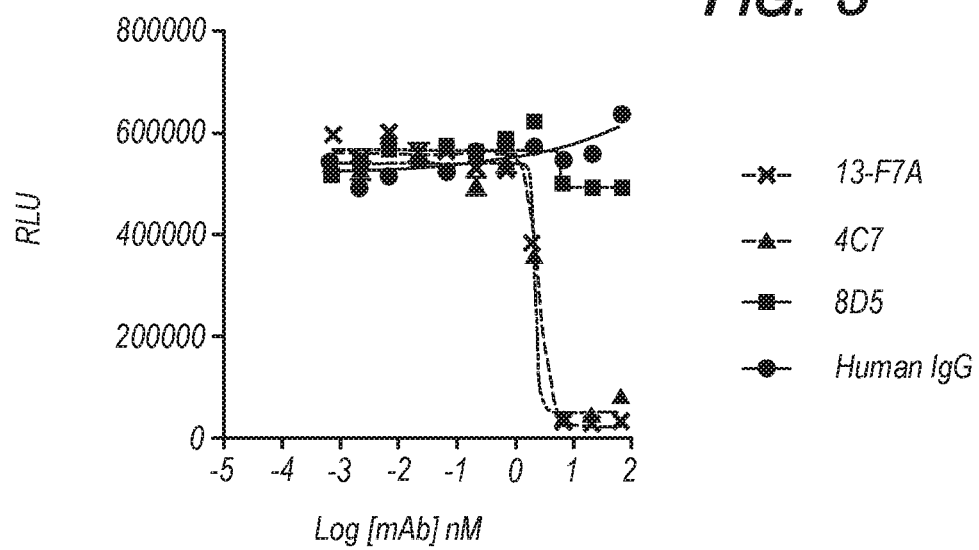
FIG. 3 shows that the anti-BTLA antibody 13-F7A inhibits human BTLA/HVEM interaction by ELISA. Anti-BTLA antibodies 4C7 and 8D5 as well as human IgG were used as controls.

An ELISA-based biofunction assay was used to assay the effect of anti-BTLA antibodies on BTLA/HVEM interaction. Each well of a 384-well ELISA plate was coated with 20 µl of 5 µg/ml human HVEM-ratIgG2a at 37° C. for 1 hr (or overnight at 4° C.). After coating, the plate was washed twice with Molecular Devices Aquamax 2000 plate washer with wash solution (PBS containing 0.05% Tween-20), and then blocked for 1 hr at room temperature (RT) with blocking solution (PBS containing 3% BSA). During the blocking step, 1 µg/ml human BTLA-human Fc or 0.5 µg/ml cynoBTLA-human Fc was mixed with anti-BTLA antibodies, 4C7, 8D5 or human IgG2 control at various concentrations (67, 22, 7.4, 2.5, 0.8, 0.3, 0.09, 0.03, 0.01, 0.004, 0.001 nM). After completion of the blocking step, the plate was washed twice with the plate washer. 20 µl protein/antibody mixture was then added to the plate and incubated for 1 hr at RT. Unbound material was discarded and the plate was washed four times with the plate washer. 20 µl secondary antibody (anti-human Fc-HRP) was then added to each well and incubated for 45 minutes at RT. Unbound material was discarded and the plate was washed eight times with the plate washer. 20 µl chemilluminescent substrate was then added to each well and the luminescence was read at gain 3600, and relative light units (RLU) were calculated. FIG. 3 shows an exemplary profile of anti-BTLA antibody 13-F7A. 13-F7A inhibited human BTLA interaction with human HVEM to a similar extent as 4C7. However, 8D5 and human IgG control has little effect on the interaction between human BTLA and HVEM. Table 6 shows a summary of IC50 for different anti-BTLA antibodies that inhibit the interaction between human BTLA and HVEM as well as the interaction between cynomolgus BTLA and HVEM.

TABLE 6

| Clones | Human BTLA/HVEM binding inhibition IC50 (nM) | Cyno BTLA/HVEM binding inhibition IC50 (nM) |
| --- | --- | --- |
| 16-I20A | 2.9 | 2.5 |
| 15-C19A | 3.5 | 2.4 |
| 16-H16A | 3.0 | 2.3 |
| 12-I8A | 4.4 | 4.6 |
| 8-M23A | 3.3 | 3.2 |
| 13-F7A | 2.5 | 1.8 |
| 4C7 comparator | 2.2 | 2.0 |

Example 4—Anti-BTLA Antibodies Bind to BTLA with High Affinity

Figure 4:
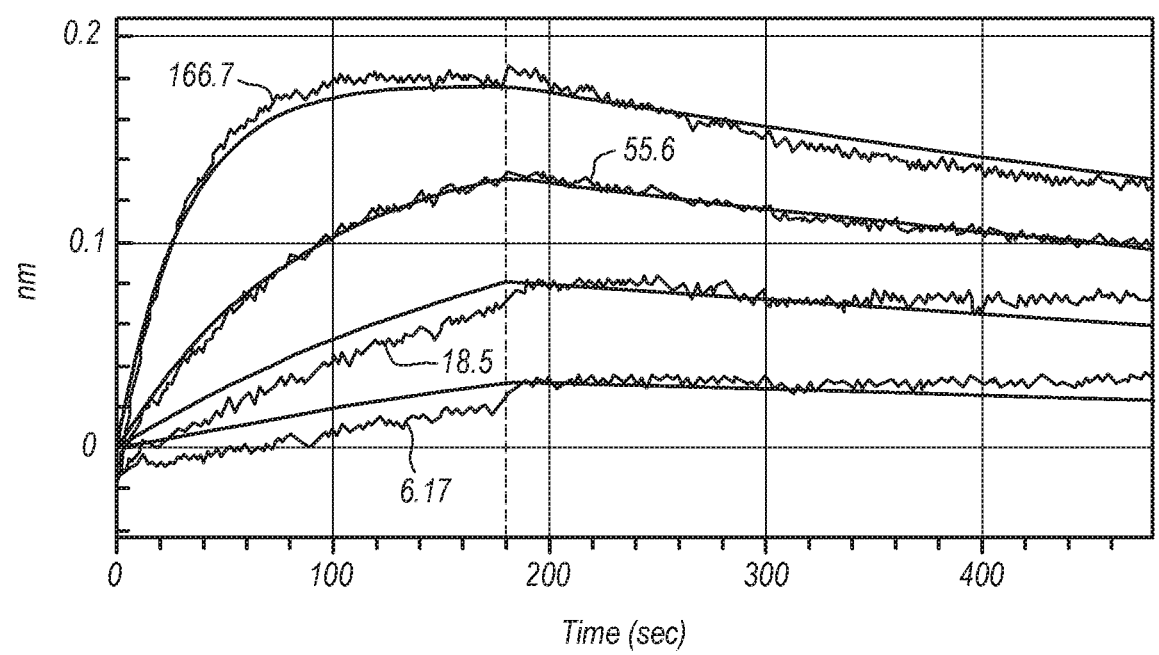
FIG. 4 illustrates the binding affinity of anti-BTLA antibody 13-F7A to human BTLA measured by Bio-Layer Interferometry. 13-F7A was immobilized on the biosensor tip, and 166.7, 55.6, 18.5 and 6.17 nM of recombinant human BTLA were tested. The dissociation constant $K_D$ measured is $5.4 \times 10E-9$ M.
Figure 5A:
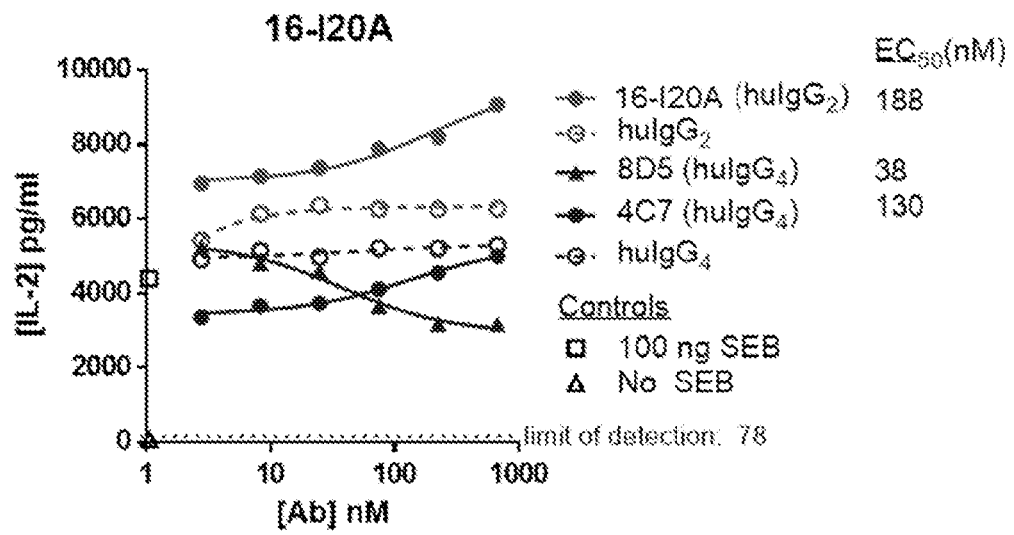
FIGS. 5A-5F show dose-response curve of SEB stimulated IL-2 secretion by primary T cells in the presence of anti-BTLA antibodies. Human IgG2 and IgG4 were used as controls.
Figure 5B:
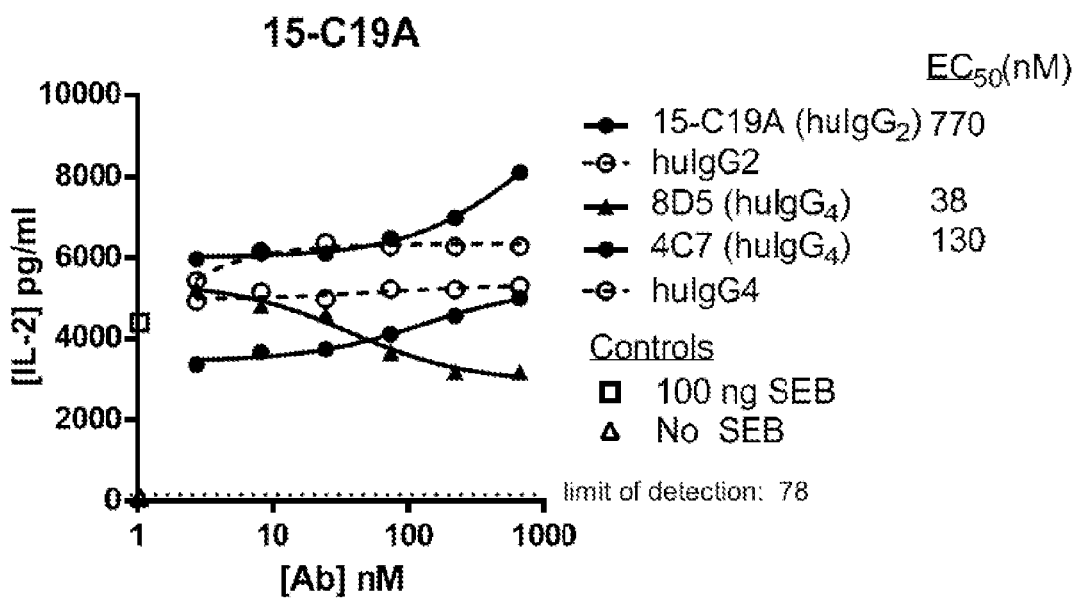
Figure 5C:
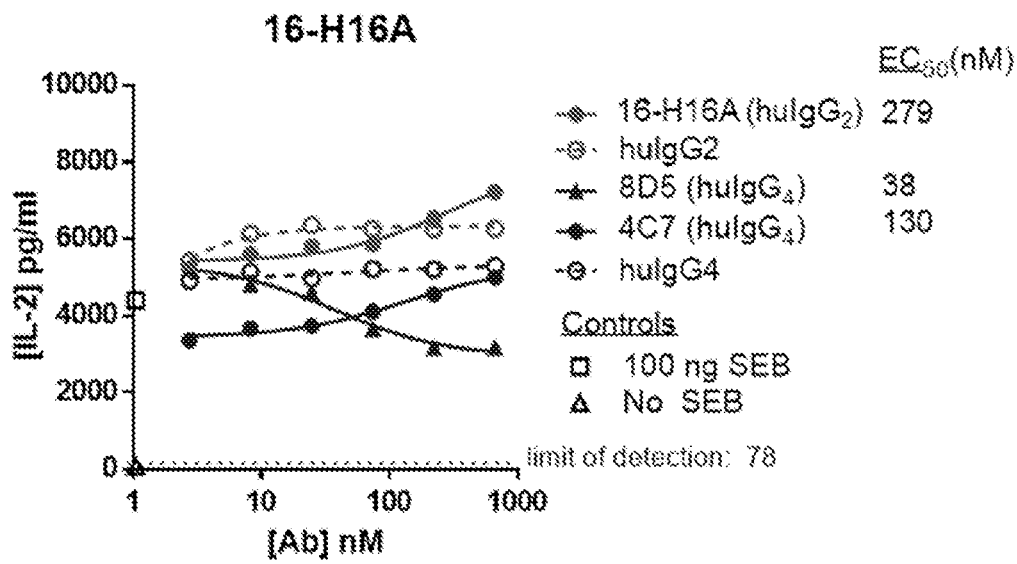
Figure 5D:
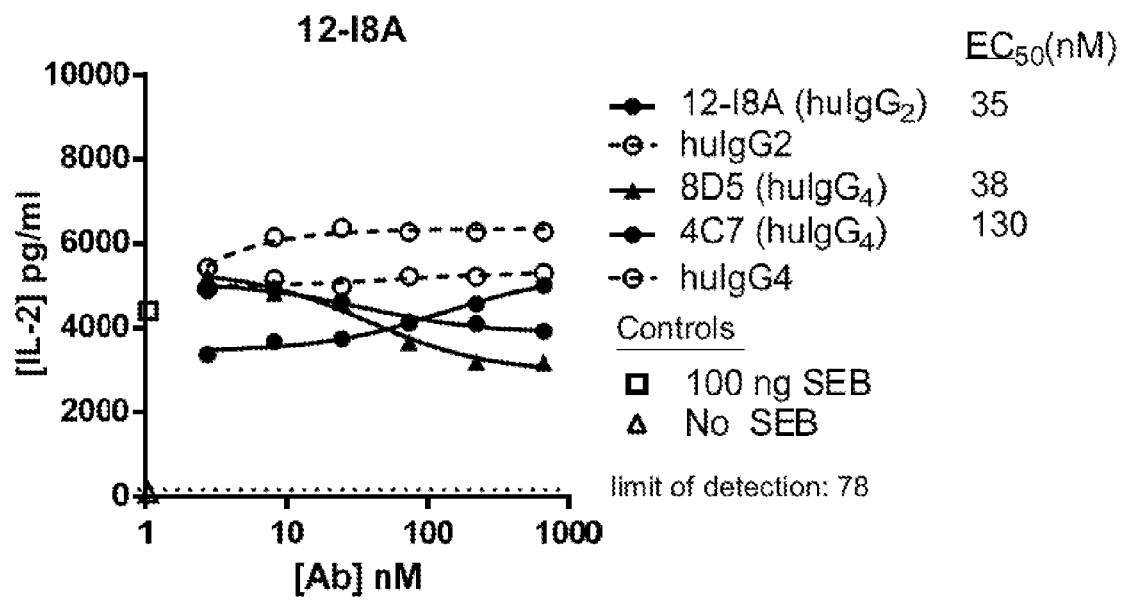
Figure 5E:
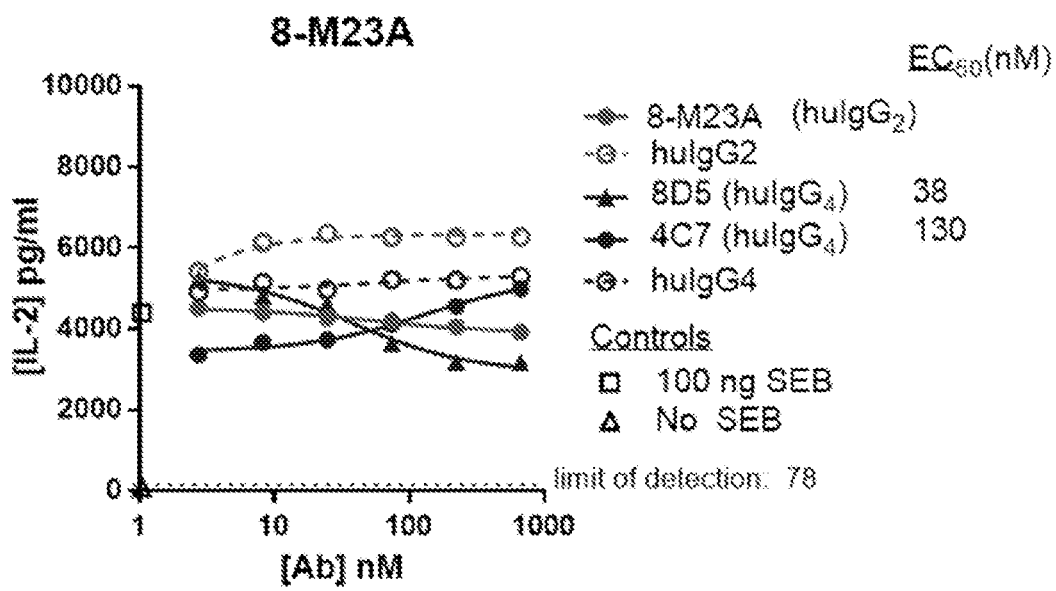
Figure 5F:
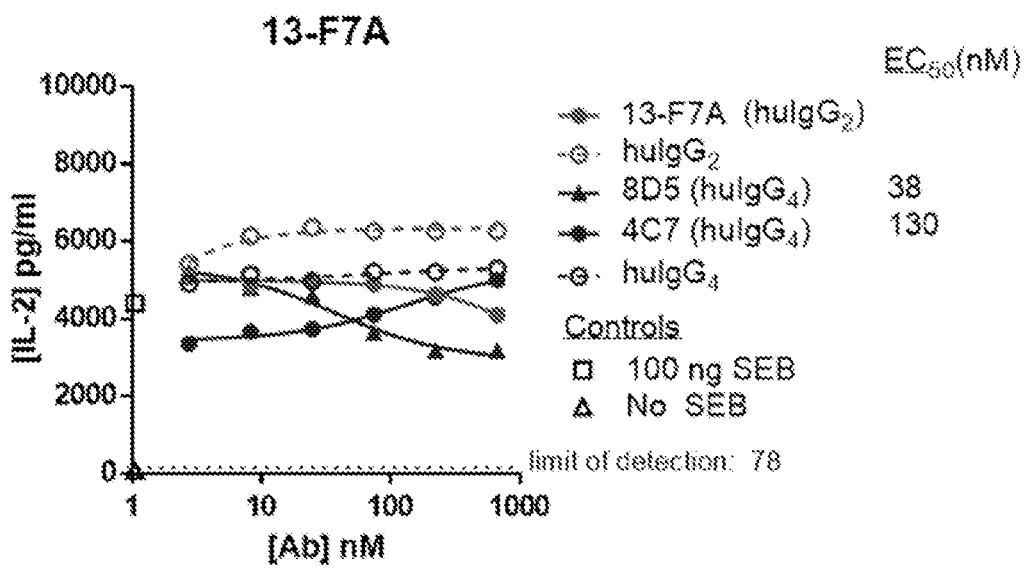

Binding affinities of anti-BTLA antibodies to human and cynomolgus BTLA were measured by Bio-Layer Interferometry (Octet® systems from FortéBIO). 10 µg/ml of each anti-BTLA antibody was immobilized on the biosensor tip surface via anti-human-Fc (AHC) capture. Human or cynomolgus BTLA was diluted in PBS and loaded at concentrations from 166.7 nM to 6.17 nM in 3-fold serial dilutions. Binding curves were fitted to a 1:1 interaction model using the analysis software provided by the Octet® systems. FIG. 4 shows exemplary association and dissociation curves between anti-BTLA antibody 13-F7A and human BTLA at different concentrations (166.7 nM, 55.6 nM, 18.5 nM and 6.17 nM). Table 7 shows a summary of binding dissociation constant ($K_D$) for different anti-BTLA antibodies to human and cynomolgus BTLA measured by Bio-Layer Interferometry.

TABLE 7

| Clones | Human BTLA $K_D$ (nM) | Cyno BTLA $K_D$ (nM) |
|---|---|---|
| 16-I20A | 14.9 | 16.6 |
| 15-C19A | 144.0 | 0.1 |
| 16-H16A | 13.9 | 4.1 |
| 12-I8A | 25.2 | 23.2 |
| 8-M23A | 101.0 | 37.3 |
| 13-F7A | 5.4 | 3.9 |
| 4C7 comparator | 14.2 | 76.5 |

Example 5—Anti-BTLA Antibodies Modulate T Cell Function

Effects of anti-BTLA antibodies on T cell function were assayed. Peripheral blood mononuclear cells (PBMCs) were isolated from heparinized whole blood from human donors by density gradient centrifugation. PBMCs were resuspended at $1 \times 10^6$/ml in complete RPMI 1640 (RPMI 1640, 10% FCS, 1-glutamine, penicillin, and streptomycin) and 100 µl of cells was seeded per well in 96-well cell culture cluster plates. 1 ng/ml Staphylococcal enterotoxin B (SEB), together with each of anti-BTLA antibody was added to the wells. Cells were incubated at 37° C. under 5% $CO_2$ for 48 hours, and the supernatants were collected. The concentration of IL-2 in the supernatant was measured by ELISA using anti-IL2 capture antibody (R&D system MAB602).

FIGS. 5A-5F show dose-response curves of released IL-2 from primary T cells in the presence of different anti-BTLA antibodies and SEB. Human IgG2 and IgG4 were used as controls for the assay, since in this example anti-BTLA antibodies comprise an Fc domain from human IgG2 and 8D5 and 4C7 each comprises an Fc domain from human IgG4. Anti-BTLA antibodies 16-I20A, 15-C19A and 16-H16A augmented SEB-induced IL-2 secretion by T cells, and thus served as BTLA antagonists. In addition, they displayed higher maximal antagonistic activity compared to the 4C7 antibody. EC50 of each antibody tested was calculated, and 16-I20A displayed similar EC50, i.e., potency in antagonizing T cell function compared to 4C7 antibody. Anti-BTLA antibodies 12-IBA, 8-M23A and 13-F7A suppressed SEB-induced IL-2 secretion by T cells, and thus served as BTLA agonists.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An antibody that binds to BTLA comprising: a heavy chain variable region comprising the amino acid sequence of SEQ ID NO: 19 and a light chain variable region comprising the amino acid sequence of SEQ ID NO:20.

2. An antibody that binds to BTLA comprising: a vhCDR1 comprising SEQ ID NO: 101, a vhCDR2 comprising SEQ ID NO: 102, a vhCDR3 comprising SEQ ID NO: 103, a vlCDR1 comprising SEQ ID NO: 104, a vlCDR2 comprising SEQ ID NO: 105, and a vlCDR3 comprising SEQ ID NO:106.

3. The antibody according to claim 2, wherein the antibody comprises a heavy chain variable region comprising the amino acid sequence of SEQ ID NO: 19 and a light chain variable region comprising the amino acid sequence of SEQ ID NO:20; and wherein the antibody serves as a BTLA agonist, and suppresses pro-inflammatory T cell functions.

4. The antibody according to claim 2, wherein the antibody comprises a constant region with an amino acid sequence at least 90% identical to a human IgG.

5. The antibody according to claim 4, wherein the human IgG is selected from a group consisting of IgG1, IgG2, IgG3 and IgG4.

6. The antibody according to claim 5, wherein the IgG is an IgG2.

7. A composition comprising the antibody according to claim 2, and a pharmaceutical acceptable carrier or diluent.

* * * * *